US012564122B2

(12) United States Patent
    Strnad

(10) Patent No.: US 12,564,122 B2
(45) Date of Patent: Mar. 3, 2026

(54) SYSTEMS AND APPARATUSES FOR SOIL AND SEED MONITORING

(71) Applicant: Precision Planting, LLC, Tremont, IL (US)

(72) Inventor: Michael Strnad, Delavan, IL (US)

(73) Assignee: Precision Planting, LLC, Tremont, IL (US)

( * ) Notice: Subject to any disclaimer, the term of this patent is extended or adjusted under 35 U.S.C. 154(b) by 675 days.

(21) Appl. No.: 18/060,266

(22) Filed: Nov. 30, 2022

(65) Prior Publication Data

US 2023/0093226 A1 Mar. 23, 2023

Related U.S. Application Data

(60) Division of application No. 16/831,773, filed on Mar. 26, 2020, now Pat. No. 11,612,098, which is a
(Continued)

(51) Int. Cl.
    *A01C 5/06* (2006.01)
    *A01B 49/06* (2006.01)
    (Continued)

(52) U.S. Cl.
    CPC .............. *A01C 5/068* (2013.01); *A01B 49/06* (2013.01); *A01B 61/00* (2013.01); *A01B 61/04* (2013.01); *A01B 61/042* (2013.01); *A01B 79/02* (2013.01); *A01C 7/201* (2013.01); *A01C 7/203* (2013.01); *A01C 7/205* (2013.01); *A01C 14/00* (2013.01); *A01C 21/00* (2013.01); *G01N 33/24* (2013.01); *G01N 33/246* (2013.01); *A01B 79/005* (2013.01); *G01N 33/245* (2024.05)

(58) Field of Classification Search
    CPC ........... A01C 5/068; A01C 5/066; A01C 5/06; A01C 5/00; A01C 7/20; A01C 7/00; A01C 7/201; A01C 7/203; A01C 7/205; A01C 14/00; A01C 21/00; A01B 49/06; A01B 61/00; A01B 61/04; A01B 61/042; A01B 79/02; A01B 49/04; A01B 49/00; A01B 79/00; G01N 33/24; G01N 33/246; G01N 33/00; G01N 33/245; G01N 79/005
    See application file for complete search history.

(56) References Cited

U.S. PATENT DOCUMENTS

| | | | |
|---|---|---|---|
| 10,262,413 B2 | 4/2019 | Strnad et al. | |
| 10,512,212 B2 | 12/2019 | Koch et al. | |

(Continued)

FOREIGN PATENT DOCUMENTS

JP      2012231684 A    11/2012

OTHER PUBLICATIONS

Dolschak, Klaus et al, A New Approach to Predict Soil Temperature Under Vegetated Surfaces, Modeling Earth Systems and Environment [Online], vol. 1, No. 4, Oct. 29, 2015, 14 pages, XP093062481, ISSN: 2363-6203, Retrieved from the Internet: URL: http://link.springer.com/article/10.1007/s40808-015-0041-2/fulltext.html>.
(Continued)

*Primary Examiner* — Christopher J. Novosad

(57) ABSTRACT

A soil apparatus is drawn through a furrow and reflectance from the furrow is obtained from the soil apparatus, and a height off target is measured between the soil apparatus and the furrow.

3 Claims, 80 Drawing Sheets

Related U.S. Application Data continuation of application No. PCT/US2018/053832, filed on Oct. 2, 2018.

(60) Provisional application No. 62/661,783, filed on Apr. 24, 2018, provisional application No. 62/625,855, filed on Feb. 2, 2018, provisional application No. 62/567,135, filed on Oct. 2, 2017.

(51) Int. Cl.

| | |
|---|---|
| *A01B 61/00* | (2006.01) |
| *A01B 61/04* | (2006.01) |
| *A01B 79/00* | (2006.01) |
| *A01B 79/02* | (2006.01) |
| *A01C 7/20* | (2006.01) |
| *A01C 14/00* | (2006.01) |
| *A01C 21/00* | (2006.01) |
| *G01N 33/24* | (2006.01) |

(56) References Cited

U.S. PATENT DOCUMENTS

| | | | |
|---|---|---|---|
| 11,285,063 | B2 | 3/2022 | Davis |
| 11,457,557 | B2 | 10/2022 | Koch et al. |

| | | | |
|---|---|---|---|
| 2015/0112595 | A1 | 4/2015 | Brehmer et al. |
| 2015/0334914 | A1 | 11/2015 | Zielke |
| 2017/0049044 | A1* | 2/2017 | Stoller ................... A01C 7/201 |

OTHER PUBLICATIONS

European Patent Office, Extended European Search Report related to European Patent Application No. 23167609.9, mail date Aug. 3, 2023, 9 pages.

European Patent Office, Extended European Search Report related to European Patent Application No. 23167616.4, mail date Jul. 4, 2023, 8 pages.

European Patent Office, Extended European Search Report related to European Patent Application No. 23167610.7, mail date Jul. 20, 2023, 14 pages.

European Patent Office, Extended European Search Report related to European Patent Application No. 23167615.6, mail date Jul. 21, 2023, 9 pages.

European Patent Office, Extended European Search Report related to European Patent Application No. 23167614.9, mail date Aug. 11, 2023, 9 pages.

European Patent Office, Extended European Search Report related to European Patent Application No. 23167612.3 mail date Jul. 20, 2023, 10 pages.

European Patent Office, Extended European Search Report related to European Patent Application No. 23167613.1 mail date Aug. 7, 2023, 10 pages.

* cited by examiner

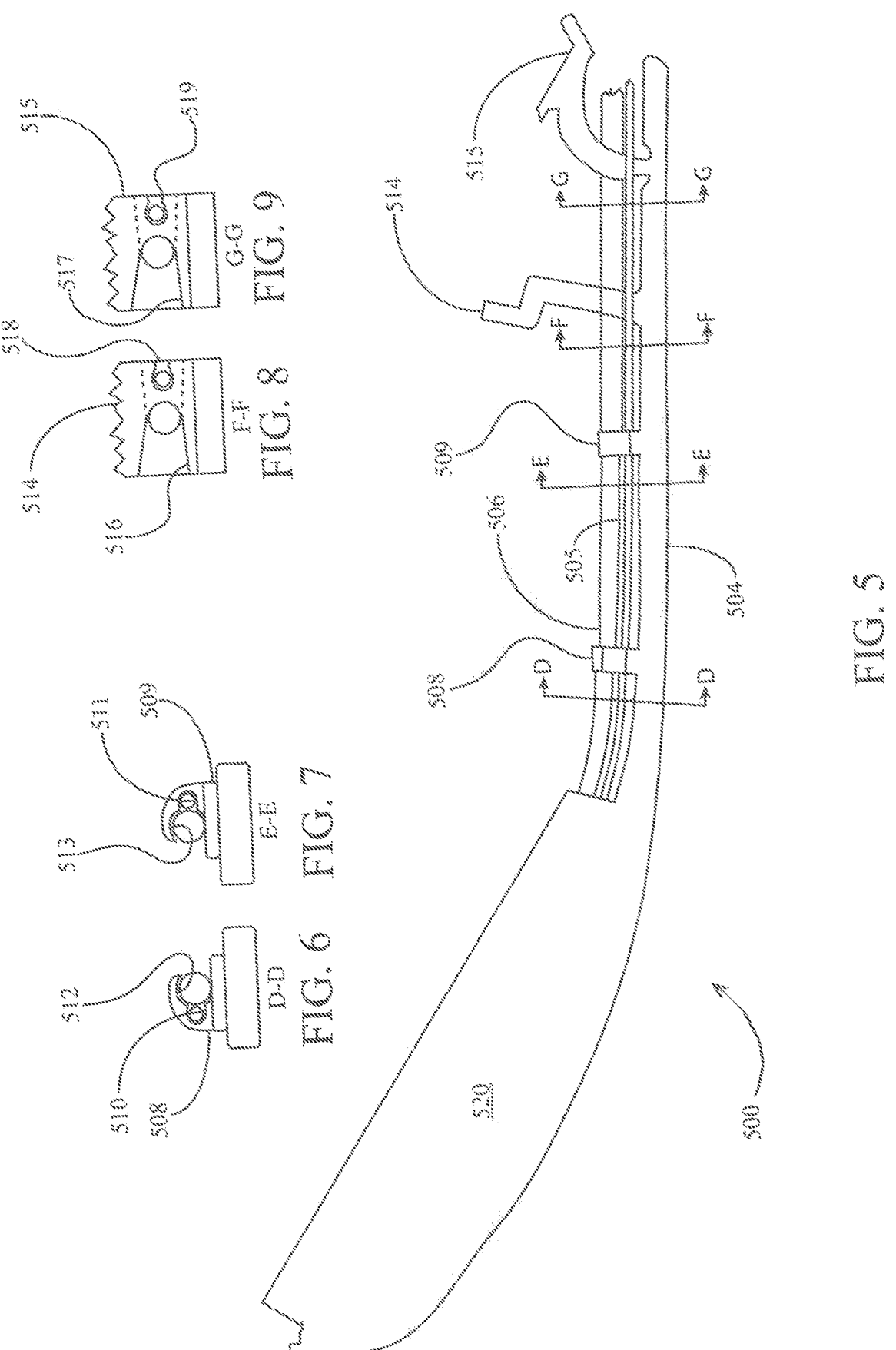

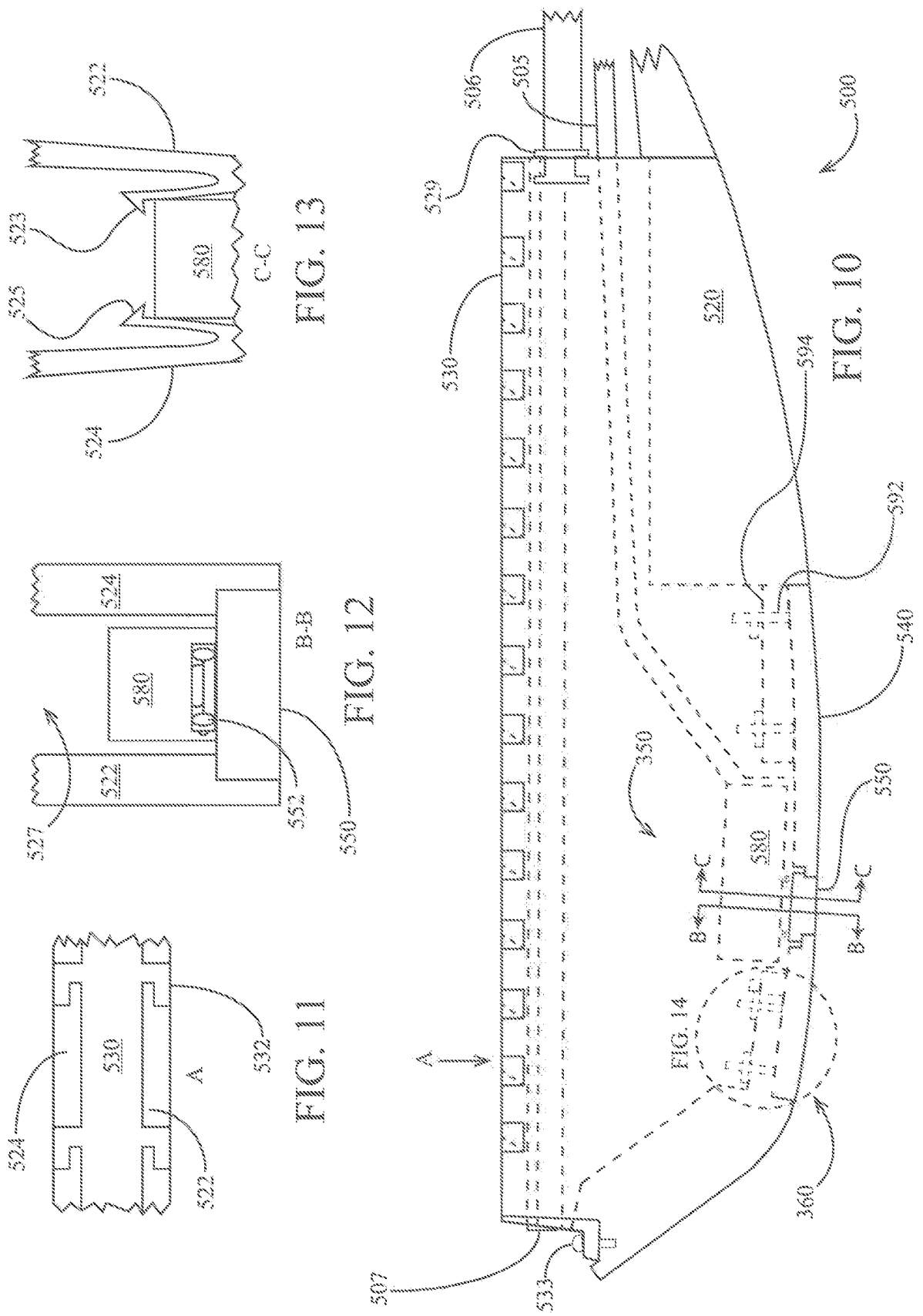

495'

*496'*

350

350-e        350-d        350-e        38

350

350-e-1        350-d        350-e-2        459-2        459-1        450"        38

450

450

450

450

450

4900

OBTAIN, WITH A SYSTEM, SOIL MEASUREMENTS (E.G., MEASUREMENTS FOR MOISTURE, ORGANIC MATTER, POROSITY, TEXTURE/TYPE OF SOIL, FURROW RESIDUE, ETC.)
4902

GENERATE, WITH THE SYSTEM, A SIGNAL TO ACTUATE ANY IMPLEMENT ON ANY AGRICULTURAL IMPLEMENT (E.G., CHANGE A POPULATION OF PLANTED SEEDS BY CONTROLLING A SEED METER, CHANGE SEED VARIETY (E.G., HYBRID), CHANGE FURROW DEPTH, CHANGE APPLICATION RATE OF FERTILIZER, FUNGICIDE, AND/OR INSECTICIDE, CHANGE APPLIED DOWNFORCE OR UPFORCE OF AN AGRICULTURAL IMPLEMENT, SUCH AS A PLANTER OR TILLER, CONTROL THE FORCE APPLIED BY A ROW CLEANER) IN RESPONSE TO OBTAINING SOIL MEASUREMENTS
4904

| Seed Environment Score Properties | | |
| --- | --- | --- |
| Property | Value | In Acceptable Range |
| Current Temperature | 60°F | Yes |
| Current Moisture | 3% | Yes |
| Predicted Temperature | 50°F | No |
| Predicted Moisture | 3% | Yes |

SYSTEMS AND APPARATUSES FOR SOIL AND SEED MONITORING

CROSS REFERENCE TO RELATED APPLICATIONS

This application is a divisional application of U.S. application Ser. No. 16/831,773, filed 26 Mar. 2020, which is a national stage entry of PCT Application No. PCT/US2018/053832, filed 2 Oct. 2018, and claims the benefit of U.S. Provisional Application No. 62/567,135, filed on Oct. 2, 2017 entitled: SYSTEMS AND APPARATUSES FOR SOIL AND SEED MONITORING; U.S. Provisional Application No. 62/625,855, filed on Feb. 2, 2018 entitled: SYSTEMS AND APPARATUSES FOR SOIL AND SEED MONITORING; U.S. Provisional Application No. 62/661,783, filed on Apr. 24, 2018 entitled: SYSTEMS AND APPARATUSES FOR SOIL AND SEED MONITORING, the entire contents of each are hereby incorporated by reference.

TECHNICAL FIELD

Embodiments of the present disclosure relate to systems and apparatuses for agricultural soil and seed monitoring.

BACKGROUND

In recent years, the availability of advanced location-specific agricultural application and measurement systems (used in so-called "precision farming" practices) has increased grower interest in determining spatial variations in soil properties and in varying input application variables (e.g., planting depth) in light of such variations. However, the available mechanisms for measuring properties such as temperature are either not effectively locally made throughout the field or are not made at the same time as an input (e.g. planting) operation.

BRIEF DESCRIPTION OF THE DRAWINGS

The present disclosure is illustrated by way of example, and not by way of limitation, in the figures of the accompanying drawings and in which:

FIG. 5 is a side elevation view of another embodiment of a seed firmer having a plurality of firmer-mounted sensors.

FIG. 6 is a sectional view along section D-D of FIG. 5.

FIG. 7 is a sectional view along section E-E of FIG. 5.

FIG. 8 is a sectional view along section F-F of FIG. 5.

FIG. 9 is a sectional view along section G-G of FIG. 5.

FIG. 10 is a partially cutaway partial side view of the seed firmer of FIG. 5.

FIG. 11 is a view along direction A of FIG. 10.

FIG. 12 is a view along section B-B of FIG. 10.

FIG. 13 is a view along section C-C of FIG. 10.

FIG. 49 illustrates a flow diagram of one embodiment for a method 4900 of obtaining soil measurements and then generating a signal to actuate any implement on any agricultural implement.

FIG. 72 illustrates an embodiment of a seed environment score properties screen.

BRIEF SUMMARY

A soil apparatus (e.g., seed firmer) having a locking system is described herein. In one embodiment, the soil apparatus includes a lower base portion for engaging in soil of an agricultural field, an upper base portion, and a neck portion having protrusions to insert into the lower base portion of a base and then lock when a region of the upper base portion is inserted into the lower base portion and this region of the upper base portion presses the protrusions to lock the neck portion to the upper base portion.

DETAILED DESCRIPTION

All references cited herein are incorporated herein in their entireties. If there is a conflict between a definition herein and in an incorporated reference, the definition herein shall control.

The terms trench and furrow are used interchangeably throughout this specification.

Depth Control and Soil Monitoring Systems

Figure 1:
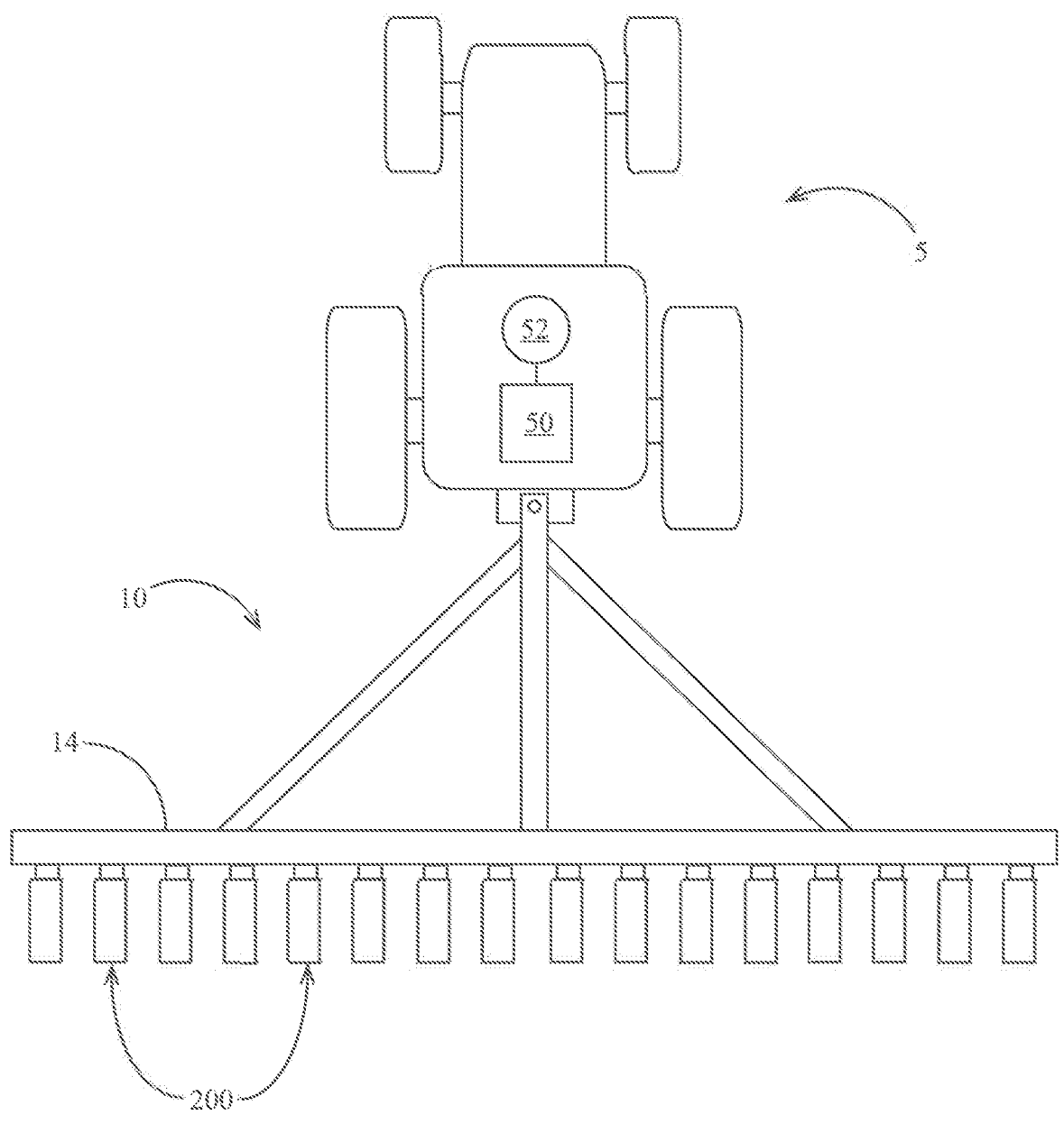
FIG. 1 is a top view of an embodiment of an agricultural planter.

Referring now to the drawings, wherein like reference numerals designate identical or corresponding parts throughout the several views, FIG. 1 illustrates a tractor 5 drawing an agricultural implement, e.g., a planter 10, comprising a toolbar 14 operatively supporting multiple row units 200. An implement monitor 50 preferably including a central processing unit ("CPU"), memory and graphical user interface ("GUI") (e.g., a touch-screen interface) is preferably located in the cab of the tractor 5. A global positioning system ("GPS") receiver 52 is preferably mounted to the tractor 5.

Figure 2:
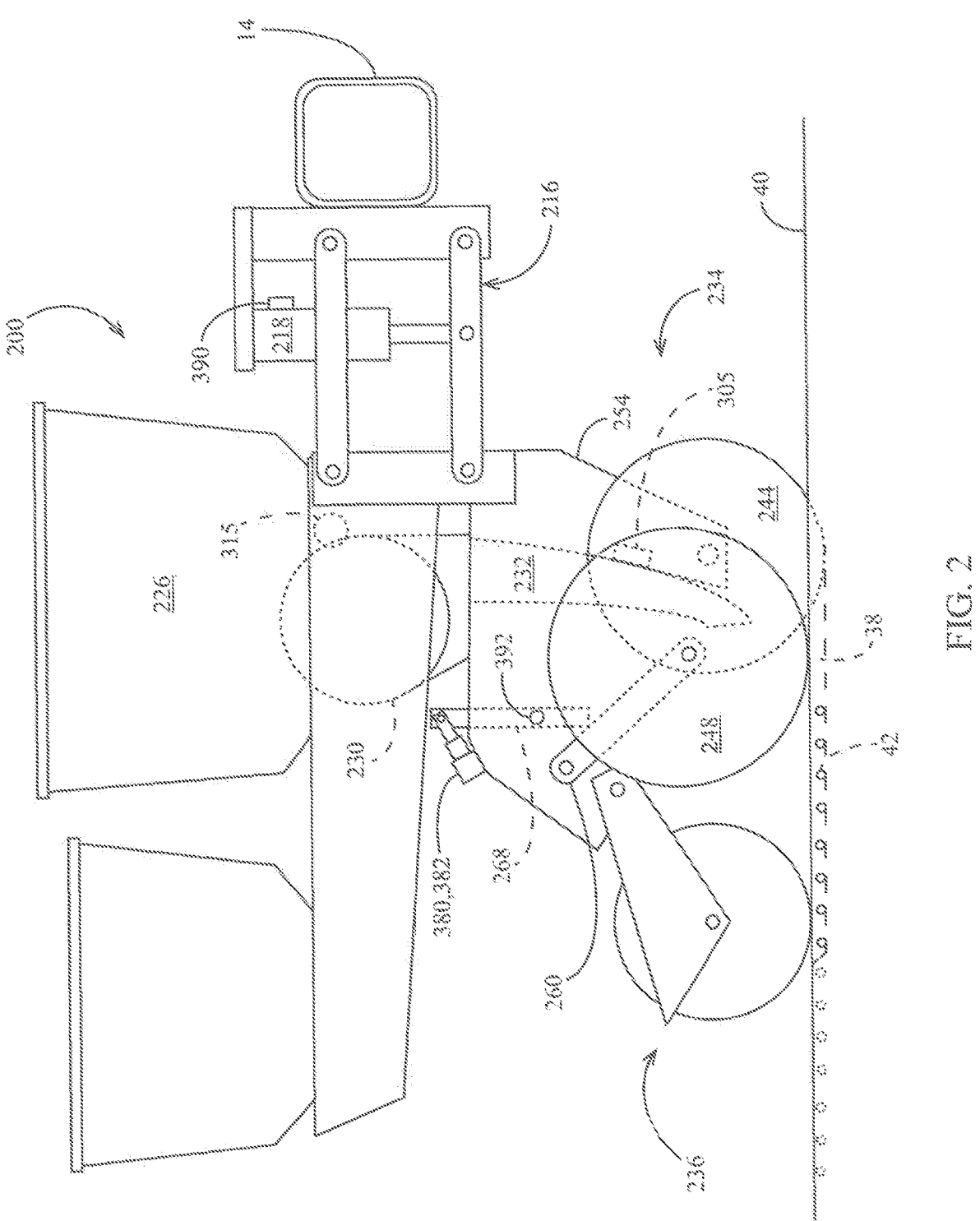
FIG. 2 is a side elevation view of an embodiment of a planter row unit.

Turning to FIG. 2, an embodiment is illustrated in which the row unit 200 is a planter row unit. The row unit 200 is preferably pivotally connected to the toolbar 14 by a parallel linkage 216. An actuator 218 is preferably disposed to apply lift and/or downforce on the row unit 200. A solenoid valve 390 is preferably in fluid communication with the actuator 218 for modifying the lift and/or downforce applied by the actuator. An opening system 234 preferably includes two opening discs 244 rollingly mounted to a downwardly-extending shank 254 and disposed to open a v-shaped trench 38 in the soil 40. A pair of gauge wheels 248 is pivotally supported by a pair of corresponding gauge wheel arms 260; the height of the gauge wheels 248 relative to the opener discs 244 sets the depth of the trench 38. A depth adjustment rocker 268 limits the upward travel of the gauge wheel arms 260 and thus the upward travel of the gauge wheels 248. A depth adjustment actuator 380 is preferably configured to modify a position of the depth adjustment rocker 268 and thus the height of the gauge wheels 248. The actuator 380 is preferably a linear actuator mounted to the row unit 200 and pivotally coupled to an upper end of the rocker 268. In some embodiments the depth adjustment actuator 380 comprises a device such as that disclosed in International Patent Application No. PCT/US2012/035585 ("the '585 application") or International Patent Application Nos. PCT/US2017/018269 or PCT/US2017/018274. An encoder 382 is preferably configured to generate a signal related to the linear extension of the actuator 380; it should be appreciated that the linear extension of the actuator 380 is related to the depth of the trench 38 when the gauge wheel arms 260 are in contact with the rocker 268. A downforce sensor 392 is preferably configured to generate a signal related to the amount of force imposed by the gauge wheels 248 on the soil 40; in some embodiments the downforce sensor 392 comprises an instrumented pin about which the rocker 268 is pivotally coupled to the row unit 200, such as those instrumented pins disclosed in Applicant's U.S. patent application Ser. No. 12/522,253 (Pub. No. US 2010/0180695A1).

Continuing to refer to FIG. 2, a seed meter 230 such as that disclosed in Applicant's International Patent Application No. PCT/US2012/030192 is preferably disposed to deposit seeds 42 from a hopper 226 into the trench 38, e.g., through a seed tube 232 disposed to guide the seeds toward the trench. In some embodiments, instead of a seed tube 232, a seed conveyor is implemented to convey seeds from the seed meter to the trench at a controlled rate of speed as disclosed in U.S. patent application Ser. No. 14/347,902 and/or U.S. Pat. No. 8,789,482B2. In such embodiments, a bracket such as that shown in FIG. 30 is preferably configured to mount the seed firmer to the shank via sidewalls extending laterally around the seed conveyor, such that the seed firmer is disposed behind the seed conveyor to firm seeds into the soil after they are deposited by the seed conveyor. In some embodiments, the meter is powered by an electric drive 315 configured to drive a seed disc within the seed meter. In other embodiments, the drive 315 may comprise a hydraulic drive configured to drive the seed disc. A seed sensor 305 (e.g., an optical or electromagnetic seed sensor configured to generate a signal indicating passage of a seed) is preferably mounted to the seed tube 232 and disposed to send light or electromagnetic waves across the path of seeds 42. A closing system 236 including one or more closing wheels is pivotally coupled to the row unit 200 and configured to close the trench 38.

Figure 3:
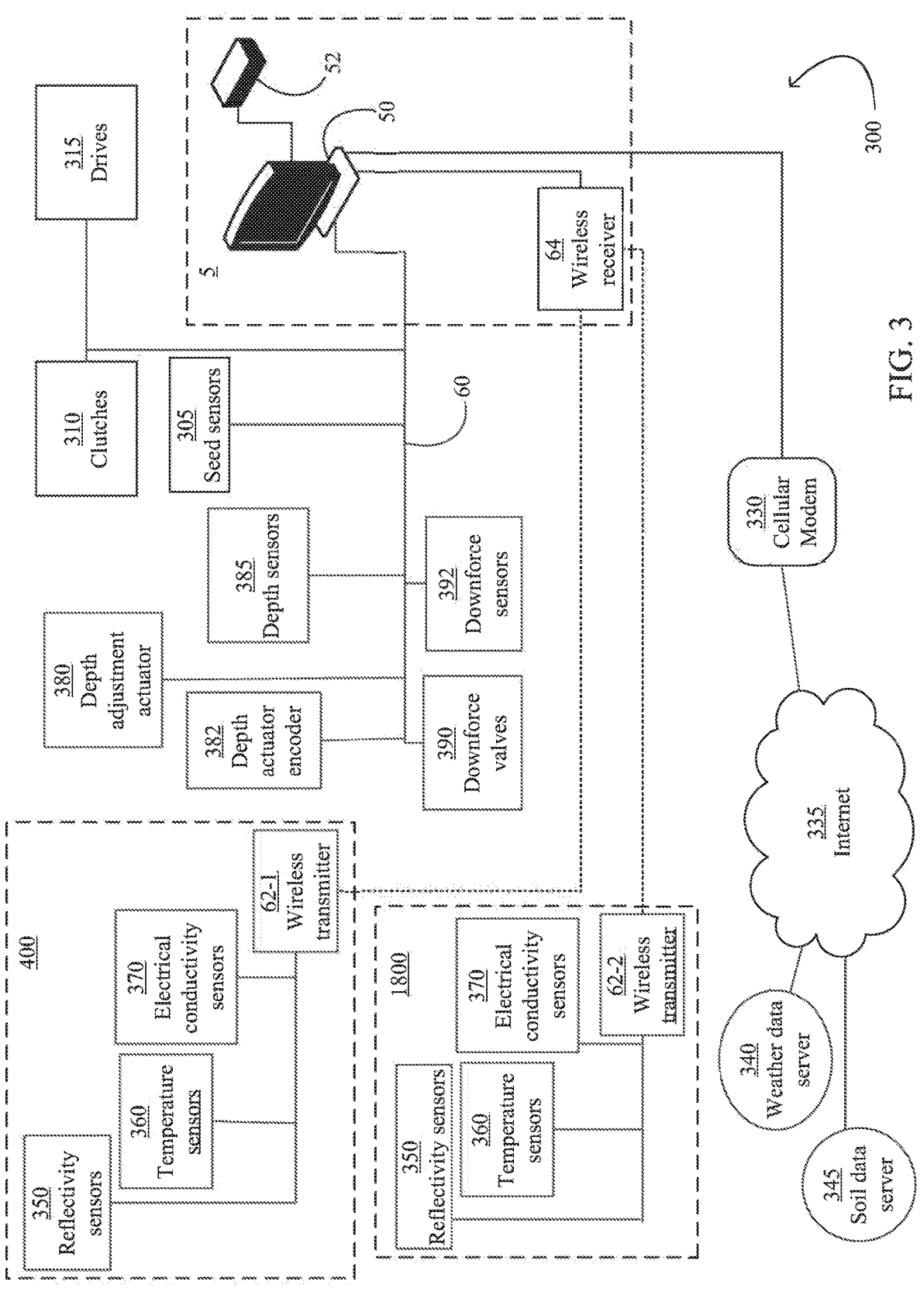
FIG. 3 schematically illustrates an embodiment of a soil monitoring system.

Turning to FIG. 3, a depth control and soil monitoring system 300 is schematically illustrated. The monitor 50 is preferably in data communication with components associated with each row unit 200 including the drives 315, the seed sensors 305, the GPS receiver 52, the downforce sensors 392, the valves 390, the depth adjustment actuator 380, and the depth actuator encoders 382. In some embodiments, particularly those in which each seed meter 230 is not driven by an individual drive 315, the monitor 50 is also preferably in data communication with clutches 310 configured to selectively operably couple the seed meter 230 to the drive 315.

Continuing to refer to FIG. 3, the monitor 50 is preferably in data communication with a cellular modem 330 or other component configured to place the monitor 50 in data communication with the Internet, indicated by reference numeral 335. The internet connection may comprise a wireless connection or a cellular connection. Via the Internet connection, the monitor 50 preferably receives data from a weather data server 340 and a soil data server 345. Via the Internet connection, the monitor 50 preferably transmits measurement data (e.g., measurements described herein) to a recommendation server (which may be the same server as the weather data server 340 and/or the soil data server 345) for storage and receives agronomic recommendations (e.g., planting recommendations such as planting depth, whether to plant, which fields to plant, which seed to plant, or which crop to plant) from a recommendation system stored on the server; in some embodiments, the recommendation system updates the planting recommendations based on the measurement data provided by the monitor 50.

Continuing to refer to FIG. 3, the monitor 50 is also preferably in data communication with one or more temperature sensors 360 mounted to the planter 10 and configured to generate a signal related to the temperature of soil being worked by the planter row units 200. The monitor 50 is preferably in data communication with one or more reflectivity sensors 350 mounted to the planter 10 and configured to generate a signal related to the reflectivity of soil being worked by the planter row units 200.

Referring to FIG. 3, the monitor 50 is preferably in data communication with one or more electrical conductivity sensors 370 mounted to the planter 10 and configured to generate a signal related to the temperature of soil being worked by the planter row units 200.

In some embodiments, a first set of reflectivity sensors 350, temperature sensors 360, and electrical conductivity sensors are mounted to a seed firmer 400 and disposed to measure reflectivity, temperature and electrical conductivity, respectively, of soil in the trench 38. In some embodiments, a second set of reflectivity sensors 350, temperature sensors 360, and electrical conductivity sensors 370 are mounted to a reference sensor assembly 1800 and disposed to measure reflectivity, temperature and electrical conductivity, respectively, of the soil, preferably at a depth different than the sensors on the seed firmer 400.

In some embodiments, a subset of the sensors are in data communication with the monitor 50 via a bus 60 (e.g., a CAN bus). In some embodiments, the sensors mounted to the seed firmer 400 and the reference sensor assembly 1800 are likewise in data communication with the monitor 50 via the bus 60. However, in the embodiment illustrated in FIG. 3, the sensors mounted to the seed firmer 400 and the reference sensor assembly 1800 are in data communication with the monitor 50 via a first wireless transmitter 62-1 and a second wireless transmitter 62-2, respectively. The wireless transmitters 62 at each row unit are preferably in data communication with a single wireless receiver 64 which is in turn in data communication with the monitor 50. The wireless receiver may be mounted to the toolbar 14 or in the cab of the tractor 5.

Soil Monitoring, Seed Monitoring and Seed Firming Apparatus

Figure 4A:
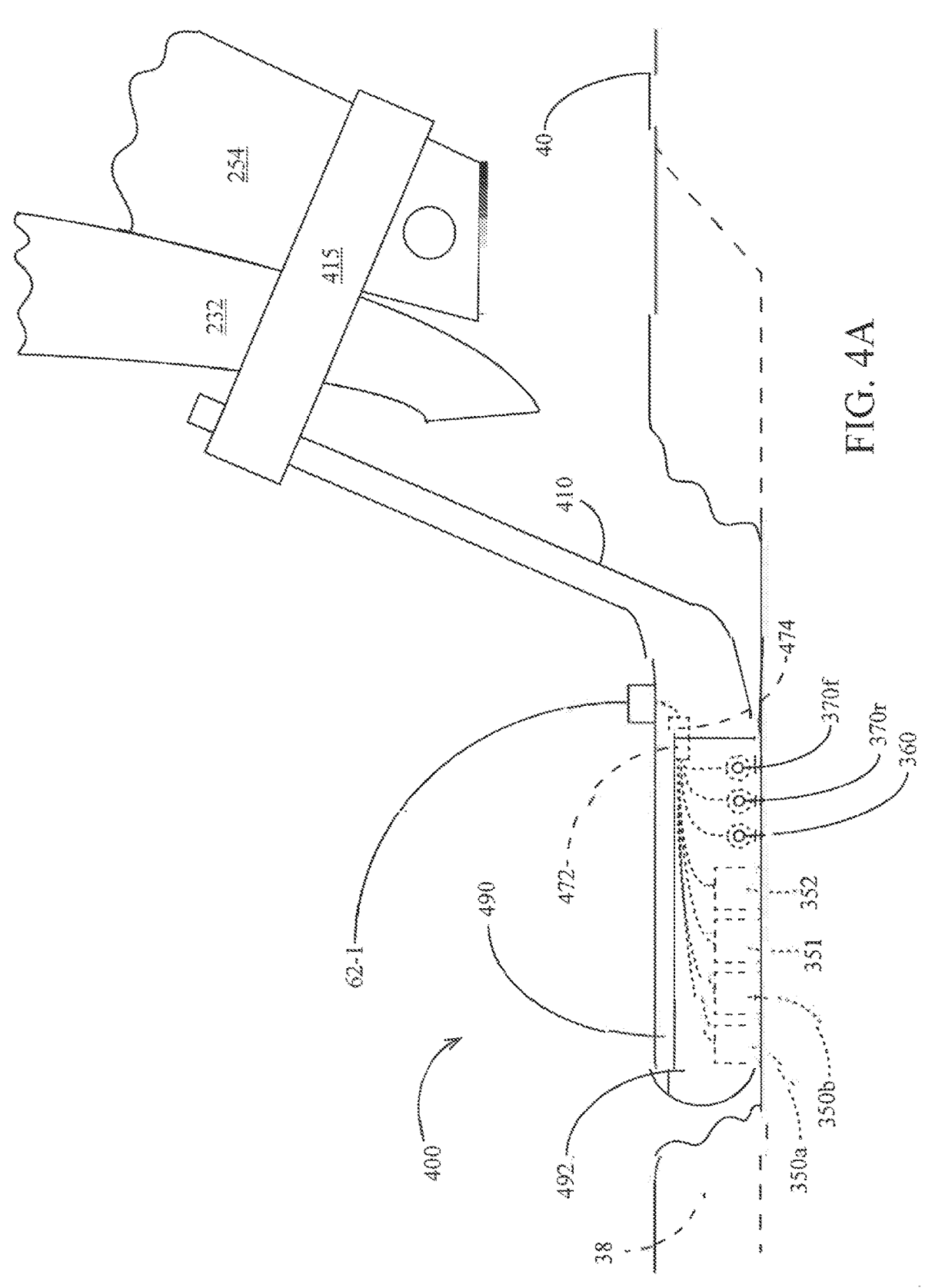
FIG. 4A is a side elevation view of an embodiment of a seed firmer having a plurality of firmer-mounted sensors.
Figure 4B:
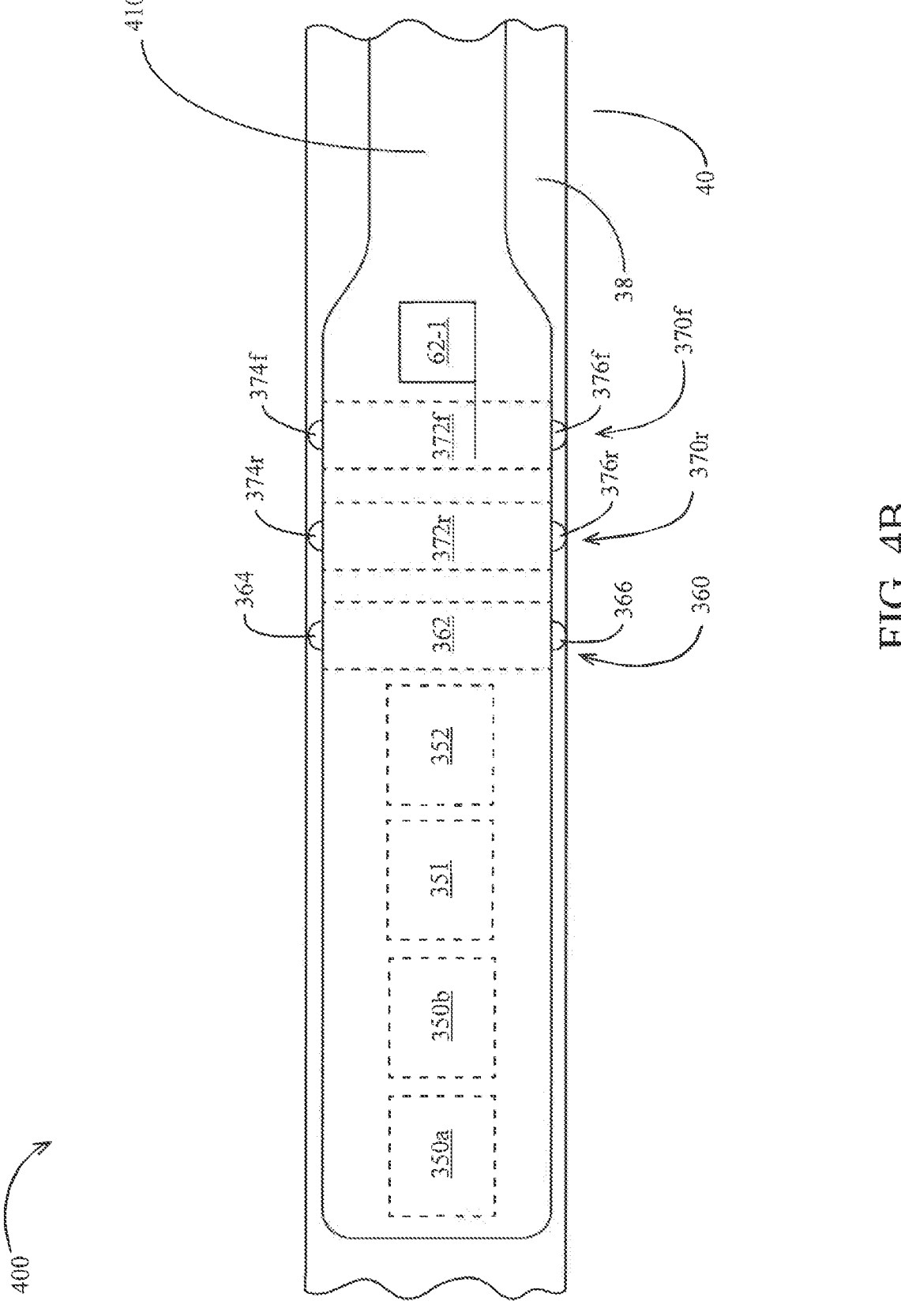
FIG. 4B is a plan view of the seed firmer of FIG. 4A.
Figure 4C:
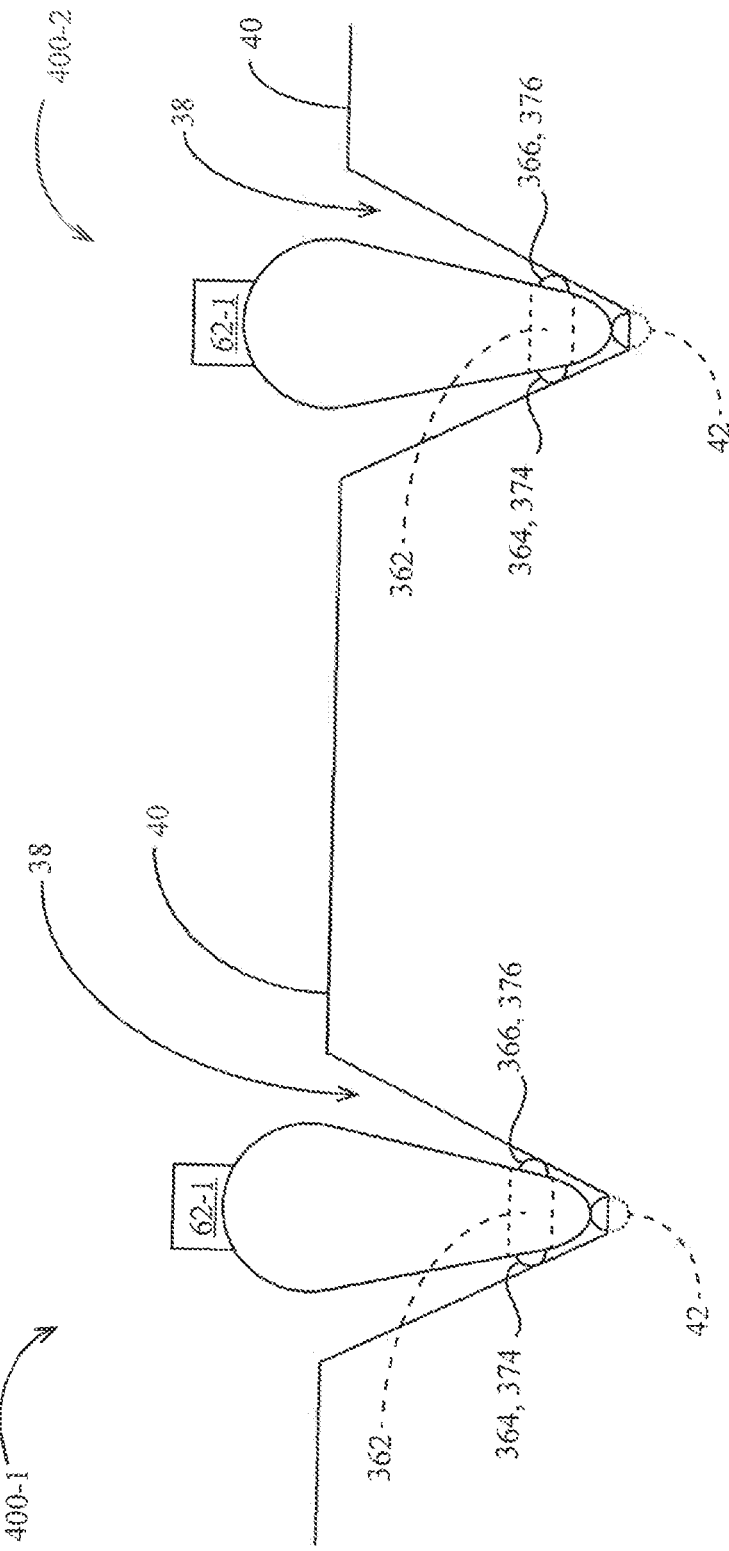
FIG. 4C is a rear elevation view of the seed firmer of FIG. 4A.
Figure 14:
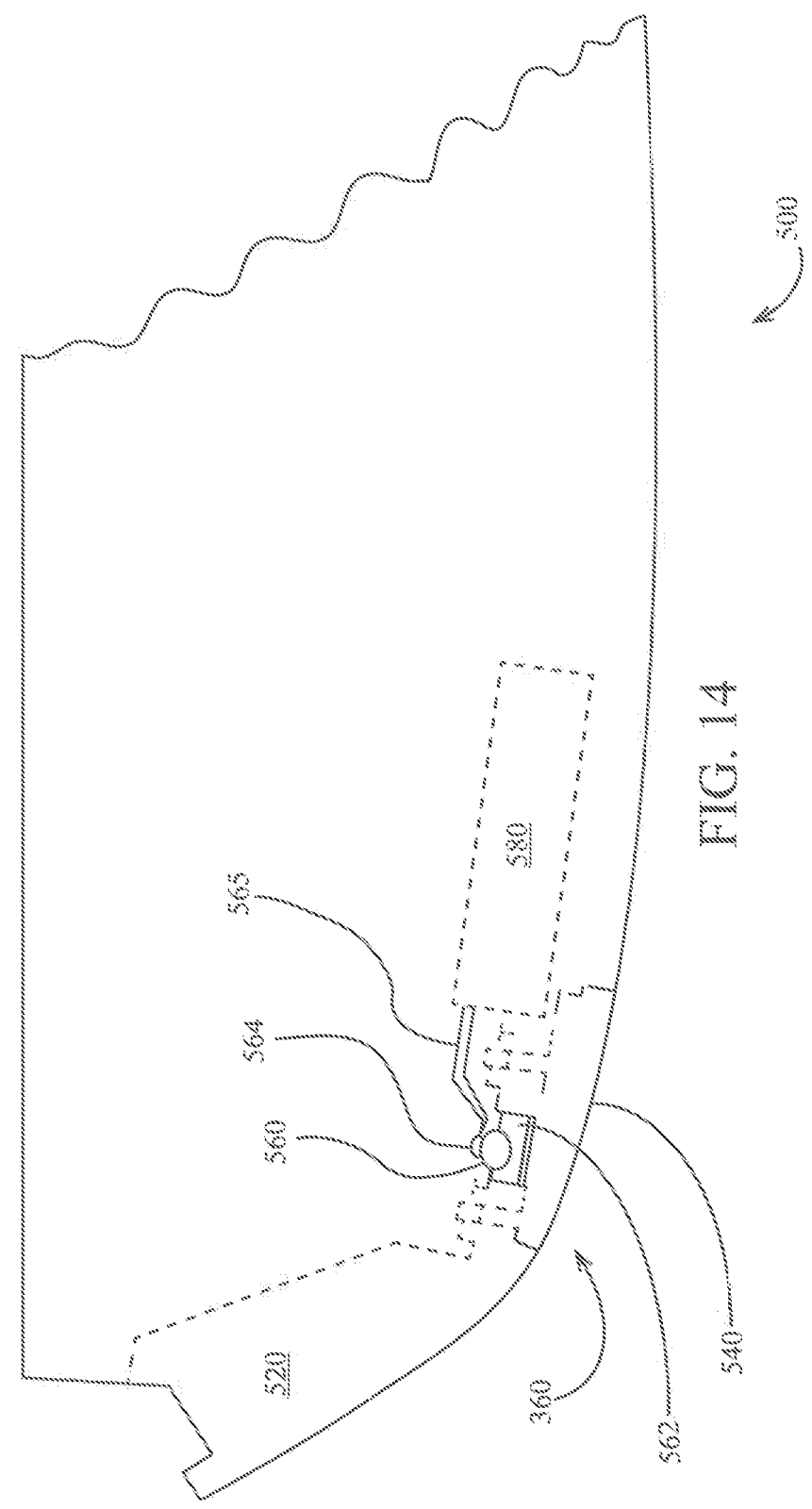
FIG. 14 is an enlarged partial cutaway view of the seed firmer of FIG. 5.

Turning to FIGS. 4A-4C, an embodiment of a seed firmer 400 is illustrated having a plurality of sensors for sensing soil characteristics. The seed firmer 400 preferably includes a flexible portion 410 mounted to the shank 254 and/or the seed tube 232 by a bracket 415. In some embodiments, the bracket 415 is similar to one of the bracket embodiments disclosed in U.S. Pat. No. 6,918,342B2. The seed firmer preferably includes a firmer body 490 disposed and configured to be received at least partially within v-shaped trench 38 and firm seeds 42 into the bottom of the trench. When the seed firmer 400 is lowered into the trench 38, the flexible portion 410 preferably urges the firmer body 490 into resilient engagement with the trench. In some embodiments the flexible portion 410 preferably includes an external or internal reinforcement as disclosed in PCT/US2013/066652. In some embodiments the firmer body 490 includes a removable portion 492; the removable portion 492 preferably slides into locking engagement with the remainder of the firmer body. The firmer body 490 (preferably including the portion of the firmer body engaging the soil, which in some embodiments comprises the removable portion 492) is preferably made of a material (or has an outer surface or coating) having hydrophobic and/or anti-stick properties, e.g. having a Teflon graphite coating and/or comprising a polymer having a hydrophobic material (e.g., silicone oil or polyether-ether-ketone) impregnated therein. Alternatively, the sensors can be disposed on the side of seed firmer 400 (not shown).

Returning to FIGS. 4A through 4C, the seed firmer 400 preferably includes a plurality of reflectivity sensors 350a, 350b. Each reflectivity sensor 350 is preferably disposed and configured to measure reflectivity of soil; in a preferred embodiment, the reflectivity sensor 350 is disposed to measure soil in the trench 38, and preferably at the bottom of the trench. The reflectivity sensor 350 preferably includes a lens disposed in the bottom of the firmer body 490 and disposed to engage the soil at the bottom of the trench 38. In some embodiments the reflectivity sensor 350 comprises one of the embodiments disclosed in U.S. Pat. No. 8,204,689B2 and/or U.S. Provisional Patent Application 61/824,975 ("the '975 application"). In various embodiments, the reflectivity sensor 350 is configured to measure reflectivity in the visible range (e.g., 400 and/or 600 nanometers), in the near-infrared range (e.g., 940 nanometers) and/or elsewhere the infrared range.

The seed firmer 400 may also include a capacitive moisture sensor 351 disposed and configured to measure capacitance moisture of the soil in the seed trench 38, and preferably at the bottom of trench 38.

The seed firmer 400 may also include an electronic tensiometer sensor 352 disposed and configured to measure soil moisture tension of the soil in the seed trench 38, and preferably at the bottom of trench 38.

Alternatively, soil moisture tension can be extrapolated from capacitive moisture measurements or from reflectivity measurements (such as at 1450 nm). This can be done using a soil water characteristic curve based on the soil type.

The seed firmer 400 may also include a temperature sensor 360. The temperature sensor 360 is preferably disposed and configured to measure temperature of soil; in a preferred embodiment, the temperature sensor is disposed to measure soil in the trench 38, preferably at or adjacent the bottom of the trench 38. The temperature sensor 360 preferably includes soil-engaging ears 364, 366 disposed to slidingly engage each side of the trench 38 as the planter traverses the field. The ears 364, 366 preferably engage the trench 38 at or adjacent to the bottom of the trench. The ears 364, 366 are preferably made of a thermally conductive material such as copper. The ears 364 are preferably fixed to and in thermal communication with a central portion 362 housed within the firmer body 490. The central portion 362 preferably comprises a thermally conductive material such as copper; in some embodiments the central portion 362 comprises a hollow copper rod. The central portion 362 is preferably in thermal communication with a thermocouple fixed to the central portion. In other embodiments, the temperature sensor 360 may comprise a non-contact temperature sensor such as an infrared thermometer. In some embodiments, other measurements made by the system 300 (e.g., reflectivity measurements, electrical conductivity measurements, and/or measurements derived from those measurements) are temperature-compensated using the temperature measurement made by the temperature sensor 360. The adjustment of the temperature-compensated measurement based on temperature is preferably carried out by consulting an empirical look-up table relating the temperature-compensated measurement to soil temperature. For example, the reflectivity measurement at a near-infrared wavelength may be increased (or in some examples, reduced) by 1% for every 1 degree Celsius in soil temperature above 10 degrees Celsius.

The seed firmer preferably includes a plurality of electrical conductivity sensors 370r, 370f. Each electrical conductivity sensor 370 is preferably disposed and configured to measure electrical conductivity of soil; in a preferred embodiment, the electrical conductivity sensor is disposed to measure electrical conductivity of soil in the trench 38, preferably at or adjacent the bottom of the trench 38. The electrical conductivity sensor 370 preferably includes soil-engaging ears 374, 376 disposed to slidingly engage each side of the trench 38 as the planter traverses the field. The ears 374, 376 preferably engage the trench 38 at or adjacent to the bottom of the trench. The ears 374, 376 are preferably made of a electrically conductive material such as copper. The ears 374 are preferably fixed to and in electrical communication with a central portion 372 housed within the firmer body 490. The central portion 372 preferably comprises an electrically conductive material such as copper; in some embodiments the central portion 372 comprises a copper rod. The central portion 372 is preferably in electrical communication with an electrical lead fixed to the central portion. The electrical conductivity sensor can measure the electrical conductivity within a trench by measuring the electrical current between soil-engaging ears 374 and 376.

Referring to FIG. 4B, in some embodiments the system 300 measures electrical conductivity of soil adjacent the trench 38 by measuring an electrical potential between the forward electrical conductivity sensor 370*f* and the rearward electrical conductivity sensor 370*f*. In other embodiments, the electrical conductivity sensors 370*f*, 370*r* may be disposed in longitudinally spaced relation on the bottom of the seed firmer in order to measure electrical conductivity at the bottom of the seed trench.

In other embodiments, the electrical conductivity sensors 370 comprise one or more ground-working or ground-contacting devices (e.g., discs or shanks) that contact the soil and are preferably electrically isolated from one another or from another voltage reference. The voltage potential between the sensors 370 or other voltage reference is preferably measured by the system 300. The voltage potential or another electrical conductivity value derived from the voltage potential is preferably and reported to the operator. The electrical conductivity value may also be associated with the GPS-reported position and used to generate a map of the spatial variation in electrical conductivity throughout the field. In some such embodiments, the electrical conductivity sensors may comprise one or more opening discs of a planter row unit, row cleaner wheels of a planter row unit, ground-contacting shanks of a planter, ground-contacting shoes depending from a planter shank, shanks of a tillage tool, or discs of a tillage tool. In some embodiments a first electrical conductivity sensor may comprise a component (e.g., disc or shank) of a first agricultural row unit while a second electrical conductivity sensor comprises a component (e.g., disc or shank) of a second agricultural row unit, such that electrical conductivity of soil extending transversely between the first and second row units is measured. It should be appreciated that at least one of the electrical conductivity sensors described herein is preferably electrically isolated from the other sensor or voltage reference. In one example, the electrical conductivity sensor is mounted to an implement (e.g., to the planter row unit or tillage tool) by being first mounted to an electrically insulating component (e.g., a component made from an electrically insulating material such as polyethylene, polyvinyl chloride, or a rubber-like polymer) which is in turn mounted to the implement.

Referring to FIG. 4C, in some embodiments the system 300 measures electrical conductivity of soil between two row units 200 having a first seed firmer 400-1 and a second seed firmer 400-2, respectively, by measuring an electrical potential between an electrical conductivity sensor on the first seed firmer 400-1 and an electrical conductivity sensor on the second seed firmer 400-2. In some such embodiments, the electrical conductivity sensor 370 may comprise a larger ground-engaging electrode (e.g., a seed firmer housing) comprised of metal or other conductive material. It should be appreciated that any of the electrical conductivity sensors described herein may measure conductivity by any of the following combinations: (1) between a first probe on a ground-engaging row unit component (e.g., on a seed firmer, a row cleaner wheel, an opening disc, a shoe, a shank, a frog, a coulter, or a closing wheel) and a second probe on the same ground-engaging row unit component of the same row unit; (2) between a first probe on a first ground-engaging row unit component (e.g., on a seed firmer, a row cleaner wheel, an opening disc, a shoe, a shank, a frog, a coulter, or a closing wheel) and a second probe on a second ground-engaging row unit component (e.g., on a seed firmer, a row cleaner wheel, an opening disc, a shoe, a shank, a frog, a coulter, or a closing wheel) of the same row unit; or (3) between a first probe on a first ground-engaging row unit component (e.g., on a seed firmer, a row cleaner wheel, an opening disc, a shoe, a shank, a frog, a coulter, or a closing wheel) on a first row unit and a second probe on a second ground-engaging row unit component (e.g., on a seed firmer, a row cleaner wheel, an opening disc, a shoe, a shank, a frog, a coulter, or a closing wheel) on a second row unit. Either or both of the row units described in combinations 1 through 3 above may comprise a planting row unit or another row unit (e.g., a tillage row unit or a dedicated measurement row unit) which may be mounted forward or rearward of the toolbar.

The reflectivity sensors 350, the temperature sensors 360, 360', 360", and the electrical conductivity sensors 370 (collectively, the "firmer-mounted sensors") are preferably in data communication with the monitor 50. In some embodiments, the firmer-mounted sensors are in data communication with the monitor 50 via a transceiver (e.g., a CAN transceiver) and the bus 60. In other embodiments, the firmer-mounted sensors are in data communication with the monitor 50 via wireless transmitter 62-1 (preferably mounted to the seed firmer) and wireless receiver 64. In some embodiments, the firmer-mounted sensors are in electrical communication with the wireless transmitter 62-1 (or the transceiver) via a multi-pin connector comprising a male coupler 472 and a female coupler 474. In firmer body embodiments having a removable portion 492, the male coupler 472 is preferably mounted to the removable portion and the female coupler 474 is preferably mounted to the remainder of the firmer body 190; the couplers 472, 474 are preferably disposed such that the couplers engage electrically as the removable portion is slidingly mounted to the firmer body.

Figure 19A:
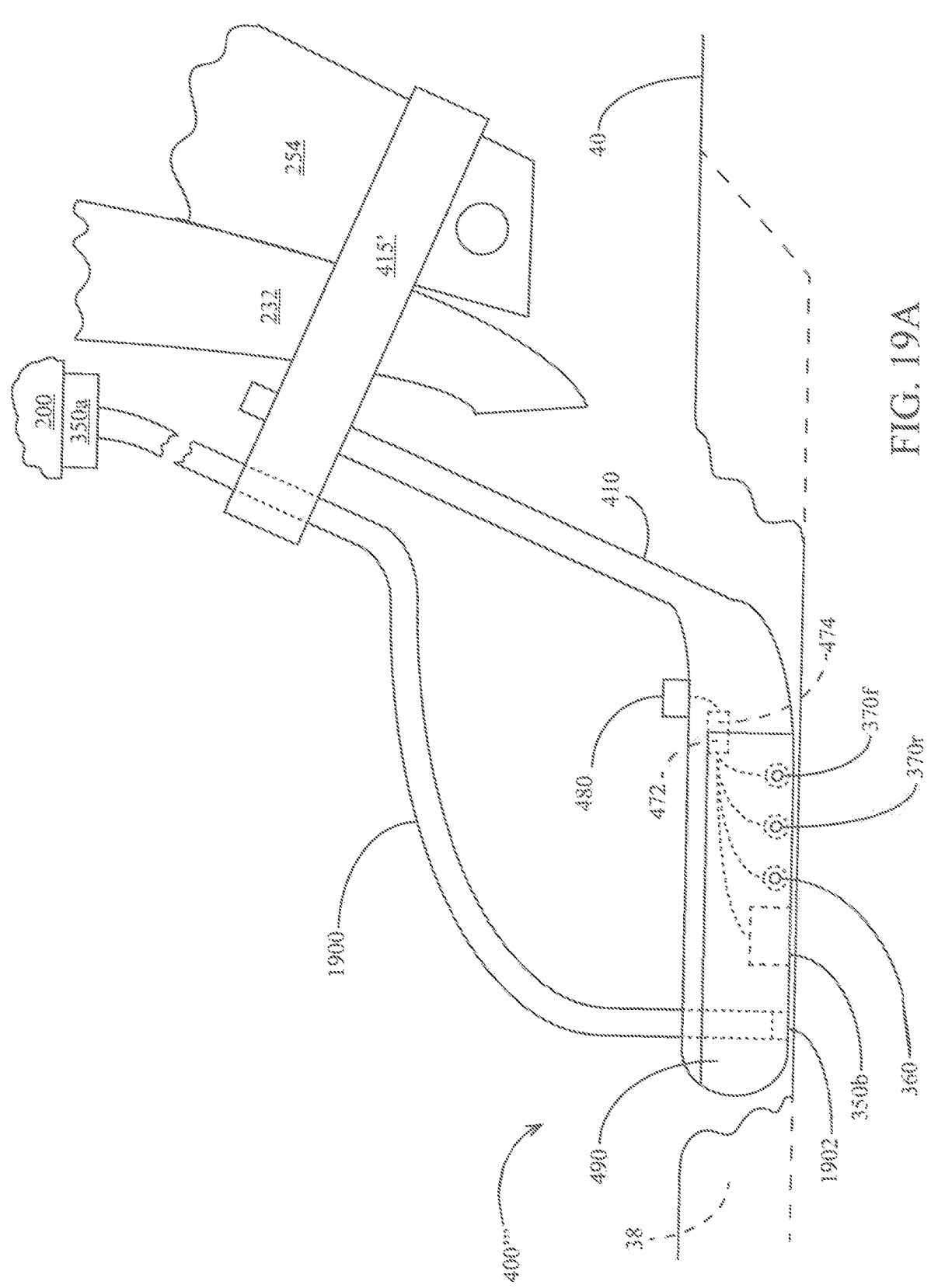
FIG. 19A is a side elevation view of an embodiment of an instrumented seed firmer incorporating fiber-optic cable transmitting light to a reflectivity sensor.
Figure 19B:
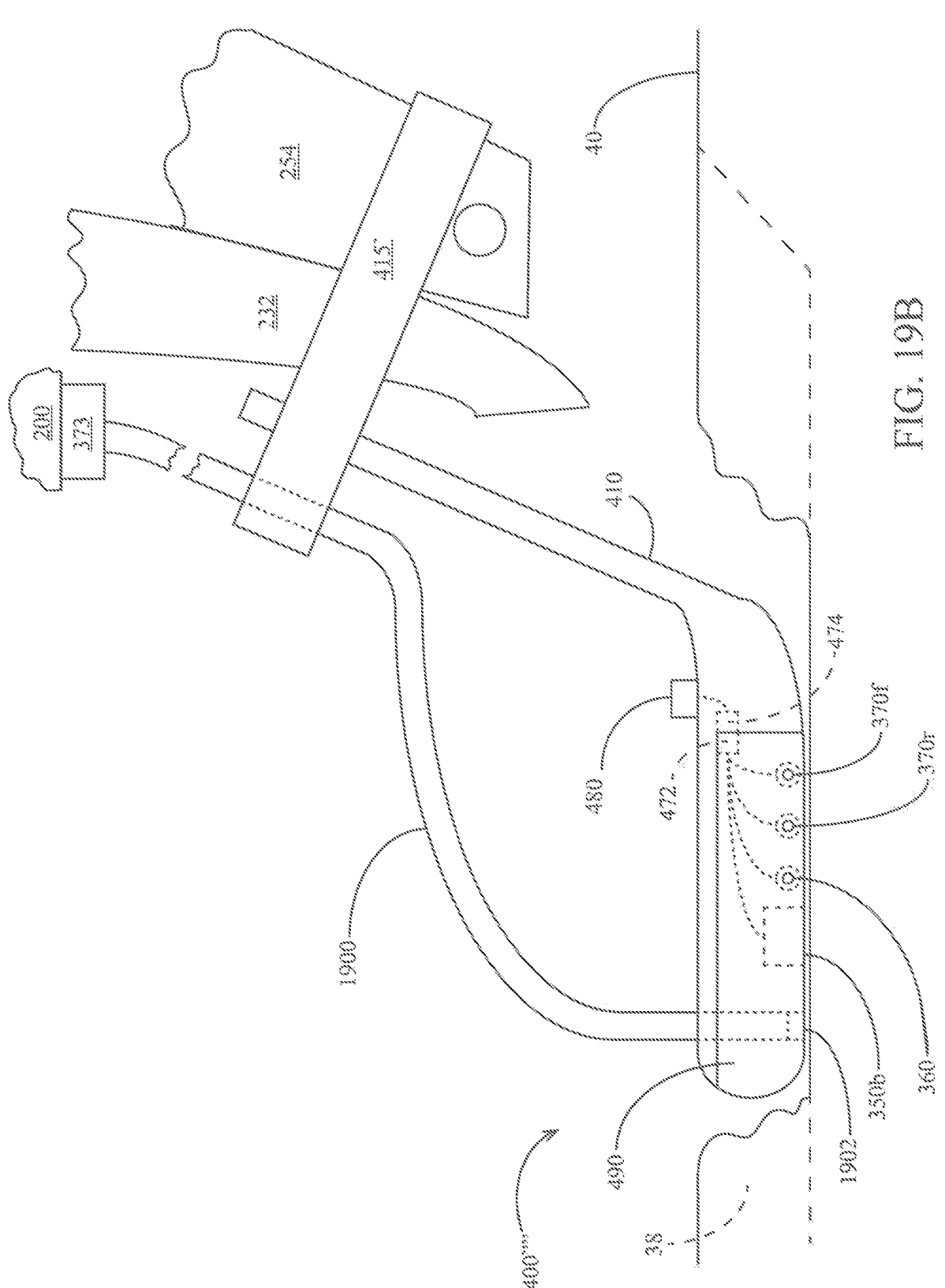
FIG. 19B is a side elevation view of an embodiment of an instrumented seed firmer incorporating fiber-optic cable transmitting light to a spectrometer.

Turning to FIG. 19A, another embodiment of the seed firmer 400''' is illustrated incorporating a fiber-optic cable 1900. The fiber-optic cable 1900 preferably terminates at a lens 1902 in the bottom of the firmer 400'''. The fiber-optic cable 1900 preferably extends to a reflectivity sensor 350*a*, which is preferably mounted separately from the seed firmer, e.g., elsewhere on the row unit 200. In operation, light reflected from the soil (preferably the bottom of trench 28) travels to the reflectivity sensor 350*a* via the fiber-optic cable 1900 such that the reflectivity sensor 350*a* is enabled to measure reflectivity of the soil at a location remote from the seed firmer 400'. In other embodiments such as the seed firmer embodiment 400''' illustrated in FIG. 19B, the fiber-optic cable extends to a spectrometer 373 configured to analyze light transmitted from the soil. The spectrometer 373 is preferably configured to analyze reflectivity at a spectrum of wavelengths. The spectrometer 373 is preferably in data communication with the monitor 50. The spectrometer 373 preferably comprises a fiber-optic spectrometer such as model no. USB4000 available from Ocean Optics, Inc. in Dunedin, Florida. In the embodiments 400''' and 400'''', a modified firmer bracket 415' is preferably configured to secure the fiber-optic cable 1900.

Figure 25:
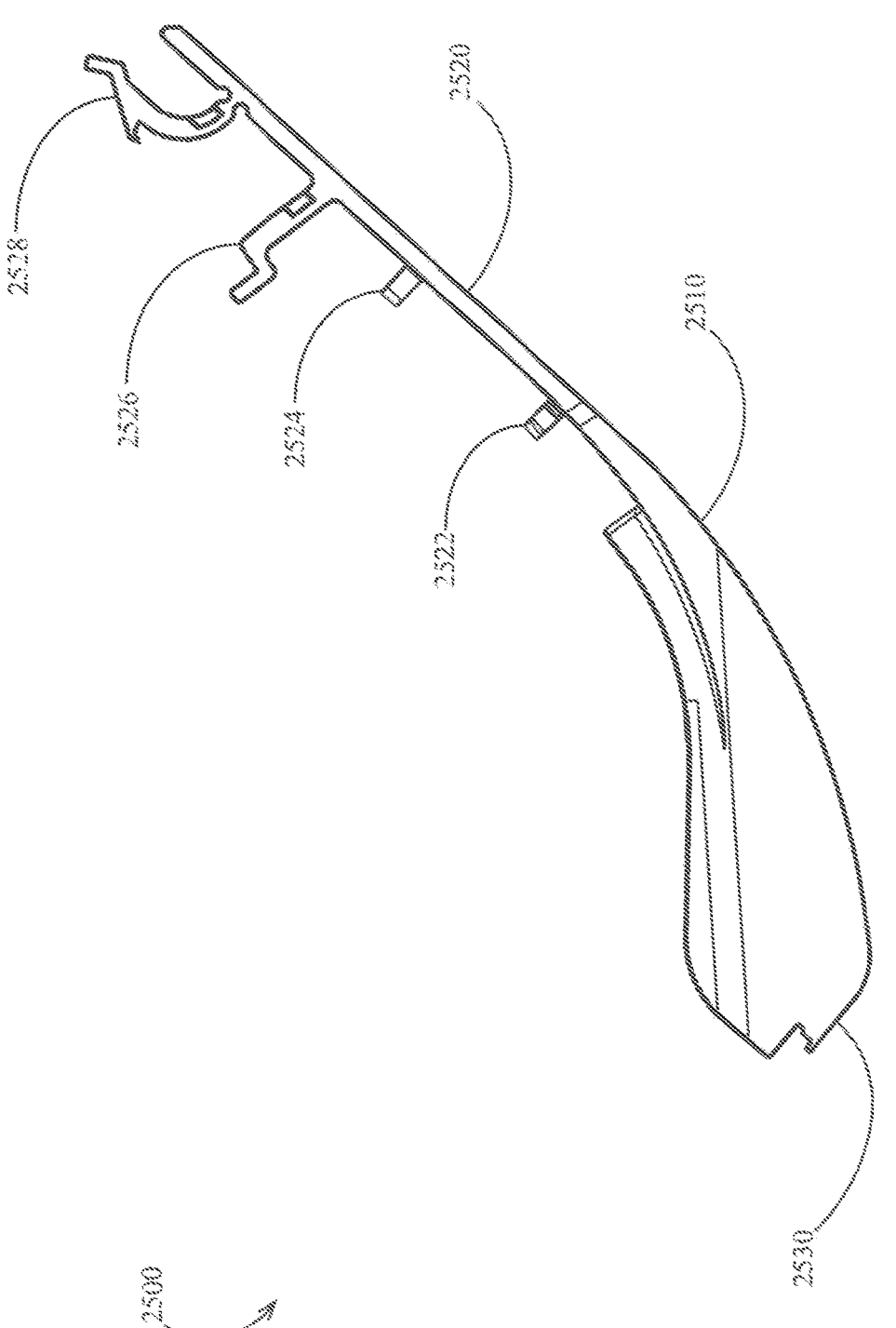
FIG. 25 is a side elevation view of another embodiment of a seed firmer.
Figure 26:
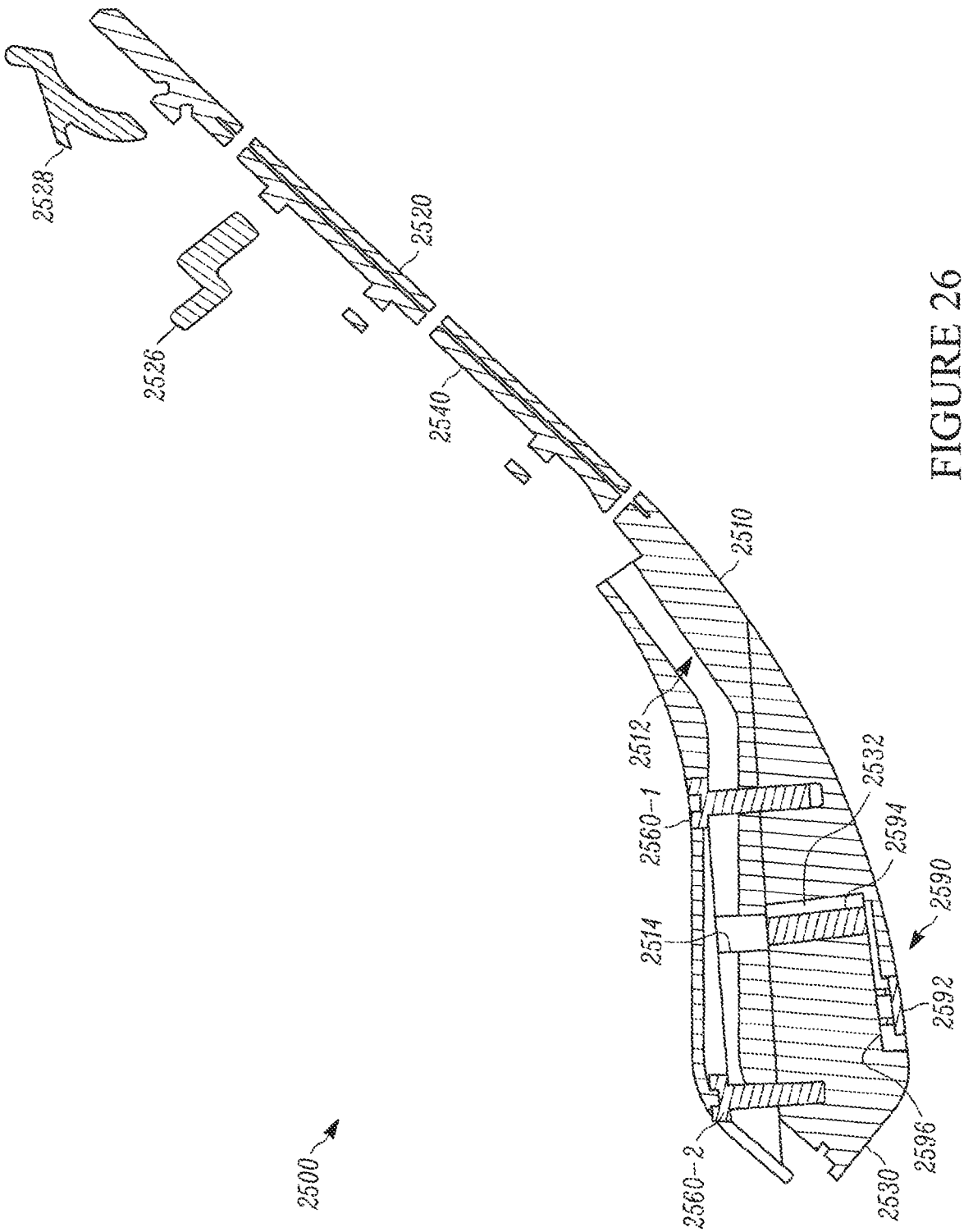
FIG. 26 is a side cross-sectional view of the seed firmer of FIG. 25.

Turning to FIGS. 25-26, another firmer embodiment 2500 is illustrated. The firmer 2500 includes an upper portion 2510 having a mounting portion 2520. The mounting portion 2520 is preferably stiffened by inclusion of a stiffening insert made of stiffer material than the mounting portion (e.g., the mounting portion may be made of plastic and the stiffening insert may be made of metal) in an inner cavity 2540 of the mounting portion 2520. The mounting portion 2520 preferably includes mounting tabs 2526, 2528 for releasably attaching the firmer 2500 to a bracket on the row unit. The mounting portion 2520 preferably includes mounting hooks 2522, 2524 for attaching a liquid application conduit (e.g., flexible tube) (not shown) to the firmer 2500. The upper portion 2510 preferably includes an internal cavity 2512 sized to receive the liquid application conduit. The internal cavity 2512 preferably includes a rearward aperture through which the liquid application conduit extends for dispensing liquid behind the firmer 2500. It should be appreciated that a plurality of liquid conduits may be inserted in the internal cavity 2512; additionally, a nozzle may be included at a terminal end of the conduit or conduits to redirect and/or split the flow of liquid applied in the trench behind the firmer 2500.

The firmer 2500 also preferably includes a ground-engaging portion 2530 mounted to the upper portion 2510. The ground-engaging portion 2530 may be removably mounted to the upper portion 2510; as illustrated, the ground-engaging portion is mounted to the upper portion by threaded screws 2560, but in other embodiments the ground-engaging portion may be installed and removed without the use of tools, e.g. by a slot-and-groove arrangement. The ground-engaging portion 2530 may also be permanently mounted to the upper portion 2510, e.g., by using rivets instead of screws 2560, or by molding the upper portion to the ground-engaging portion. The ground-engaging portion 2530 is preferably made of a material having greater wear-resistance than plastic such as metal (e.g., stainless steel, cobalt steel, or hardened white iron), may include a wear-resistant coating (or a non-stick coating as described herein), and may include a wear-resistant portion such as a tungsten carbide insert.

The ground-engaging portion 2530 preferably includes a sensor for detecting characteristics of the trench (e.g., soil moisture, soil organic matter, soil temperature, seed presence, seed spacing, percentage of seeds firmed, soil residue presence) such as a reflectivity sensor 2590, preferably housed in a cavity 2532 of the ground-engaging portion. The reflectivity sensor preferably includes a sensor circuit board 2596 having a sensor disposed to receive reflected light from the trench through a transparent window 2592. The transparent window 2592 is preferably mounted flush with a lower surface of the ground-engaging portion such that soil flows underneath the window without building up over the window or along an edge thereof. An electrical connection 2594 preferably connects the sensor circuit board 2596 to a wire or bus (not shown) placing the sensor circuit board in data communication with the monitor 50.

Turning to FIGS. 5-14, another seed firmer embodiment 500 is illustrated. A flexible portion 504 is preferably configured to resiliently press a firmer body 520 into the seed trench 38. Mounting tabs 514, 515 releasably couple the flexible portion 504 to the firmer bracket 415, preferably as described in the '585 application.

A flexible liquid conduit 506 preferably conducts liquid (e.g., liquid fertilizer) from a container to an outlet 507 for depositing in or adjacent to the trench 38. The conduit 506 preferably extends through the firmer body 520 between the outlet 507 and a fitting 529 which preferably constrains the conduit 506 from sliding relative to the firmer body 520. The portion of the conduit may extend through an aperture formed in the firmer body 520 or (as illustrated) through a channel covered by a removable cap 530. The cap 530 preferably engages sidewalls 522, 524 of the firmer body 520 by hooked tabs 532. Hooked tabs 532 preferably retain sidewalls 522, 524 from warping outward in addition to retaining the cap 530 on the firmer body 520. A screw 533 also preferably retains the cap 530 on the firmer body 520.

The conduit 506 is preferably retained to the flexible portion 504 of the seed firmer 500 by mounting hooks 508, 509 and by the mounting tabs 514, 515. The conduit 506 is preferably resiliently grasped by arms 512, 513 of the mounting hooks 508, 509 respectively. The conduit 506 is preferably received in slots 516, 517 of mounting tabs 514, 515, respectively.

A harness 505 preferably comprises a wire or plurality of wires in electrical communication with the firmer-mounted sensors described below. The harness is preferably received in slots 510, 511 of the mounting hooks 508, 509 and additionally retained in place by the conduit 506. The harness 505 is preferably grasped by slots 518, 519 of the mounting tabs 514, 515, respectively; the harness 505 is preferably pressed through a resilient opening of each slot 518, 519 and the resilient opening returns into place so that the slots retain the harness 505 unless the harness is forcibly removed.

In some embodiments the lowermost trench-engaging portion of the seed firmer 500 comprises a plate 540. The plate 540 may comprise a different material and/or a material having different properties from the remainder of the firmer body 520; for example, the plate 540 may have a greater hardness than the remainder of the firmer body 520 and may comprise powder metal. In some embodiments, the entire firmer body 520 is made of a relatively hard material such as powder metal. In an installment phase, the plate 540 is mounted to the remainder of the firmer body 520, e.g., by rods 592 fixed to plate 540 and secured to the remainder of the firmer body by snap rings 594; it should be appreciated that the plate may be either removably mounted or permanently mounted to the remainder of the firmer body.

The seed firmer 500 is preferably configured to removably receive a reflectivity sensor 350 within a cavity 527 within the firmer body 520. In a preferred embodiment, the reflectivity sensor 350 is removably installed in the seed firmer 500 by sliding the reflectivity sensor 350 into the cavity 527 until flexible tabs 525, 523 snap into place, securing the reflectivity sensor 350 in place until the flexible tabs are bent out of the way for removal of the reflectivity sensor. The reflectivity sensor 350 may be configured to perform any of the measurements described above with respect to the reflectivity sensor of seed firmer 400. The reflectivity sensor 350 preferably comprises a circuit board 580 (in some embodiments an over-molded printed circuit board). The reflectivity sensor 350 preferably detects light transmitted through a lens 550 having a lower surface coextensive with the surrounding lower surface of the firmer body 550 such that soil and seeds are not dragged by the lens. In embodiments having a plate 540, the bottom surface of the lens 550 is preferably coextensive with a bottom surface of the plate 540. The lens 550 is preferably a transparent material such as sapphire. The interface between the circuit board 580 and the lens 550 is preferably protected from dust and debris; in the illustrated embodiment the interface is protected by an o-ring 552, while in other embodiments the interface is protected by a potting compound. In a preferred embodiment, the lens 550 is mounted to the circuit board 580 and the lens slides into place within the lowermost surface of the firmer body 520 (and/or the plate 540) when the reflectivity sensor 350 is installed. In such embodiments, the flexible tabs 523, 525 preferably lock the reflectivity sensor into a position wherein the lens 550 is coextensive with the lowermost surface of the firmer body 520.

The seed firmer 500 preferably includes a temperature sensor 360. The temperature sensor 360 preferably comprises a probe 560. The probe 560 preferably comprises a thermo-conductive rod (e.g., a copper rod) extending through the width of the firmer body 500 and having opposing ends extending from the firmer body 500 to contact either side of the trench 38. The temperature sensor 360 preferably also comprises a resistance temperature detector ("RTD") 564 fixed to (e.g., screwed into a threaded hole in) the probe 560; the RTD is preferably in electrical communication with the circuit board 580 via an electrical lead 565; the circuit board 580 is preferably configured to process both reflectivity and temperature measurements and is preferably in electrical communication with the harness 505. In embodiments in which the plate 540 and/or the remainder of the firmer body 520 comprise a thermally conductive material, an insulating material 562 preferably supports the probe 560 such that temperature changes in the probe are minimally affected by contact with the firmer body; in such embodiments the probe 560 is preferably primarily surrounded by air in the interior of the firmer body 520 and the insulating material 562 (or firmer body) preferably contacts a minimal surface area of the probe. In some embodiments the insulating material comprises a low-conductivity plastic such as polystyrene or polypropylene.

Figure 15:
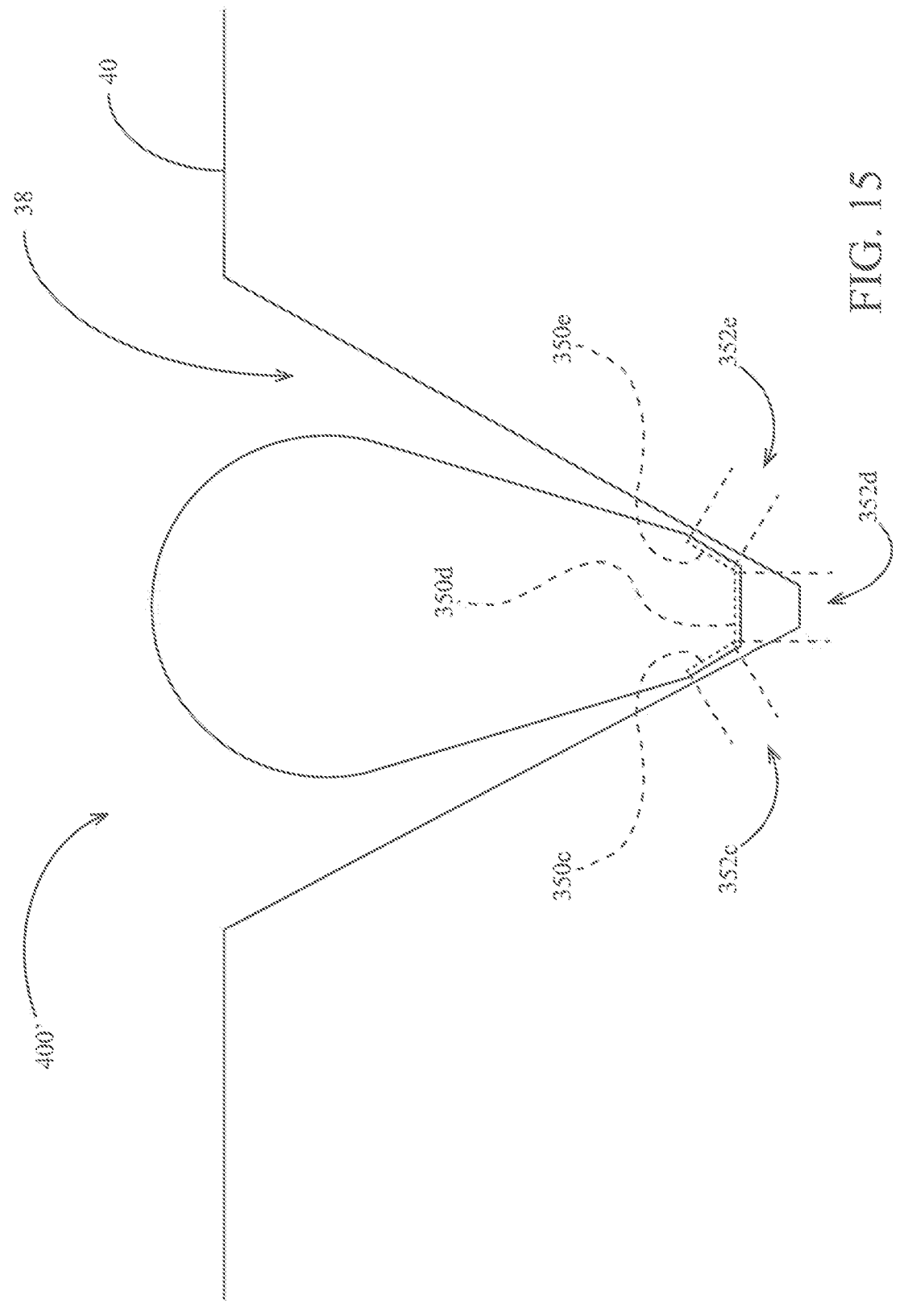
FIG. 15 is a rear view of another embodiment of a seed firmer.

Turning to FIG. 15, another embodiment 400′ of the seed firmer is illustrated having a plurality of reflectivity sensors 350. Reflectivity sensors 350c, 350d and 350e are disposed to measure reflectivity of regions 352c, 352d and 352e, respectively, at and adjacent to the bottom of the trench 38. The regions 352c, 352d and 352e preferably constitute a substantially contiguous region preferably including all or substantially the entire portion of the trench in which seed rests after falling into the trench by gravity. In other embodiments, a plurality of temperature and/or electrical conductivity sensors are disposed to measure a larger, preferably substantially contiguous region.

Figure 16:
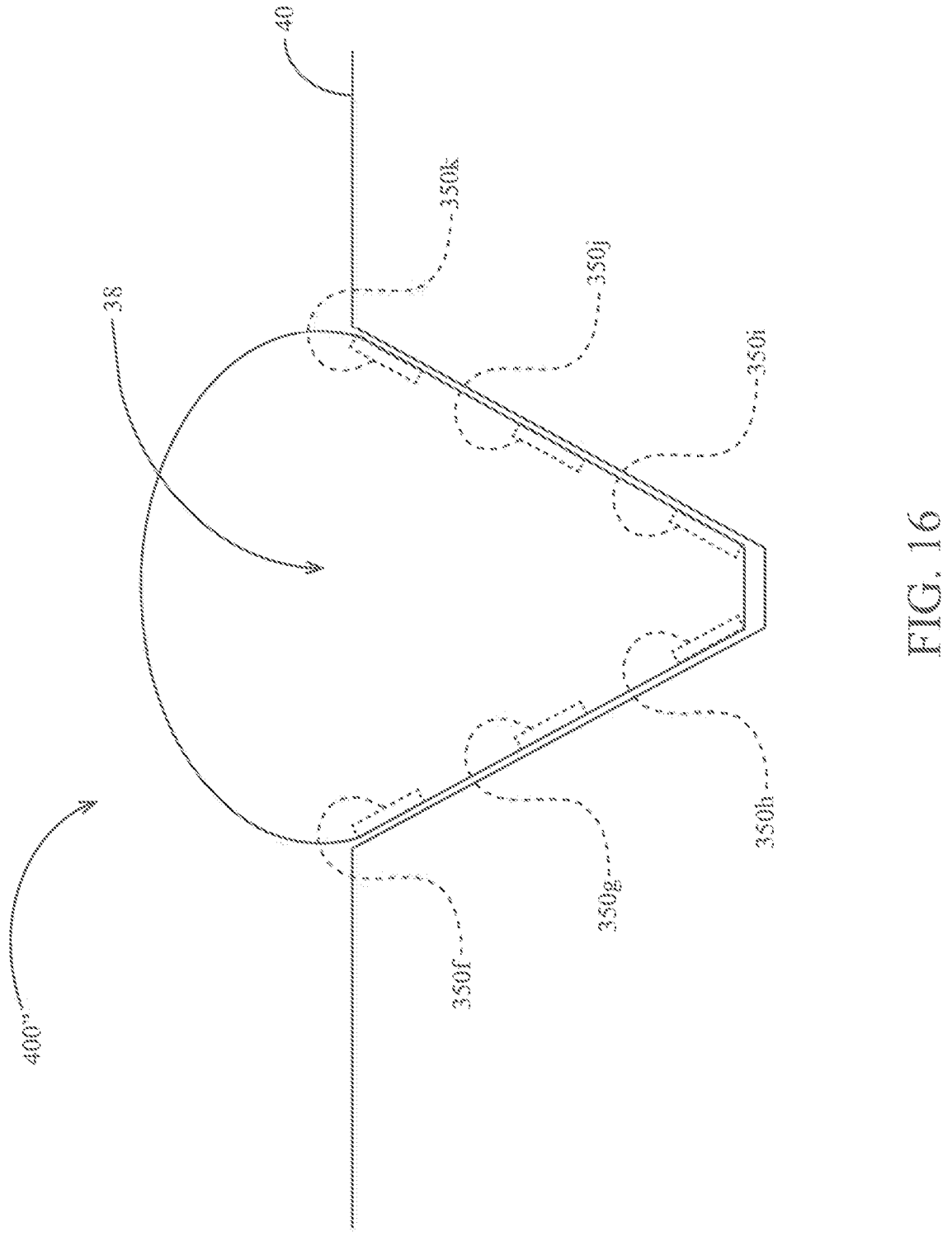
FIG. 16 is a rear view of still another embodiment of a seed firmer.

Turning to FIG. 16, another embodiment of a seed firmer 400″ is illustrated having a plurality of reflectivity sensors 350 disposed to measure at either side of the trench 38 at various depths within in the trench. The reflectivity sensors 350f, 350k are disposed to measure reflectivity at or adjacent to the top of the trench 38. The reflectivity sensors 350h, 350i are disposed to measure reflectivity at or adjacent to the bottom of the trench 38. The reflectivity sensors 350g, 350j are disposed to measure reflectivity at an intermediate depth of the trench 38, e.g., at half the depth of the trench. It should be appreciated that in order to effectively make soil measurements at a depth at an intermediate depth of the trench, it is desirable to modify the shape of the seed firmer such that the sidewalls of the seed firmer engage the sides of the trench at an intermediate trench depth. Likewise, it should be appreciated that in order to effectively make soil measurements at a depth near the top of the trench (i.e., at or near the soil surface 40), it is desirable to modify the shape of the seed firmer such that the sidewalls of the seed firmer engage the sides of the trench at or near the top of the trench. In other embodiments, a plurality of temperature and/or electrical conductivity sensors are disposed to measure temperature and/or electrical conductivity, respectively, of soil at a plurality of depths within the trench 38.

Figure 18:
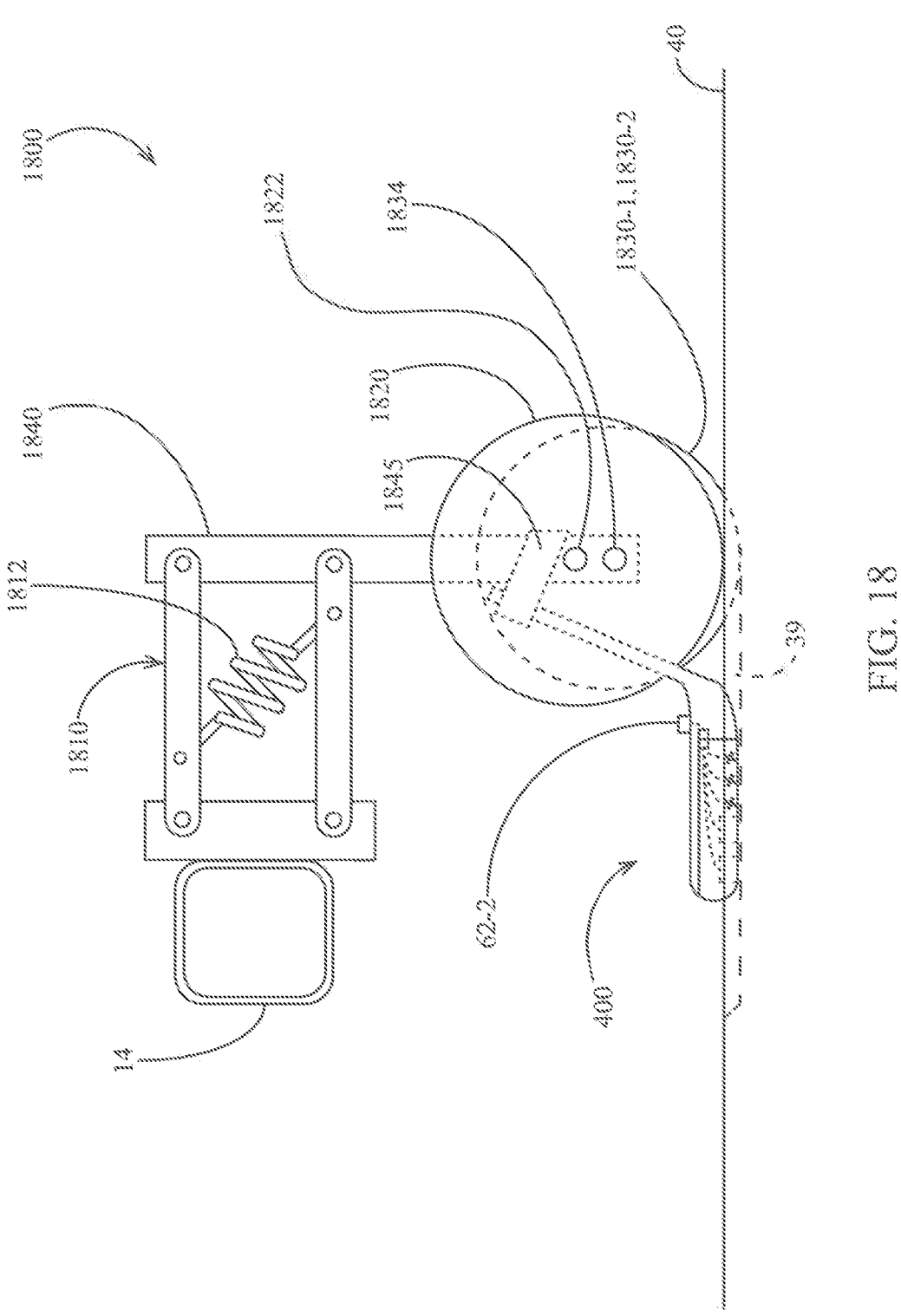
FIG. 18 is a side elevation view of an embodiment of a reference sensor.

As described above with respect to the system 300, in some embodiments a second set of reflectivity sensors 350, temperature sensors 360, and electrical conductivity sensors 370 are mounted to a reference sensor assembly 1800. One such embodiment is illustrated in FIG. 18, in which the reference sensor assembly opens a trench 39 in which a seed firmer 400 having firmer-mounted sensors is resiliently engaged in order to sense the soil characteristics of the bottom of the trench 39. The trench 39 is preferably at a shallow depth (e.g., between ⅛ and ½ inch) or at a deep depth (e.g., between 3 and 5 inches). The trench is preferably opened by a pair of opening discs 1830-1, 1830-2 disposed to open a v-shaped trench in the soil 40 and rotating about lower hubs 1834. The depth of the trench is preferably set by one or more gauge wheels 1820 rotating about upper hubs 1822. The upper and lower hubs are preferably fixedly mounted to a shank 1840. The seed firmer is preferably mounted to the shank 1840 by a firmer bracket 1845. The shank 1840 is preferably mounted to the toolbar 14. In some embodiments, the shank 1840 is mounted to the toolbar 14 by a parallel arm arrangement 1810 for vertical movement relative to the toolbar; in some such embodiments, the shank is resiliently biased toward the soil by an adjustable spring 1812 (or other downforce applicator). In the illustrated embodiment the shank 1840 is mounted forward of the toolbar 14; in other embodiments, the shank may be mounted rearward of the toolbar 14. In other embodiments, the firmer 400 may be mounted to the row unit shank 254, to a closing wheel assembly, or to a row cleaner assembly.

Figure 23:
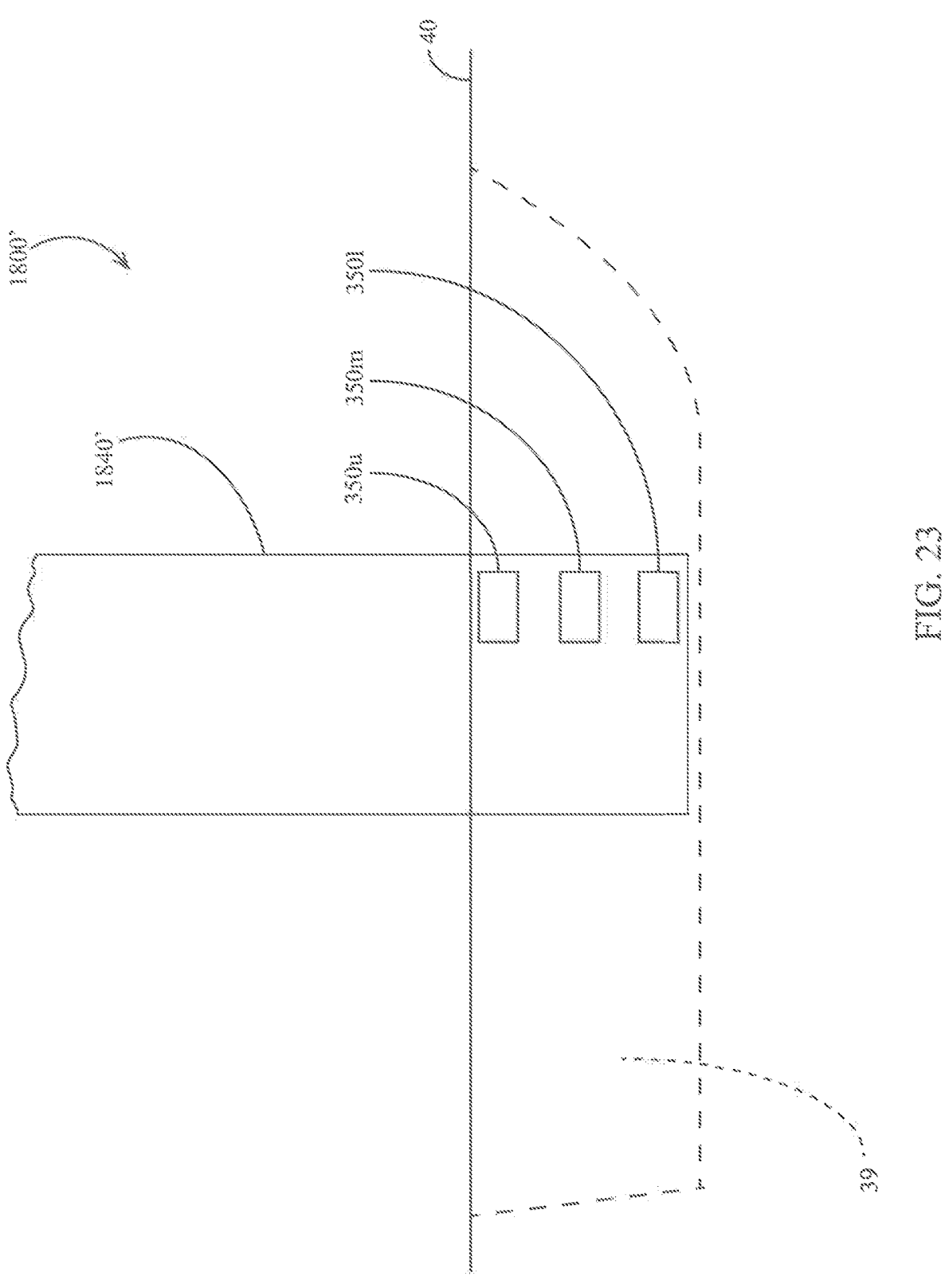
FIG. 23 is a side elevation view of another embodiment of a reference sensor having an instrumented shank.
Figure 24:
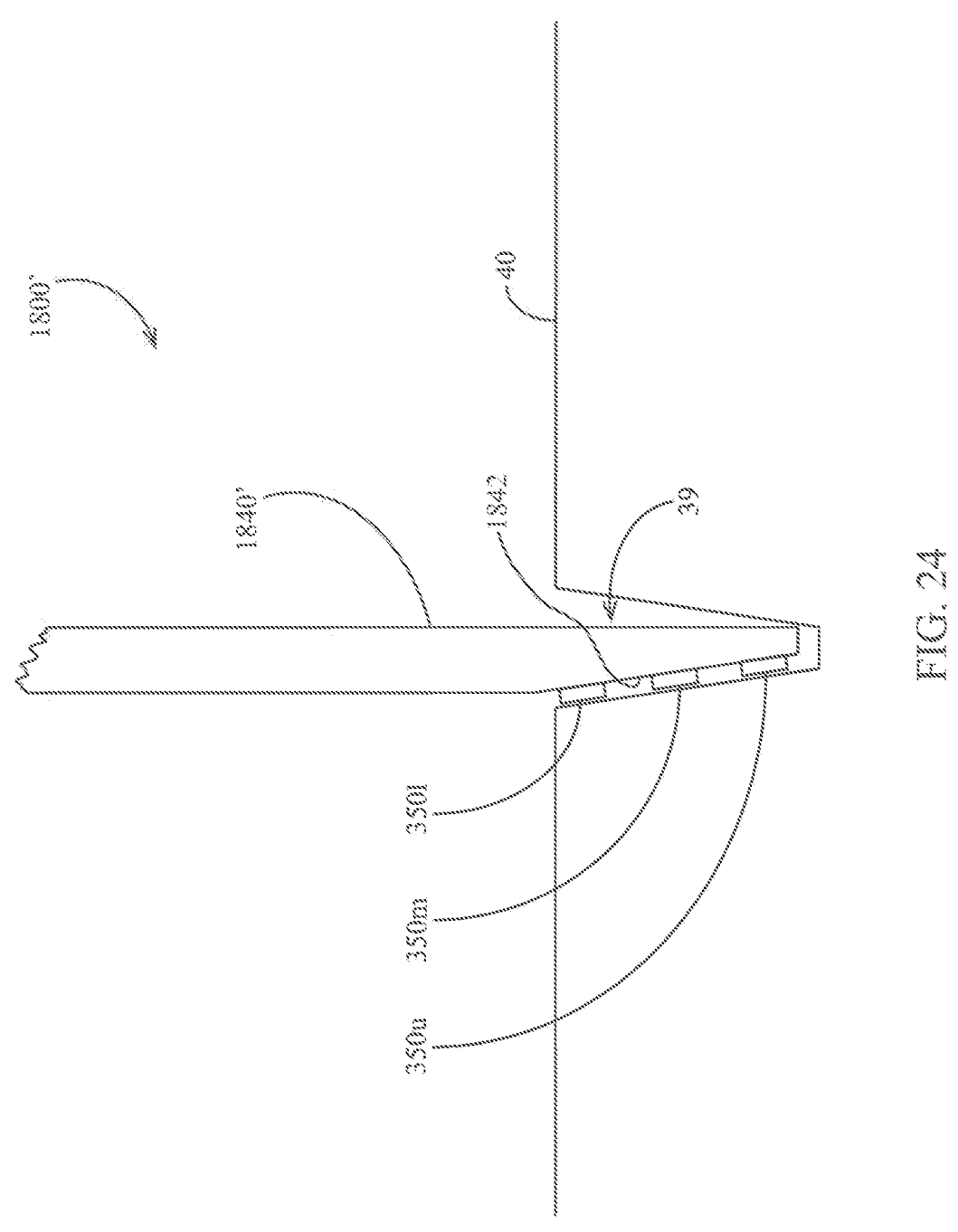
FIG. 24 is a front elevation view of the reference sensor of FIG. 23.

An embodiment of the reference sensor 1800′ including an instrumented shank 1840′ is illustrated in FIGS. 23 and 24. Reference sensors 350u, 350m, 350l, are preferably disposed on a lower end of the shank 1840 and disposed to contact soil on a sidewall of the trench 39 at or adjacent the top of the trench, at an intermediate trench depth, and at or adjacent the bottom of the trench, respectively. The shank 1840 extends into the trench and preferably includes an angled surface 1842 to which the reference sensors 350 are mounted; the angle of surface 1842 is preferably parallel to the sidewall of the trench 39.

It should be appreciated that the sensor embodiment of FIGS. 4A-4C may be mounted to and used in conjunction with equipment other than seed planters such as tillage tools. For example, the seed firmer could be disposed to contact soil in a trench opened by (or soil surface otherwise passed over by) a tillage implement such as a disc harrow or soil ripper. On such equipment, the sensors could be mounted on a part of the equipment that contacts soil or on any extension that is connected to a part of the equipment and contacts soil. It should be appreciated that in some such embodiments, the seed firmer would not contact planted seed but would still measure and report soil characteristics as otherwise disclosed herein.

Figures 27A, 27B:
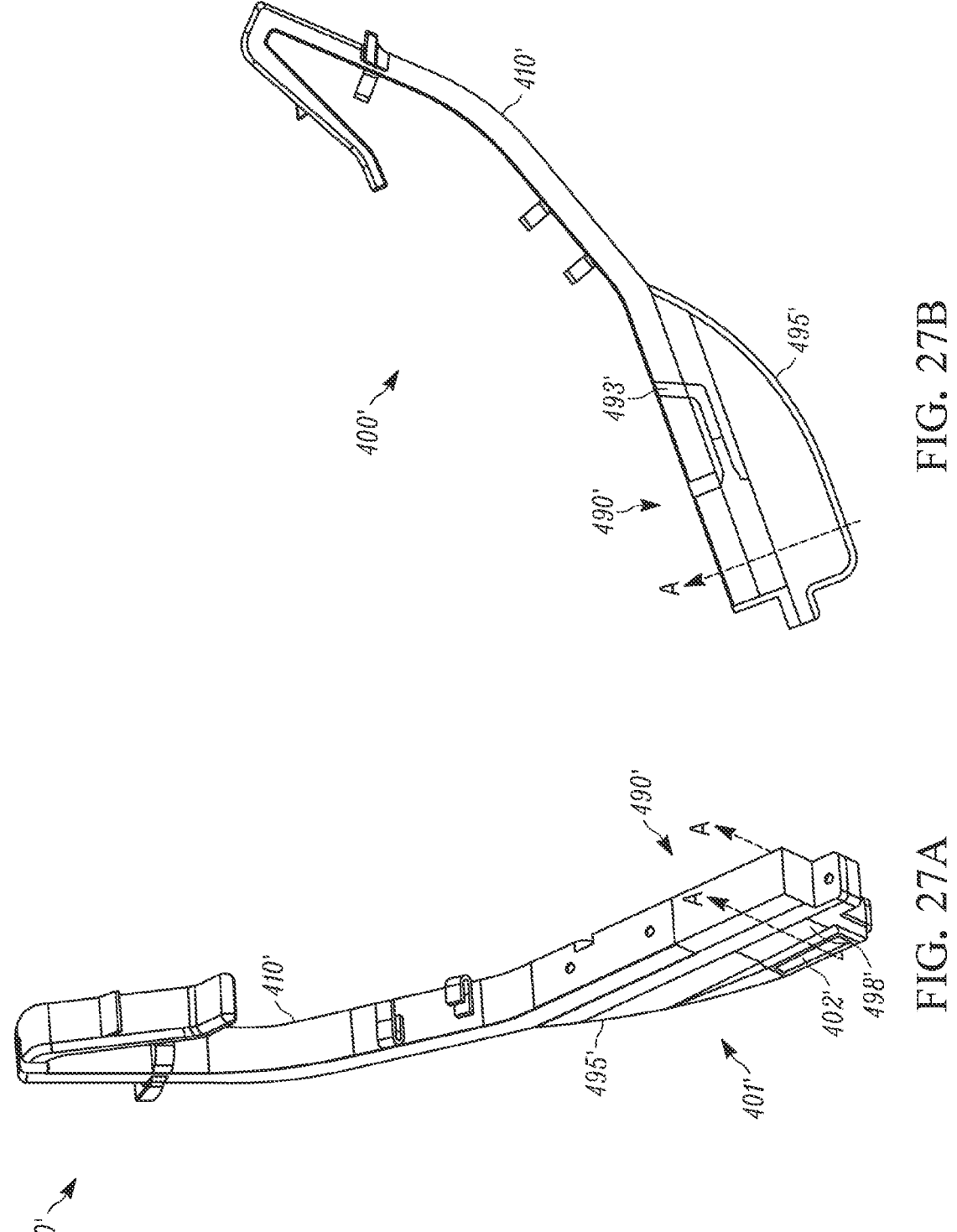
FIG. 27A is a perspective view of a seed firmer according to one embodiment.
FIG. 27B is a side view of the seed firmer of FIG. 27A.

In another embodiment, any of the sensors (reflectivity sensor 350, temperature sensor 360, electrical conductivity sensor 370, capacitive moisture sensor 351, and electronic tensiometer sensor 352) can be disposed in seed firmer 400′ with an exposure through a side of seed firmer 400′. As illustrated in FIG. 27A in one embodiment, seed firmer 400′ has a protrusion 401′ from a side of seed firmer 400′ through which the sensors sense. Disposed in protrusion 401′ is a lens 402′. Having protrusion 401′ minimizes any buildup that blocks lens 402′, and lens 402′ can stay in contact with the soil.

Figure 28A:
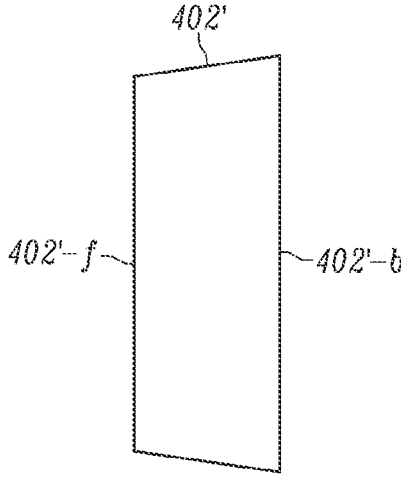
FIG. 28A is a side view of a lens according to one embodiment.
Figure 28B:
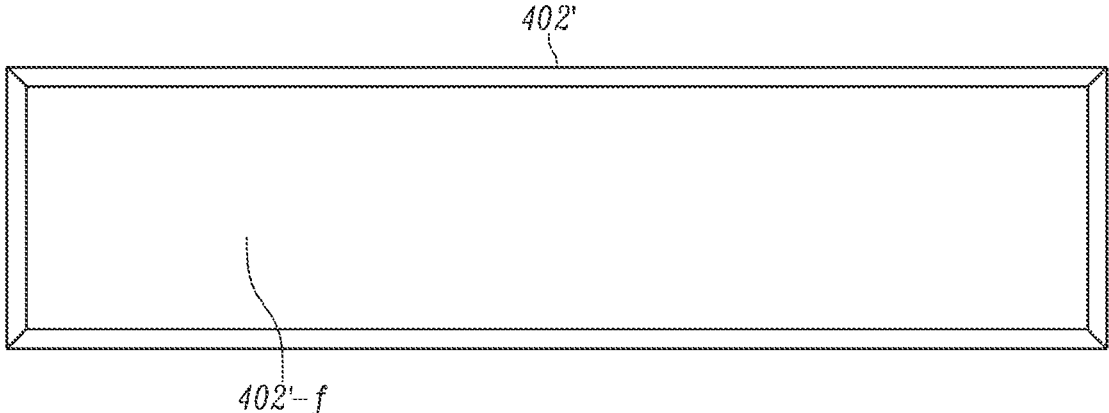
FIG. 28B is a front view of the lens of FIG. 28A.

Lens 402′ can be made from any material that is durable to the abrasion caused by soil contact and transparent to the wavelengths of light used. In certain embodiment, the material has a Mohs hardness of at least 8. In certain embodiments, the material is sapphire, ruby, diamond, moissanite (SiC), or toughened glass (such as Gorilla™ glass). In one embodiment, the material is sapphire. In one embodiment as illustrated in FIGS. 28A and 28B, lens 402′ is a trapezoidal shape with sides sloped from the back 402′-b to the front 402′-f of lens 402′. In this embodiment, lens 402′ can sit within protrusion 401′ with no retainers against the back 402′-b of lens 402′. Sensors that are disposed behind lens 402′ are then not obstructed by any such retainers. Alternatively, lens 402′ can be disposed the opposite to the previous embodiment with the sides sloped from the front 402-f to the back 402-b.

Figure 29A:
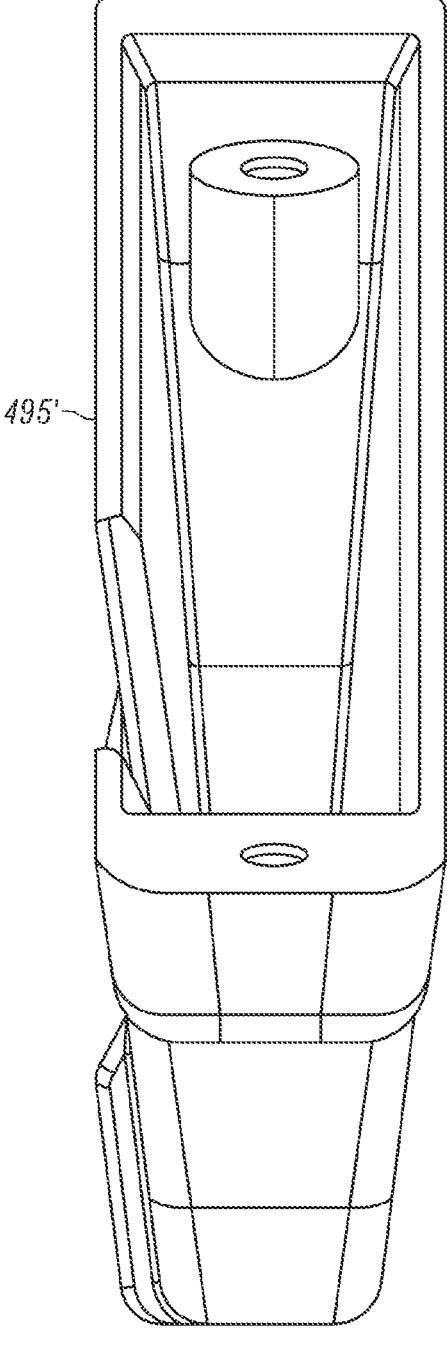
FIG. 29A is a perspective view of a firmer base according to one embodiment.
Figure 29B:
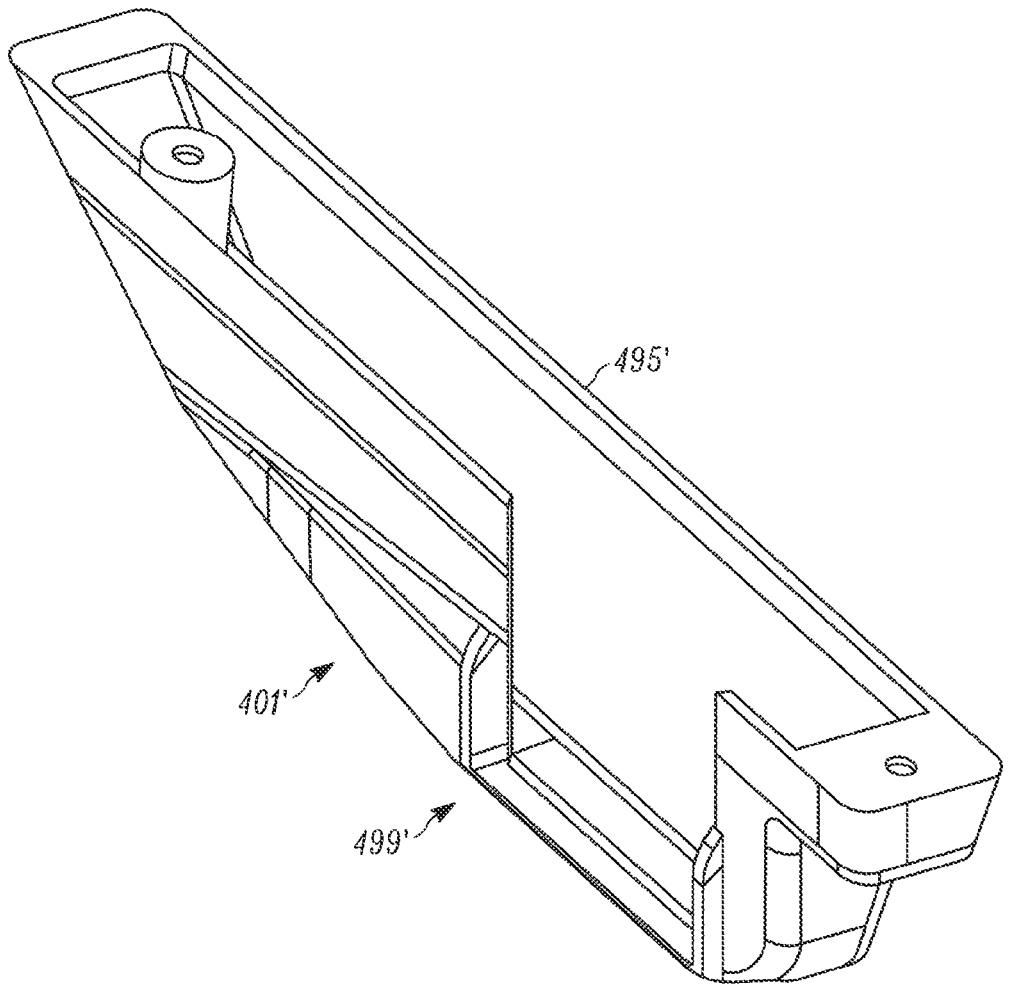
FIG. 29B is a side perspective view of the firmer base of FIG. 29A.
Figure 29C:
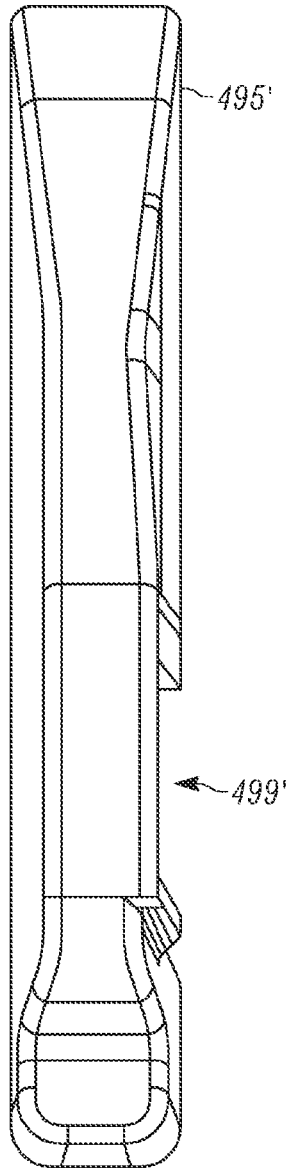
FIG. 29C is a bottom view of the firmer base of FIG. 29A.
Figure 30A:
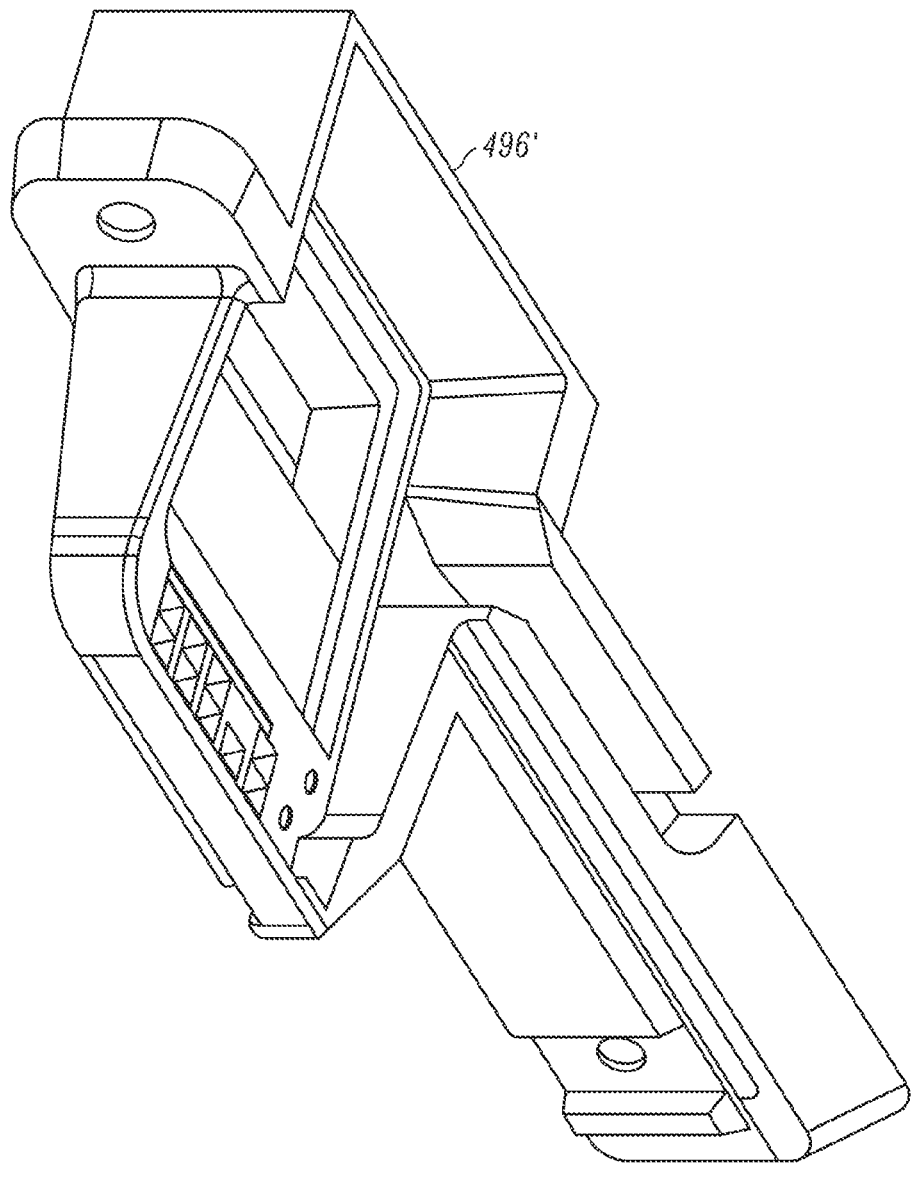
FIG. 30A is a perspective view of a sensor housing according to one embodiment.
Figure 30B:
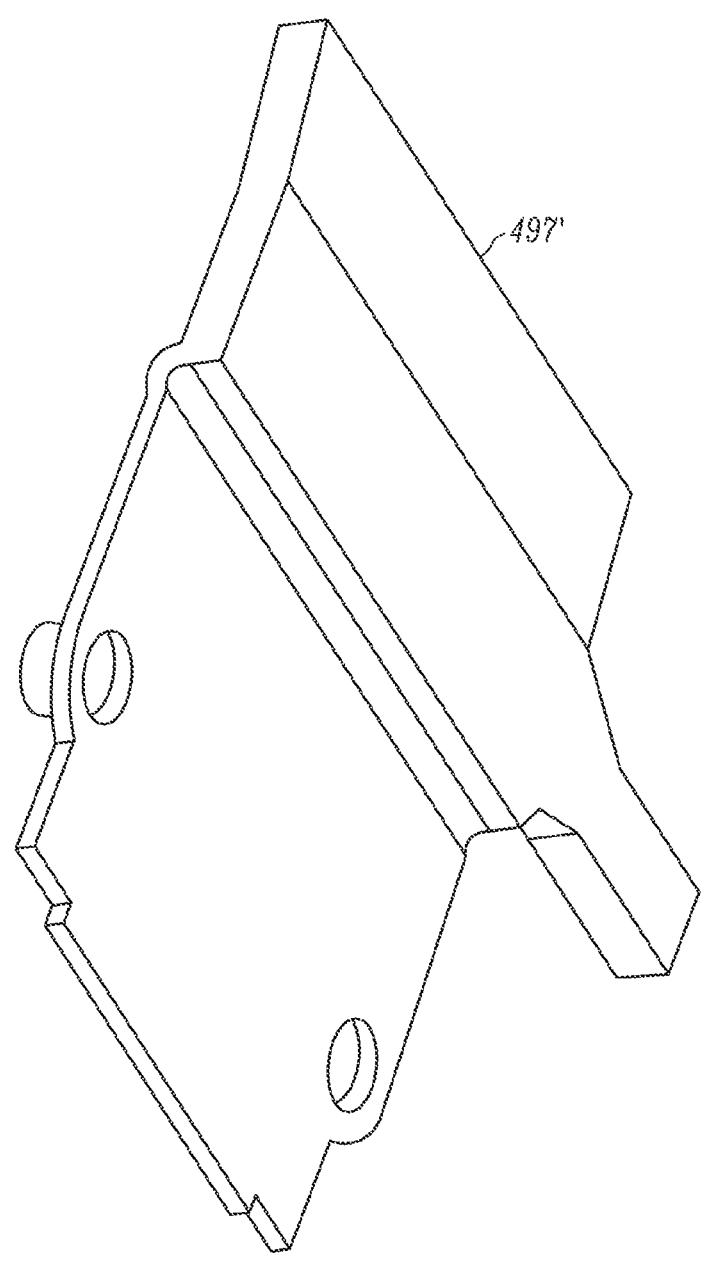
FIG. 30B is a perspective view of a cover according to one embodiment.
Figure 31B:
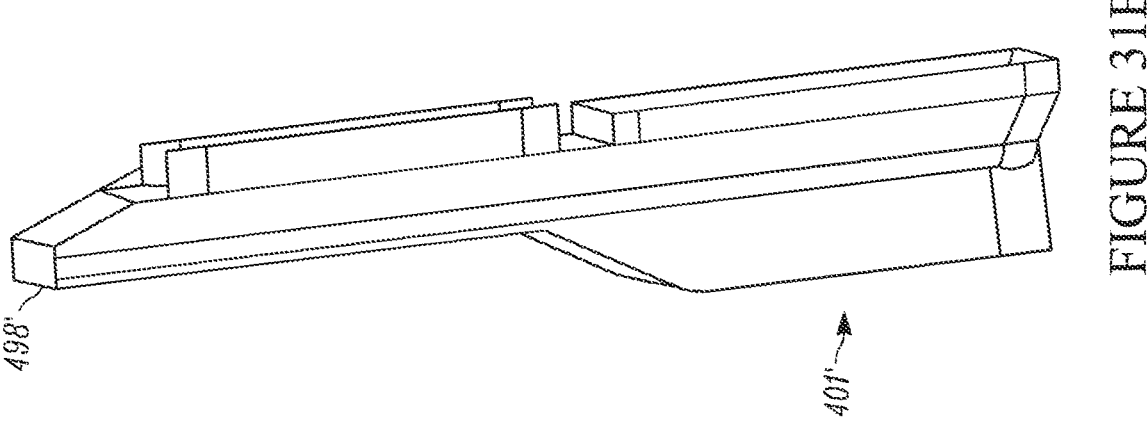
FIG. 31B is a side view of the lens body of FIG. 31A.
Figure 31A:
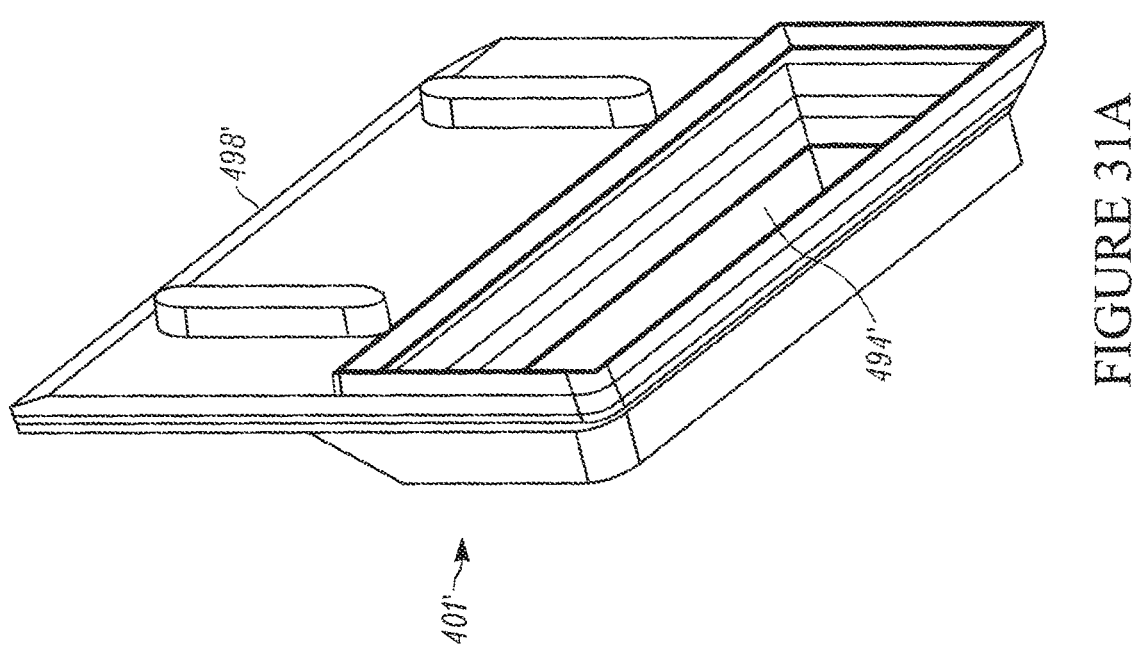
FIG. 31A is a perspective view of a lens body according to one embodiment.

For ease of assembly and for disposing sensors in seed firmer 400', seed firmer 400' can be fabricated from component parts. In this embodiment, seed firmer 400' has a resilient portion 410', which mounts to shank 254 and can urge seed firmer body portion 490' into resilient engagement with the trench 38. Firmer body portion 490' includes a firmer base 495', sensor housing 496', and lens body 498'. Base 495' is illustrated in FIGS. 29A to 29C. Sensor housing 496' is illustrated in FIG. 30A, and a cover 497' for mating with sensor housing 496' is illustrated in FIG. 30B. Lens body 498' is illustrated in FIGS. 31A and 31B, and lens body 498' is disposed in opening 499' in firmer base 495'. Lens 402' is disposed in lens opening 494' in lens body 498'. Sensors are disposed (such as on a circuit board, such as 580 or 2596) in sensor housing 496'. As illustrated in FIG. 27B, there is a conduit 493' disposed through a side of resilient portion 410' and entering into sensor housing 496' for wiring (not shown) to connect to the sensors.

Protrusion 401' will primarily be on lens body 498', but a portion of protrusion 401' can also be disposed on firmer body 495' to either or both sides of lens body 498' to create a taper out to and back from protrusion 401'. It is expected protrusion 401' will wear with contact with the soil. Disposing a major portion of protrusion 401' on lens body 498' allows for replacement of lens body 498' after protrusion 401' and/or lens 402' become worn or broken.

Figure 53:
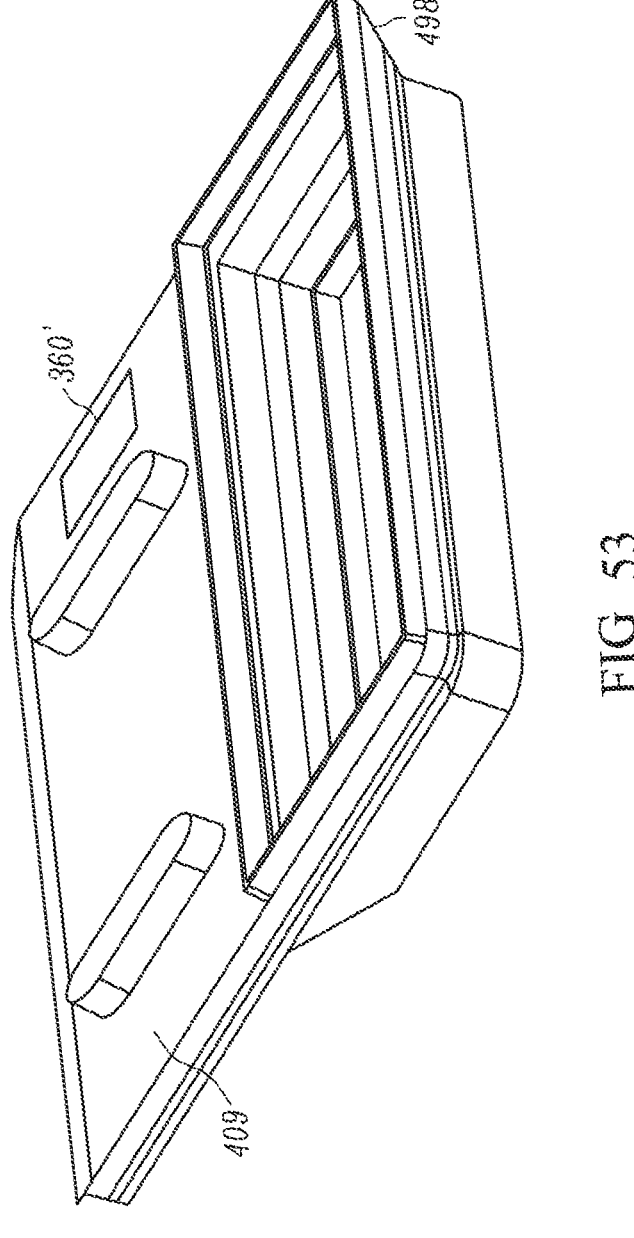
FIG. 53 is a perspective view of a temperature sensor disposed on an interior wall according to one embodiment.

In another embodiment illustrated in FIG. 53, a temperature sensor 360' is disposed in a seed firmer 400 (the reference to seed firmer 400 in this paragraph is to any seed firmer such as 400, 400', 400", or 400''') to measure temperature on an interior wall 409 that is in thermal conductivity with an exterior of seed firmer 400. Temperature sensor 360' measures the temperature of interior wall 409. In one embodiment, the area of interior wall 409 that temperature sensor 360' measures is no more than 50% of the area of interior wall 409. In other embodiments, the area is no more than 40%, no more than 30%, no more than 20%, no more than 10%, or no more than 5%. The smaller the area, the faster that temperature sensor 360' can react to changes in temperature. In one embodiment, temperature sensor 360' is a thermistor. Temperature sensor 360' can be in electrical communication with a circuit board (such as circuit board 580 or 2596).

Figure 54:
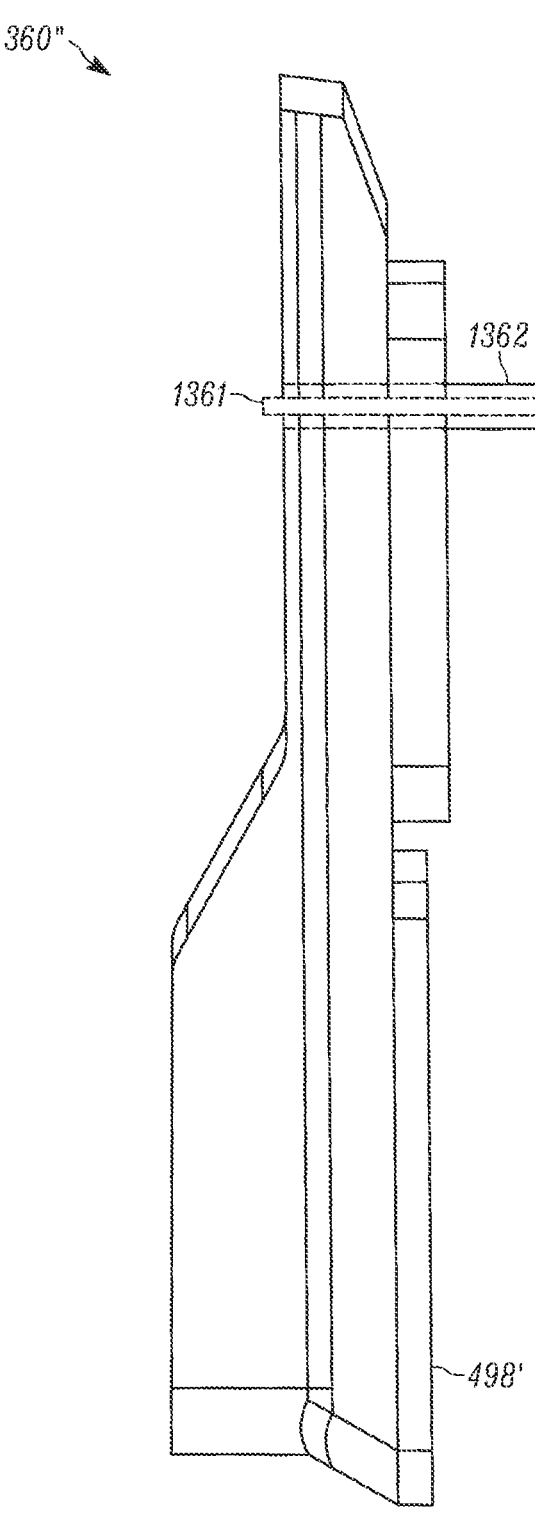
FIG. 54 is a side view of a temperature sensor disposed through a seed firmer to measure temperature of soil directly according to one embodiment.

In another embodiment illustrated in FIG. 54, a temperature sensor 360" is disposed through seed firmer 400 (the reference to seed firmer 400 in this paragraph is to any seed firmer such as 400, 400', 400", or 400''') to measure temperature of soil directly. Temperature sensor 360" has an internal thermally conductive material 1361 covered by a thermally insulating material 1362 with a portion of thermally conductive material 1361 exposed to contact soil. The thermally conductive material in one embodiment can be copper. Temperature sensor 360" can be in electrical communication with a circuit board (such as circuit board 580 or 2596).

In either of the embodiments in FIGS. 53 and 54, temperature sensor 360', 360" is modular. It can be a separate part that can be in communication with monitor 50 and separately replaceable from other parts.

Figure 32:
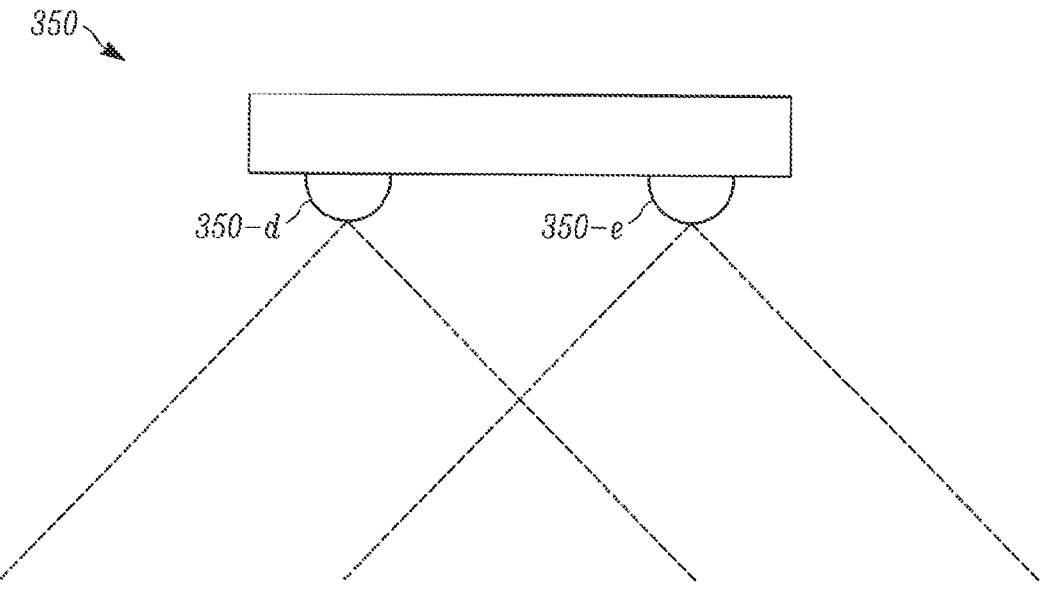
FIG. 32 is a side view of a sensor with an emitter and a detector according to one embodiment.

In one embodiment with seed firmer 400', the sensor is the reflectivity sensor 350. Reflectivity sensor 350 can be two components with an emitter 350-*e* and a detector 350-*d*. This embodiment is illustrated in FIG. 32.

In certain embodiments, the wavelength used in reflectivity sensor 350 is in a range of 400 to 1600 nm. In another embodiment, the wavelength is 550 to 1450 nm. In one embodiment, there is a combination of wavelengths. In one embodiment, sensor 350 has a combination of 574 nm, 850 nm, 940 nm, and 1450 nm. In another embodiment, sensor 350 has a combination of 589 nm, 850 nm, 940 nm, and 1450 nm. In another embodiment, sensor 350 has a combination of 640 nm, 850 nm, 940 nm, and 1450 nm. In another embodiment, the 850 nm wavelength in any of the previous embodiments is replaced with 1200 nm. In another embodiment, the 574 nm wavelength of any of the previous embodiments is replaced with 590 nm. For each of the wavelengths described herein, it is to be understood that the number is actually +/−10 nm of the listed value. In certain embodiments, the combination of wavelengths is 460 nm, 589 nm, 850 nm, 1200 nm, and 1450 nm is used.

In one embodiment, the field of view from the front 402-*f* of lens 402' to the soil surface is 0 to 7.5 mm (0 to 0.3 inches). In another embodiment, the field of view is 0 to 6.25 mm (0 to 0.25 inches). In another embodiment, the field of view is 0 to 5 mm (0 to 0.2 inches). In another embodiment, the field of is 0 to 2.5 mm (0 to 0.1 inches).

As seed firmer 400' travels across trench 38, there may be instances where there is a gap between trench 38 and seed firmer 400' such that ambient light will be detected by reflectivity sensor 350. This will give a falsely high result. In one embodiment to remove the signal increase from ambient light, emitter 350-*e* can be pulsed on and off. The background signal is measured when there is no signal from emitter 350-*e*. The measured reflectivity is then determined by subtracting the background signal from the raw signal when emitter 350-*e* is emitting to provide the actual amount of reflectivity.

Figure 33:
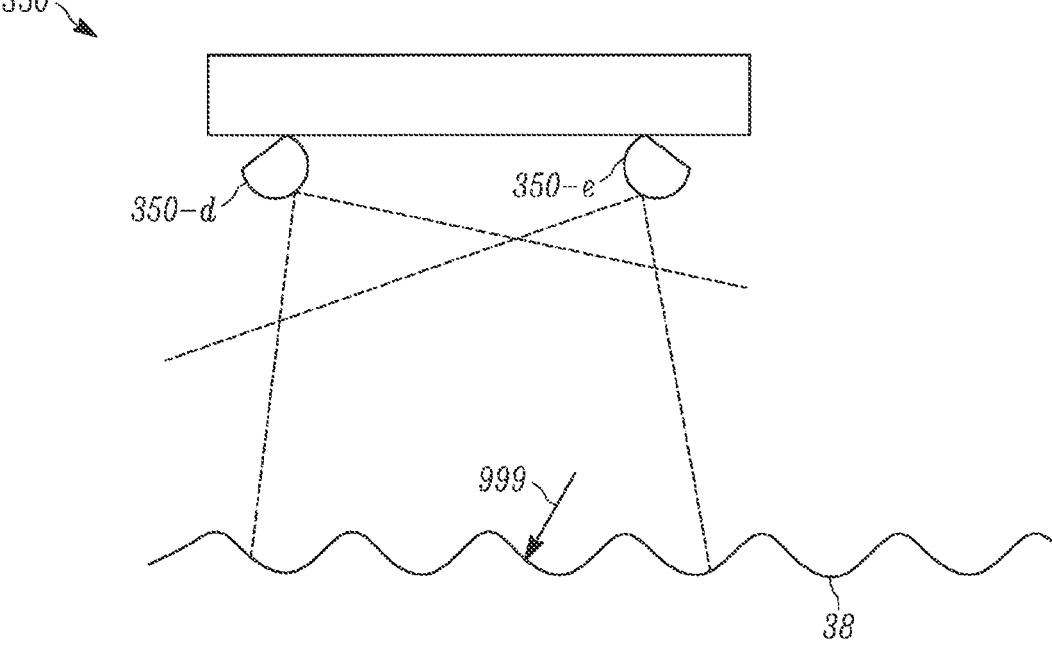
FIG. 33 is a side view of a sensor with an emitter and a detector that are angled towards each other according to one embodiment.

As shown in FIG. 32, when reflectivity sensor 350 has just one emitter 350-*e* and one detector 350-*d*, the area of overlap between the area illuminated by emitter 350-*e* and the area viewed by detector 350-*d* can be limited. In one embodiment as illustrated in FIG. 33, emitter 350-*e* and detector 350-*d* can be angled towards each other to increase the overlap. While this is effective, this embodiment does increase the manufacturing cost to angle the emitter 350-*e* and detector 350-*d*. Also, when the surface of trench 38 is not smooth, there can be some ray of light 999 that will impact trench 38 and not be reflected towards detector 350-*d*.

Figure 34:
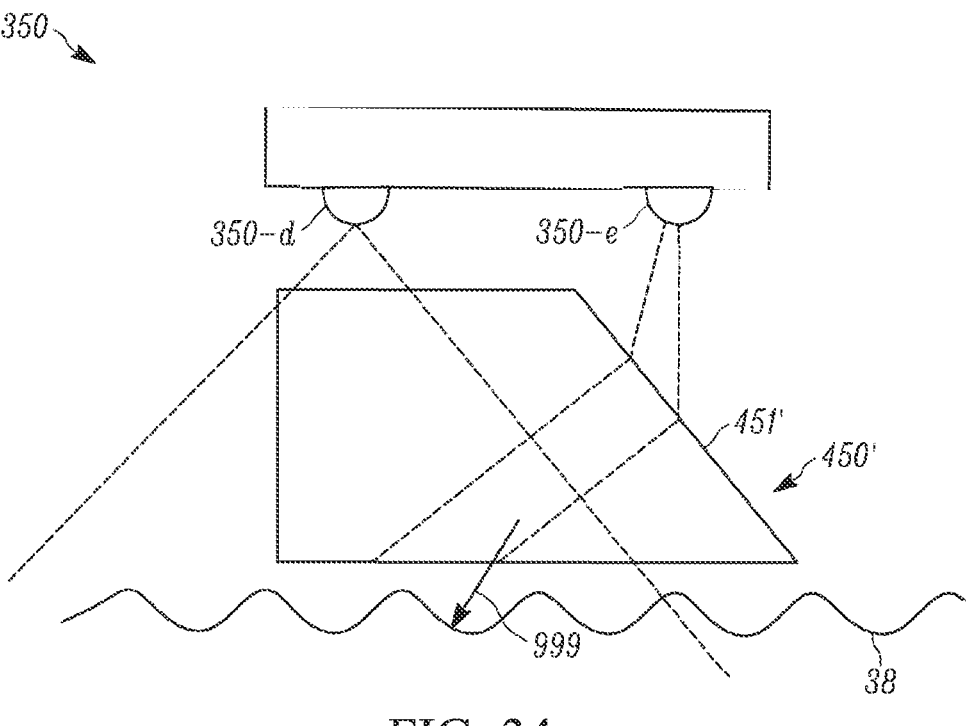
FIG. 34 is a side view of a sensor and prism combination according to one embodiment.

In another embodiment illustrated in FIG. 34, the configuration from FIG. 32 can be used, and a prism 450' with a sloped side 451' disposed under emitter 350-*e* can refract the light from emitter 350-*e* towards the area viewed by detector 350-*d*. Again with a single emitter 350-*e*, ray of light 999 may impact trench 38 and not be reflected towards detector 350-*d*.

Figure 35:
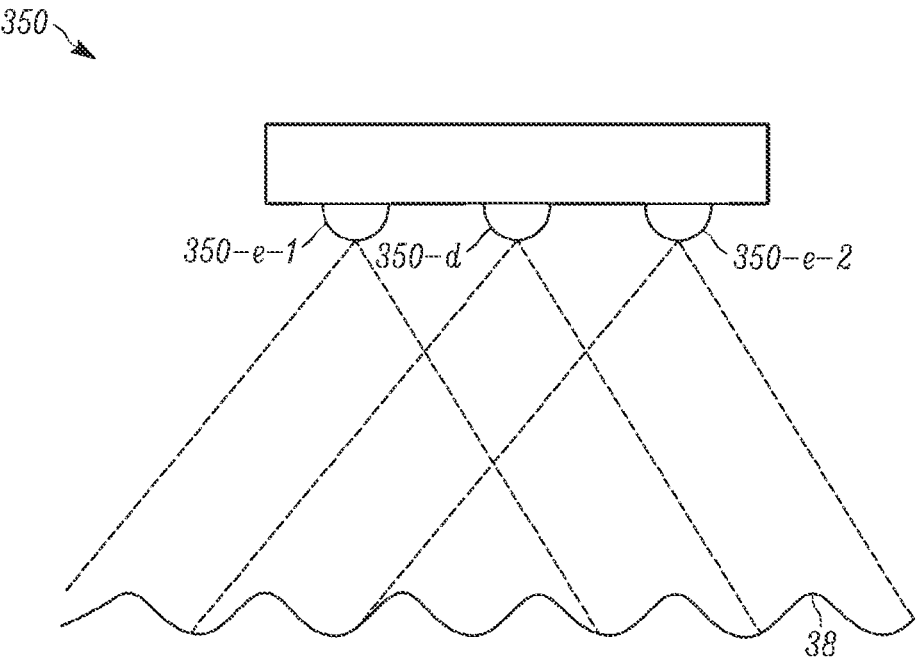
FIG. 35 is a side view of a sensor with two emitters and a detector according to one embodiment.
Figure 36:
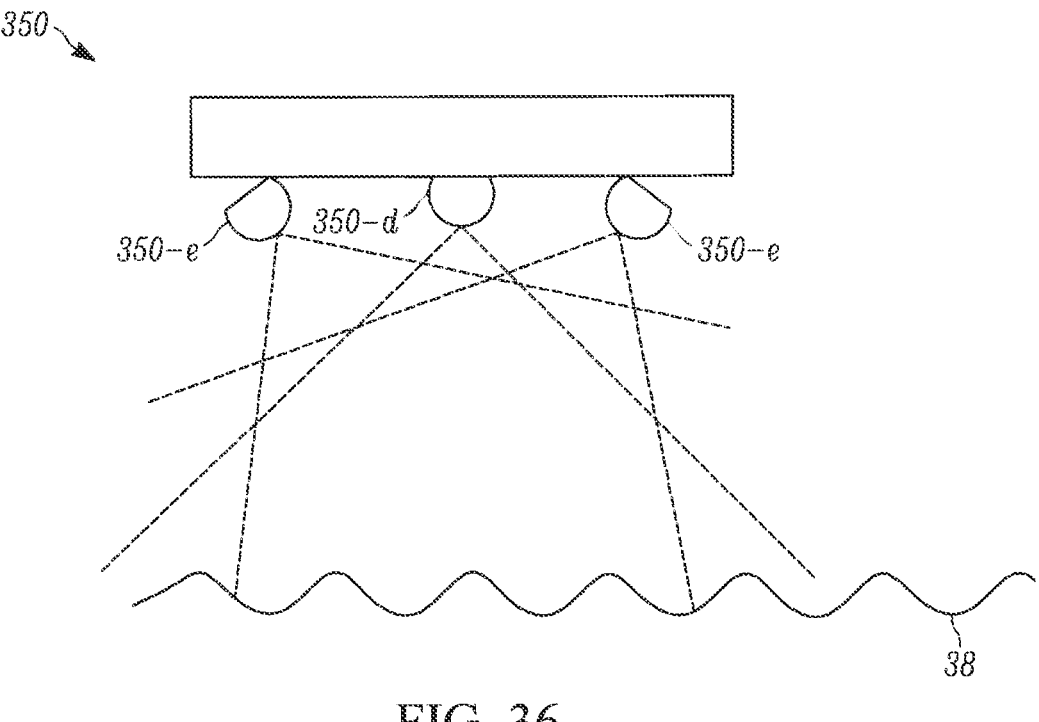
FIG. 36 is a side view of a sensor with two emitters angled toward a detector according to one embodiment.

In another embodiment illustrated in FIG. 35, sensor 350 can have two emitters 350-*e*-1 and 350-*e*-2 and one detector 350-*d*. This increases the overlap between the area viewed by detector 350-*d* and the area illuminated by emitters 350-*e*-1 and 350-*e*-2. In another embodiment, to further increase the overlap, emitters 350-*e*-1 and 350-*e*-2 can be angled towards detector 350-*d* as illustrated in FIG. 36.

Figure 37:
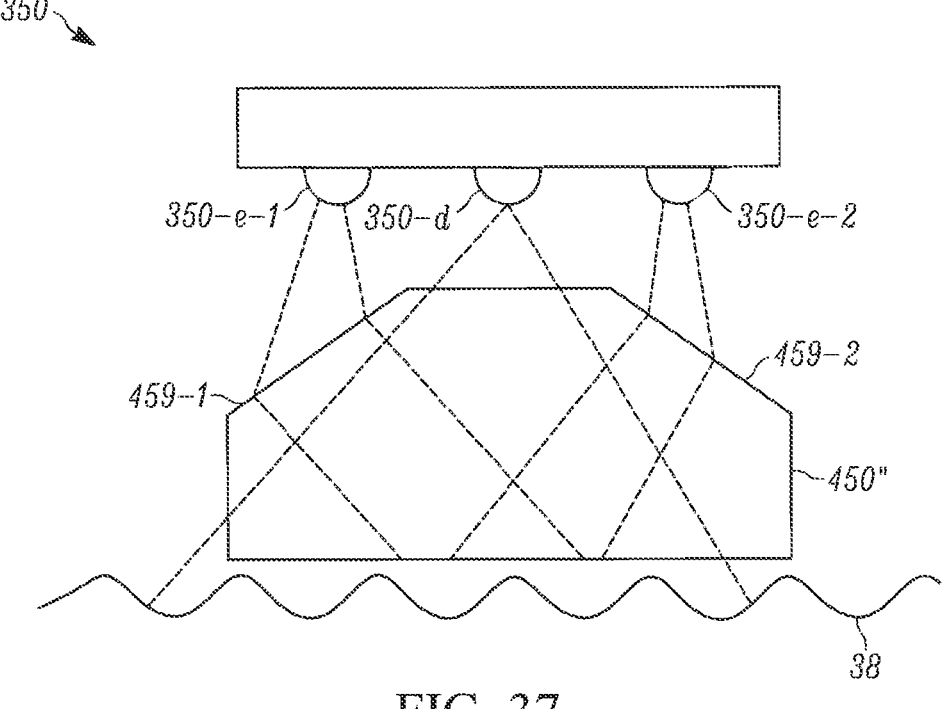
FIG. 37 is a side view of a sensor with two emitters and a detector and a prism according to one embodiment.

In another embodiment illustrated in FIG. 37, two emitters 350-*e*-1 and 350-*e*-2 are disposed next to detector 350-*d*. A prism 450" has two sloped surfaces 459-1 and 459-2 for refracting light from emitters 350-*e*-1 and 350-*e*-2 towards the area viewed by detector 350-*d*.

Figure 38:
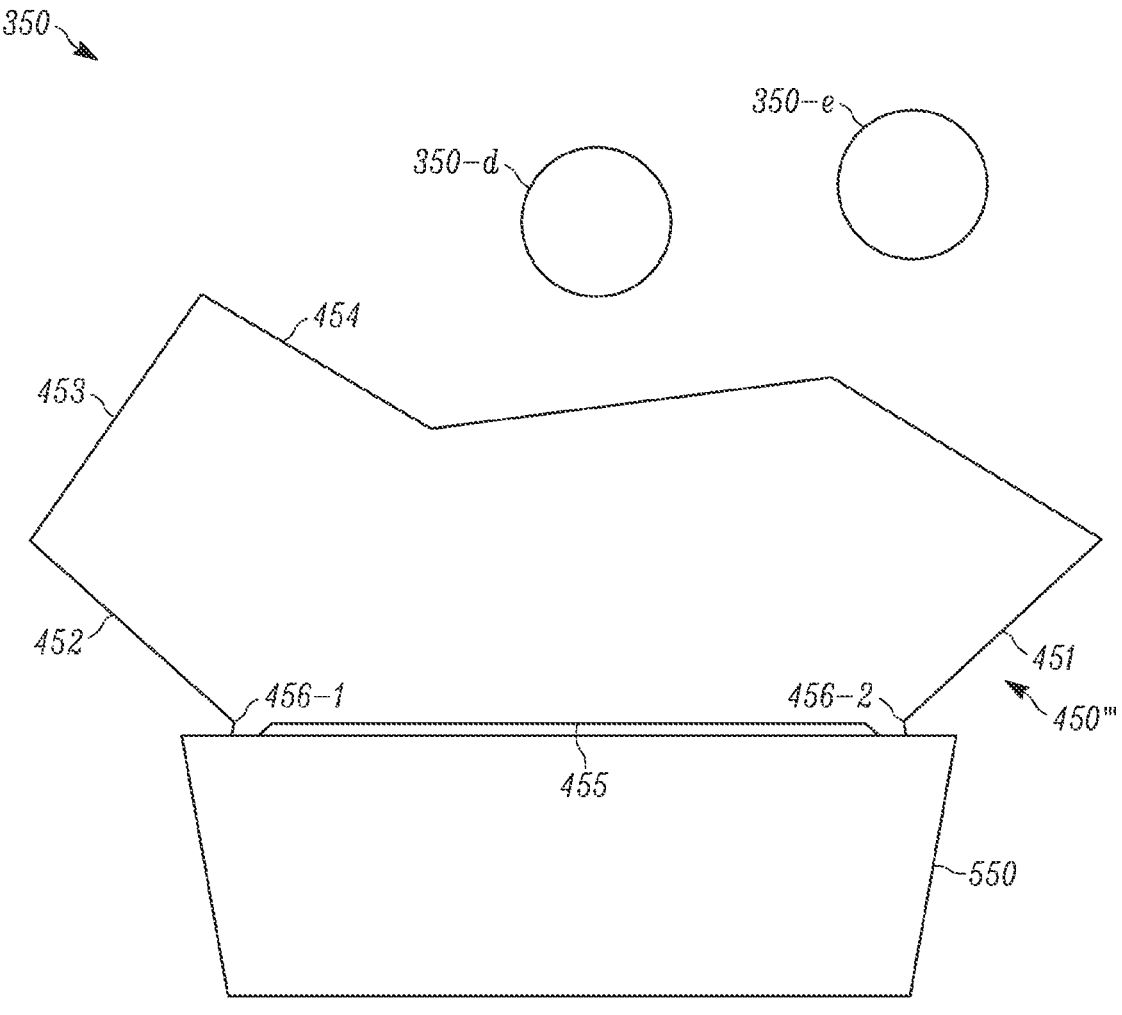
FIG. 38 is a side view of a sensor with an emitter and a detector along with a prism that uses the critical angle of the material of the prism according to one embodiment.

In another embodiment illustrated in FIG. 38, a single emitter 350-*e* can be used in conjunction with a prism 450" to approximate a dual emitter. Prism 450''' is designed with angled sides to utilize the critical angle of the material used to make prism 450" (to keep light within the material). The angles vary depending on the material. In one embodiment, the material for prism 450''' is polycarbonate. A portion of the light from emitter 350-*e* will impact side 451 and be reflected to side 452 to side 453 to side 454 before exiting bottom 455. Optionally, spacers 456-1 and 456-2 can be disposed on the bottom 455 to provide a gap between prism 450''' and lens 550.

Figure 39:
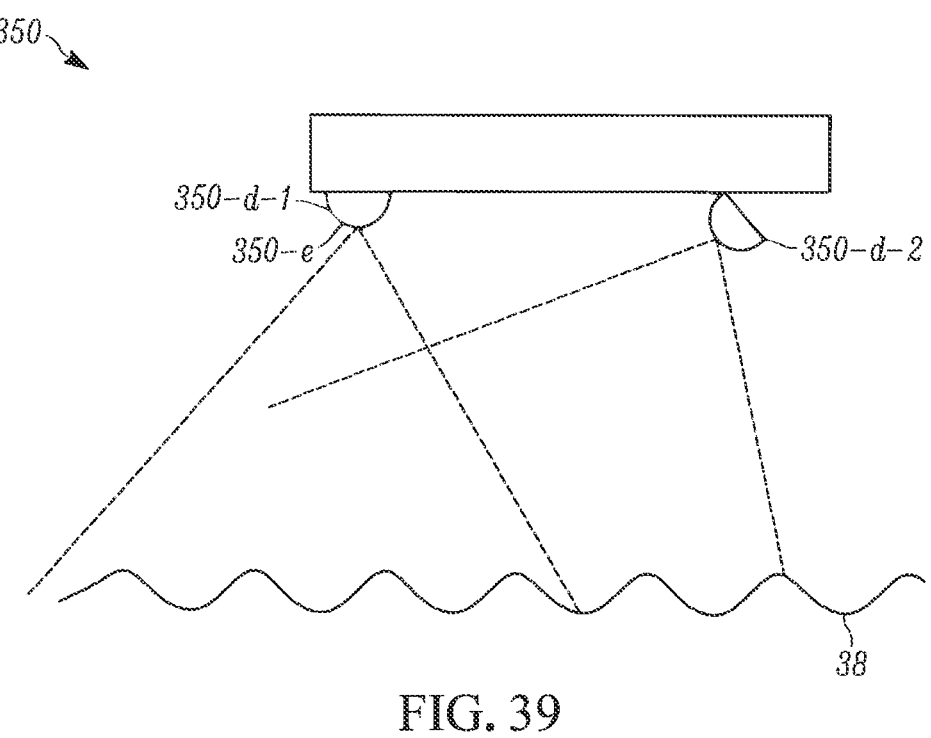
FIG. 39 is a side view of a sensor with one emitter and two detectors according to one embodiment.

In another embodiment, illustrated in FIG. 39, reflectivity sensor has one emitter 350-*e* and two detectors 350-*d*-1 and 350-*d*-2. As shown, emitter 350-*e* and detector 350-*d*-1 are aligned as viewed into the figure. Detector 350-*d*-2 is angled towards emitter 350-1 and detector 350-*d*-2.

Figure 40:
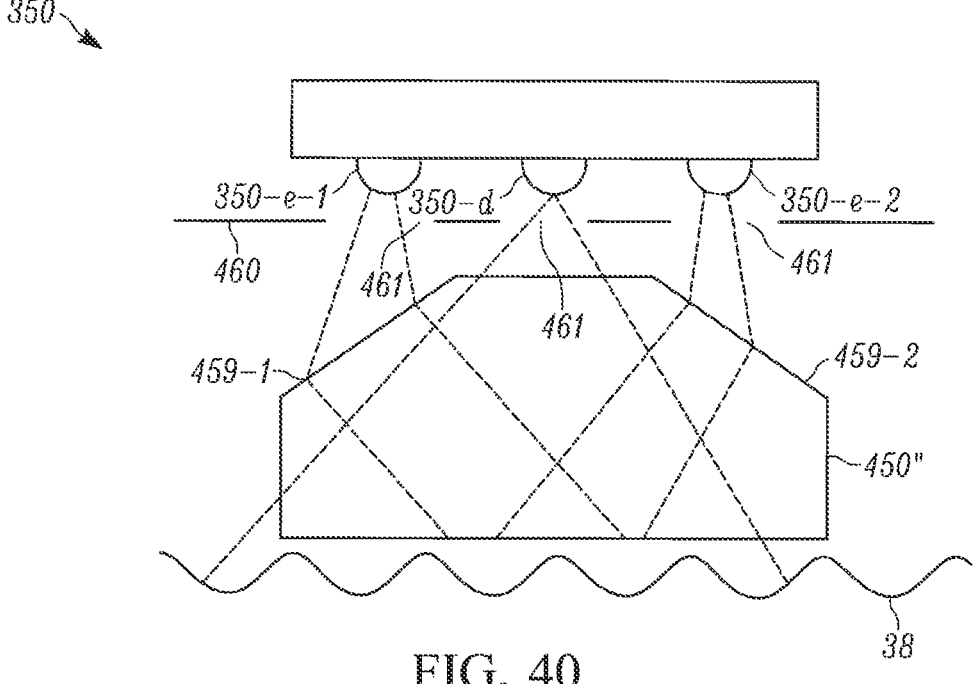
FIG. 40 is a side sectional view of an orifice plate used with the embodiment of FIG. 37.

In another embodiment that can be used with any of the previous embodiments or following embodiments, an aperture plate 460 can be disposed adjacent to the sensor 350 with apertures 461 adjacent to each emitter 350-*e* and detector 350-*d*. This embodiment is illustrated in FIG. 40 with the embodiment from FIG. 37. The aperture plate 460 can assist in controlling the half angles.

Figure 41:
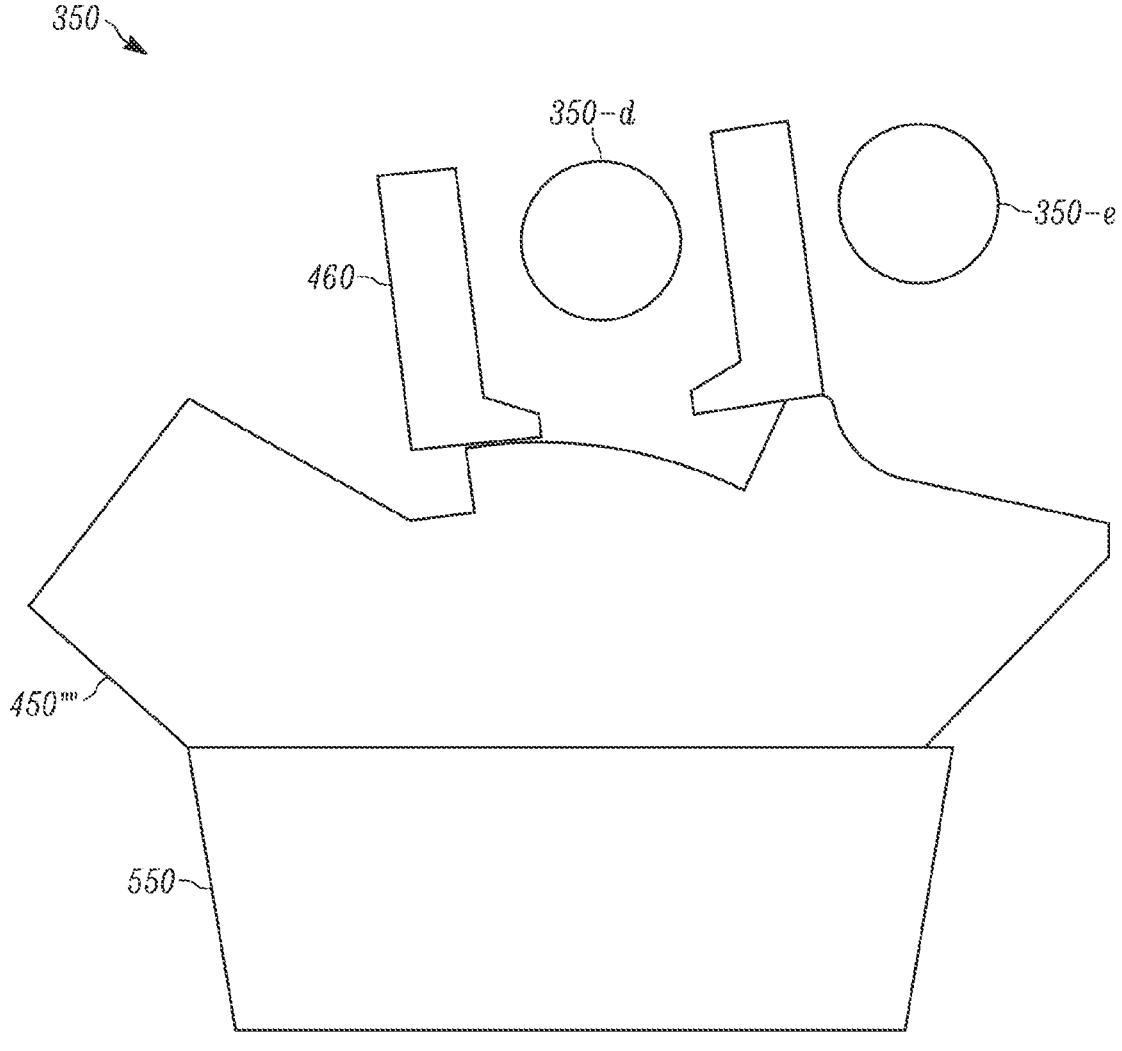
FIG. 41 is a side sectional view of a sensor with one emitter and one detector along with a prism that uses the critical angle of the material of the prism according to one embodiment.
Figure 42A:
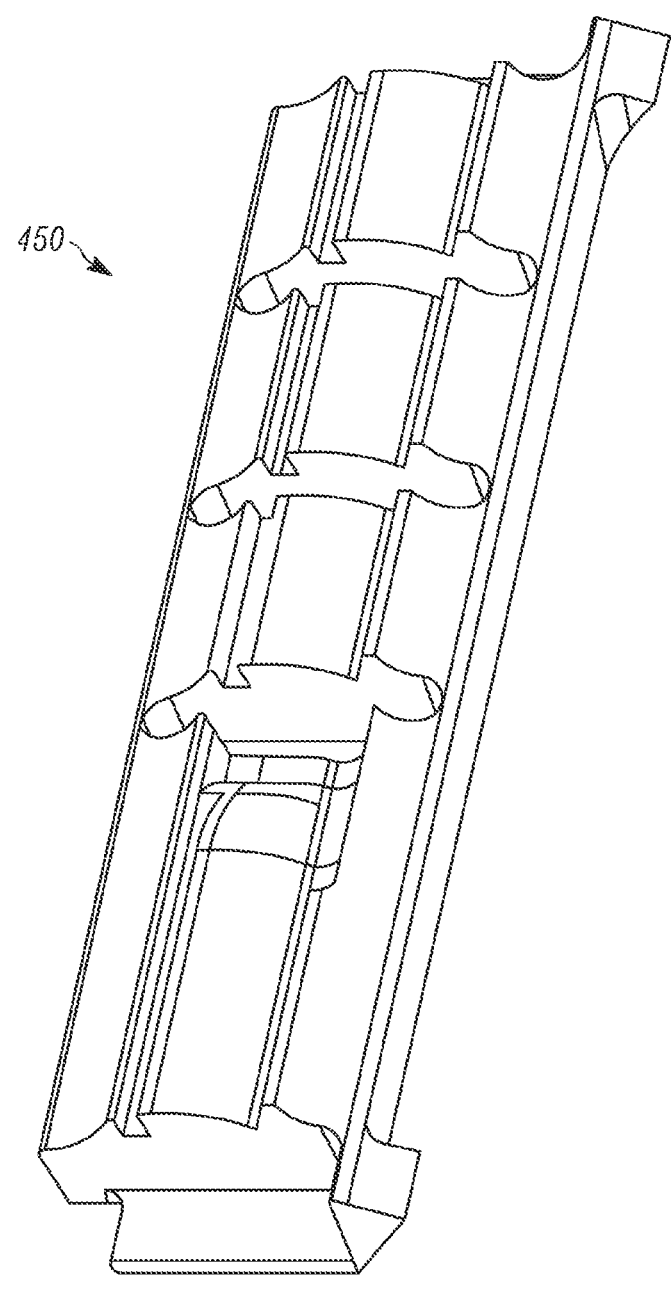
FIG. 42A is an isometric view of a prism according to one embodiment.
Figure 42B:
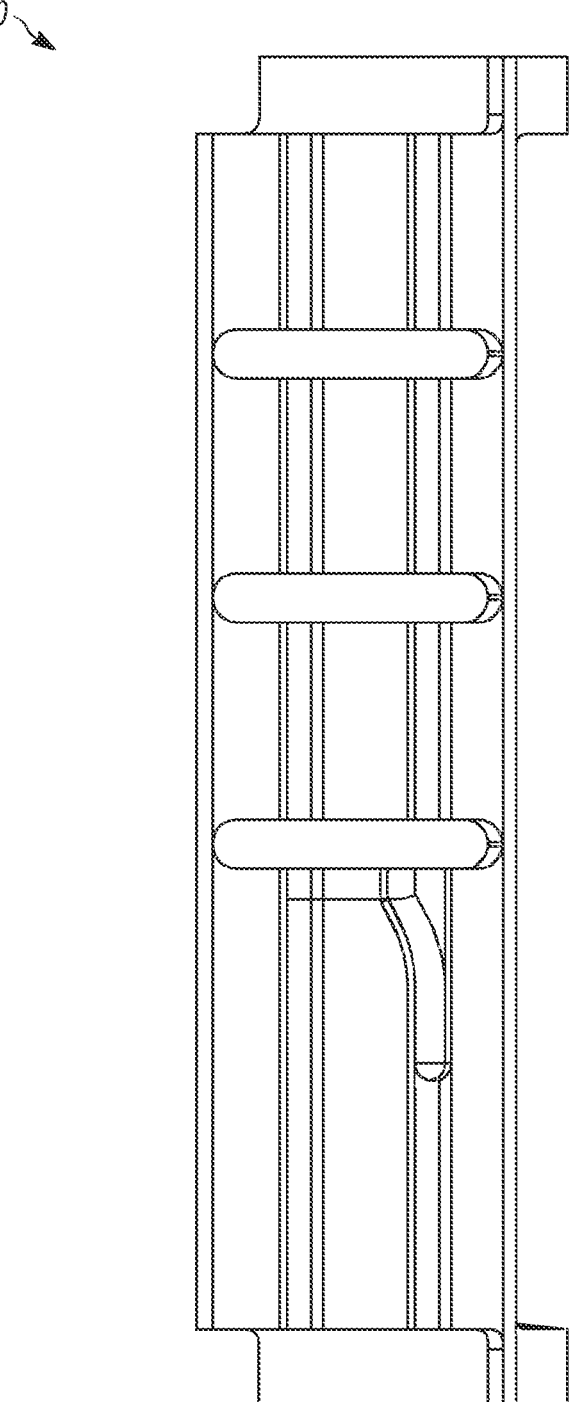
FIG. 42B is a top plan view of the prism of FIG. 42A.
Figure 42C:
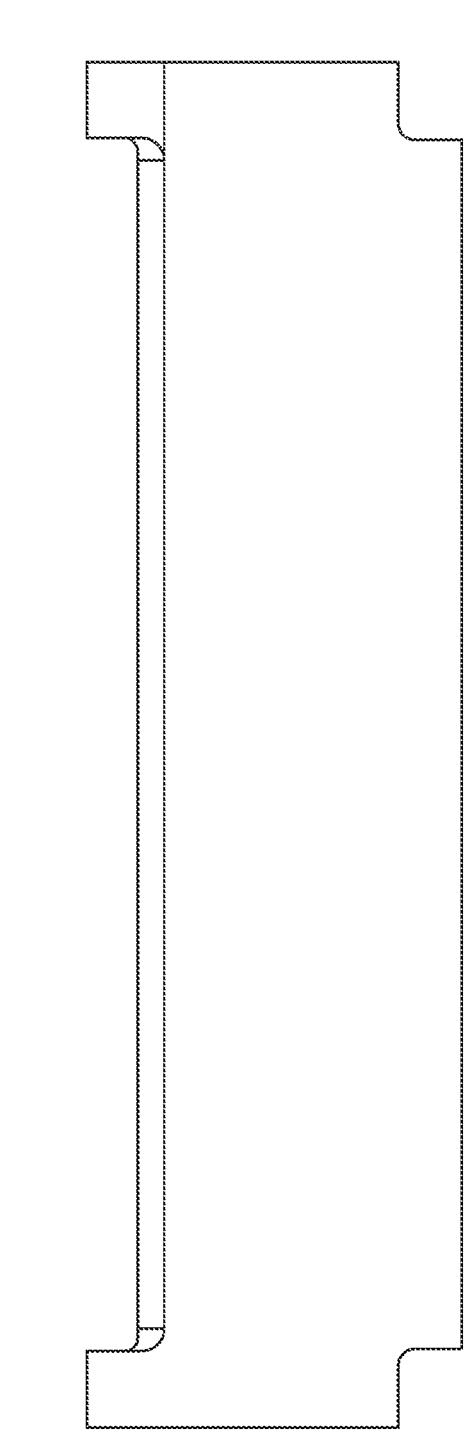
FIG. 42C is a bottom elevation view of the prism of FIG. 42A.
Figure 42D:
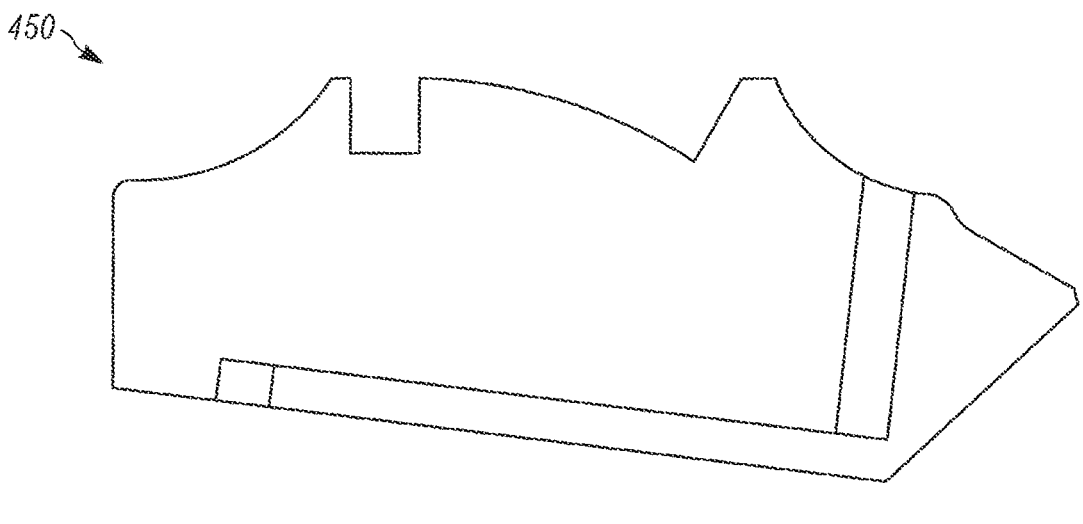
FIG. 42D is a front elevation view of the prism of FIG. 42A.
Figure 42E:
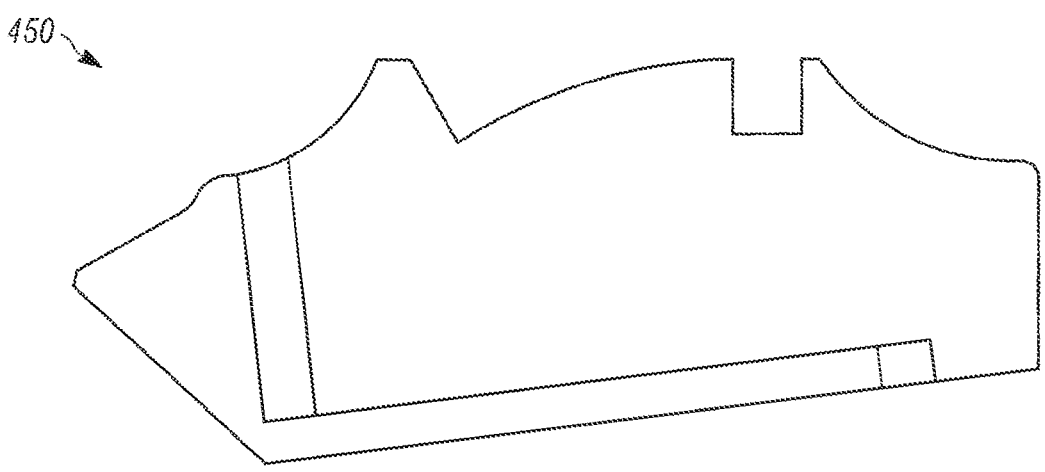
FIG. 42E is a rear elevation view of the prism of FIG. 42A.
Figures 42F, 42G:
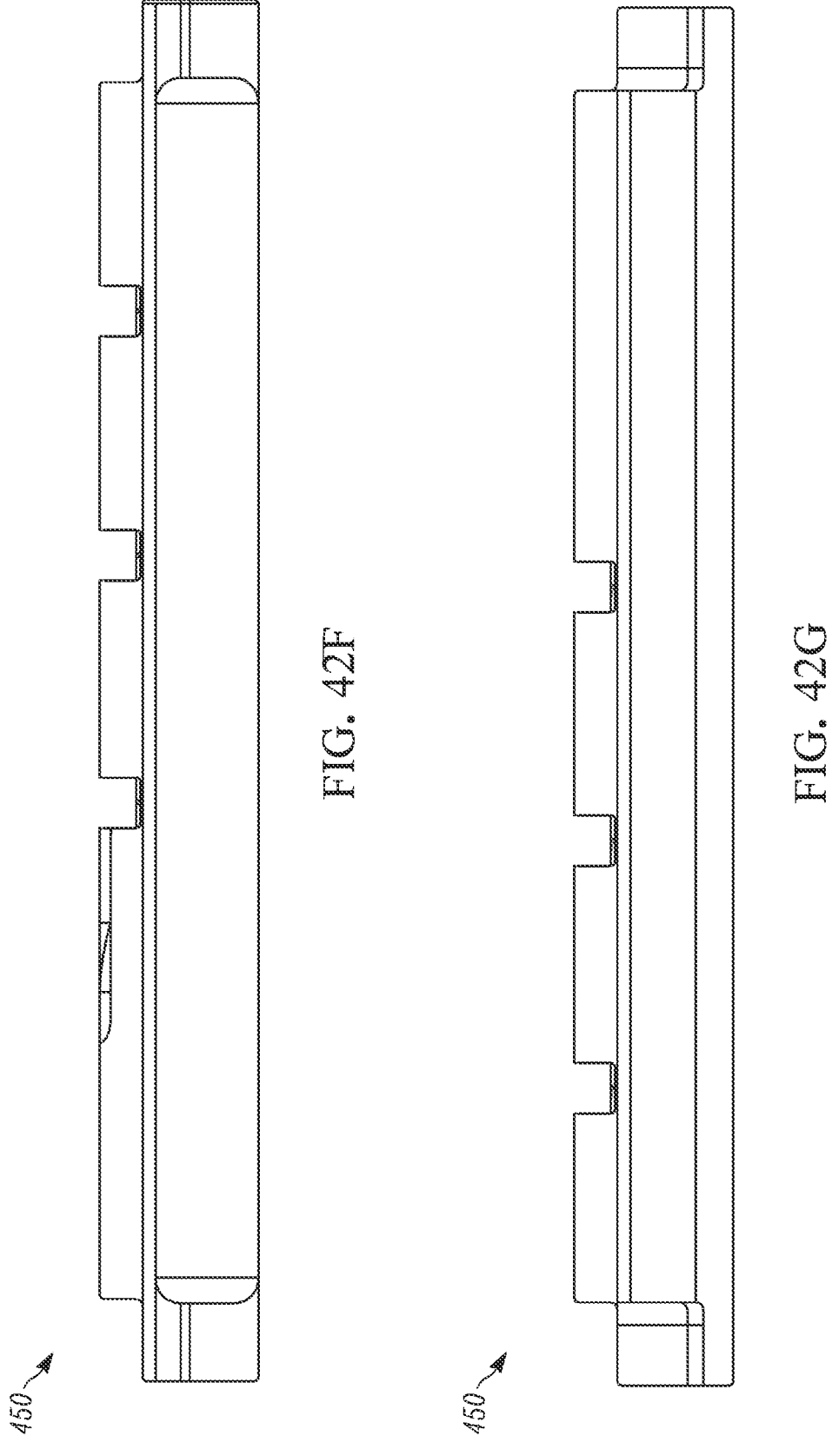
FIG. 42F is a right elevation view of the prism of FIG. 42A.
FIG. 42G is a left elevation view of the prism of FIG. 42A.

In another embodiment illustrated in FIG. 41, a reflectivity sensor 350 has one emitter 350-*e* and one detector 350-*d*. Disposed adjacent to the detector is an orifice plate 460 that is only controlling the light entering detector 350-*d*. Prism 450''' is then disposed adjacent to the emitter 350-*e* and detector 350-*d*.

In another embodiment of a prism, multiple views of prism 450 can be seen in FIGS. 42A-42G.

Figure 43:
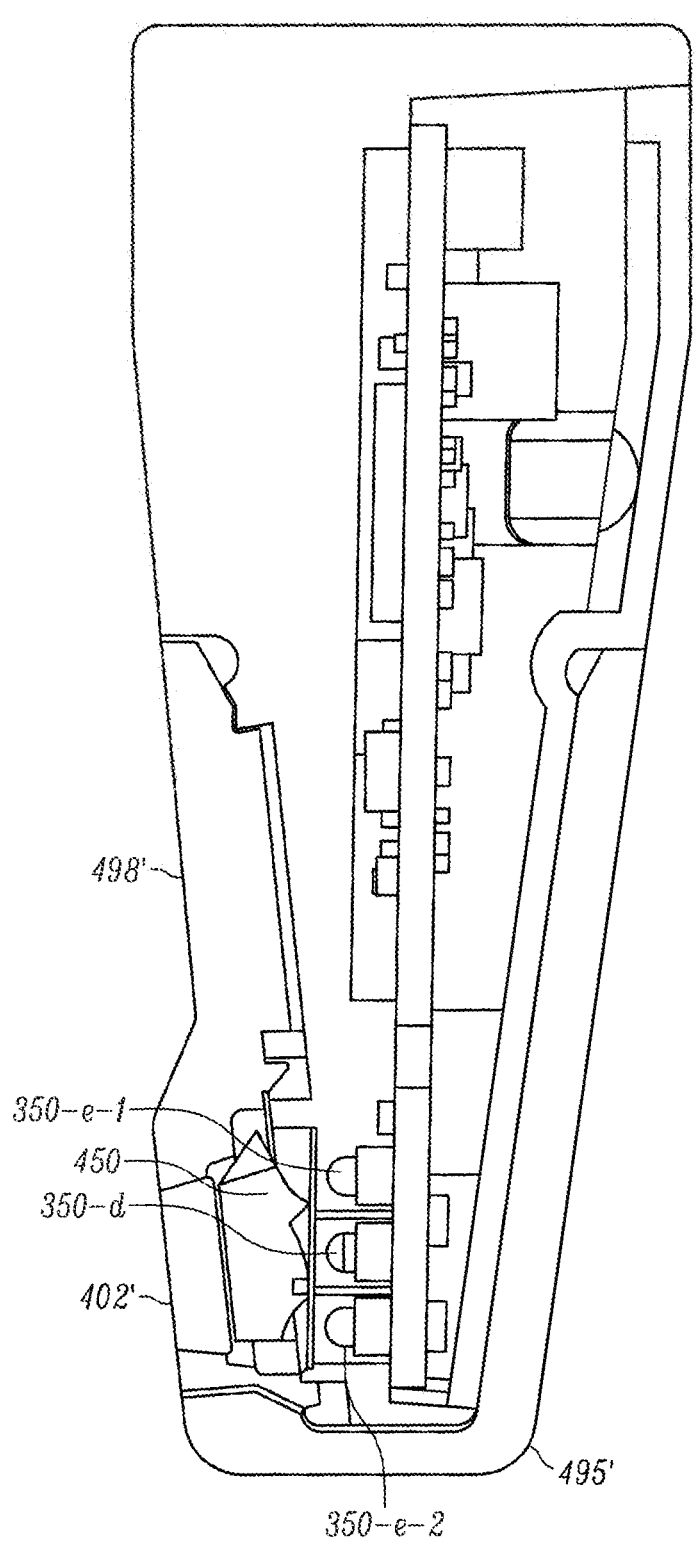
FIG. 43 is a sectional view of seed firmer of FIG. 27A at section A-A.

FIG. 43 is a cross-sectional view of seed firmer 400' of FIG. 27A taken at section A-A. Two emitters 350-*e*-1 and 350-*e*-2 and one detector 350-*d* are disposed in sensor housing 496'. Prism 450 from FIGS. 42A-42G is disposed between emitters 350-*e*-1 and 350-*e*-2 and detector 350-*d* and lens 402'.

Figure 44A:
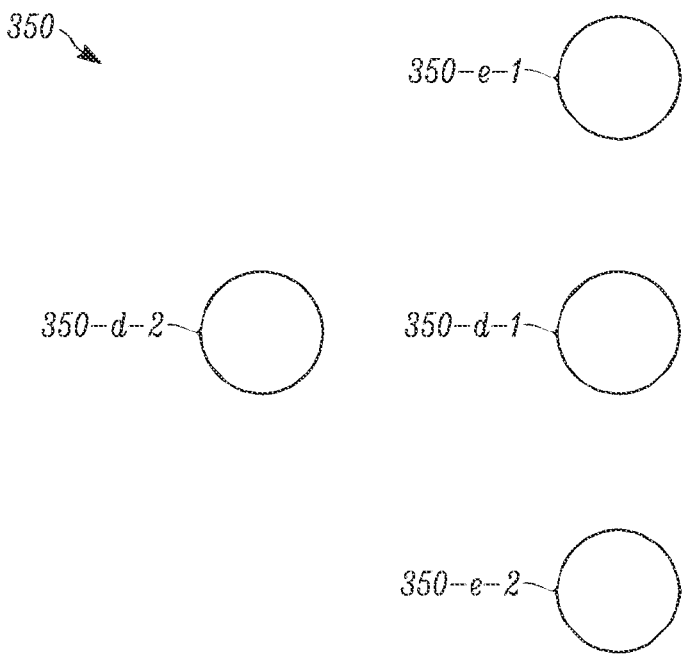
FIG. 44A is a front schematic view of a sensor with two emitters and one detector in line and an offset detector according to one embodiment.
Figure 44B:
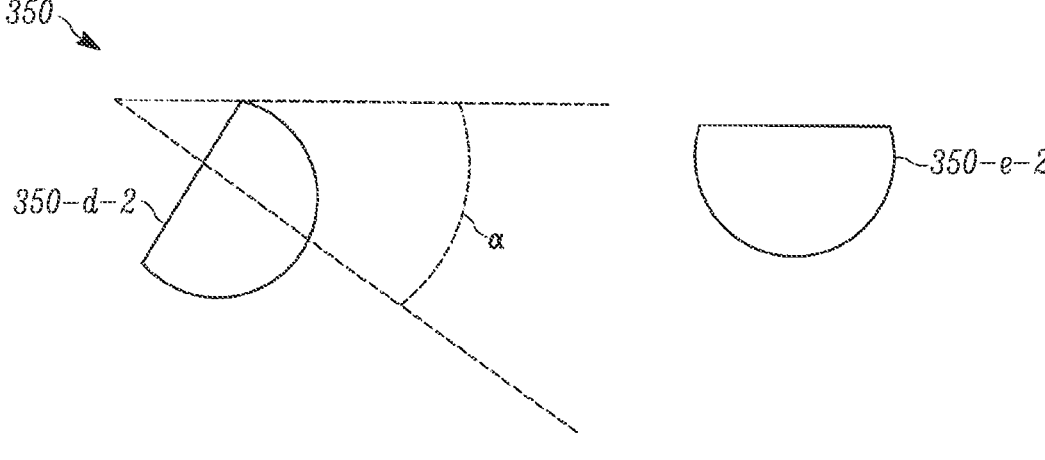
FIG. 44B is a side schematic view of the sensor of FIG. 44A.

In another embodiment as illustrated in FIGS. 44A and 44B, there is a reflectivity sensor 350 that has two emitters 350-*e*-1 and 350-*e*-2 in line with a detector 350-*d*-1. As viewed the emitters 350-*e*-1 and 350-*e*-2 are pointed out of the paper, and the view of detector 350-*d*-1 is pointed out of the paper. There is a second detector that is offset from emitters 350-*e*-1 and 350-*e*-2 and detector 350-*d*-1. In another embodiment (not shown) emitter 350-*e*-2 is omitted. As seen in FIG. 44B, detector 350-*d*-2 is angled from vertical by an angle α and is viewing towards emitters 350-*e*-1 and 350-*e*-2 and detector 350-*d*-1, which are aligned into the paper. In one embodiment, the angle α is 30 to 60°. In another embodiment, the angle α is 45°. In one embodiment, the wavelength of light used in this arrangement is 940 nm. This arrangement allows for measurement of void spaces in soil. Detecting void spaces in soil will inform how effective tillage has been. The less or smaller void spaces indicates more compaction and less effective tillage. More or larger void spaces indicates better tillage. Having this measurement of tillage effectiveness allows for adjustment of downforce on row unit 200 as described herein.

Figure 47:
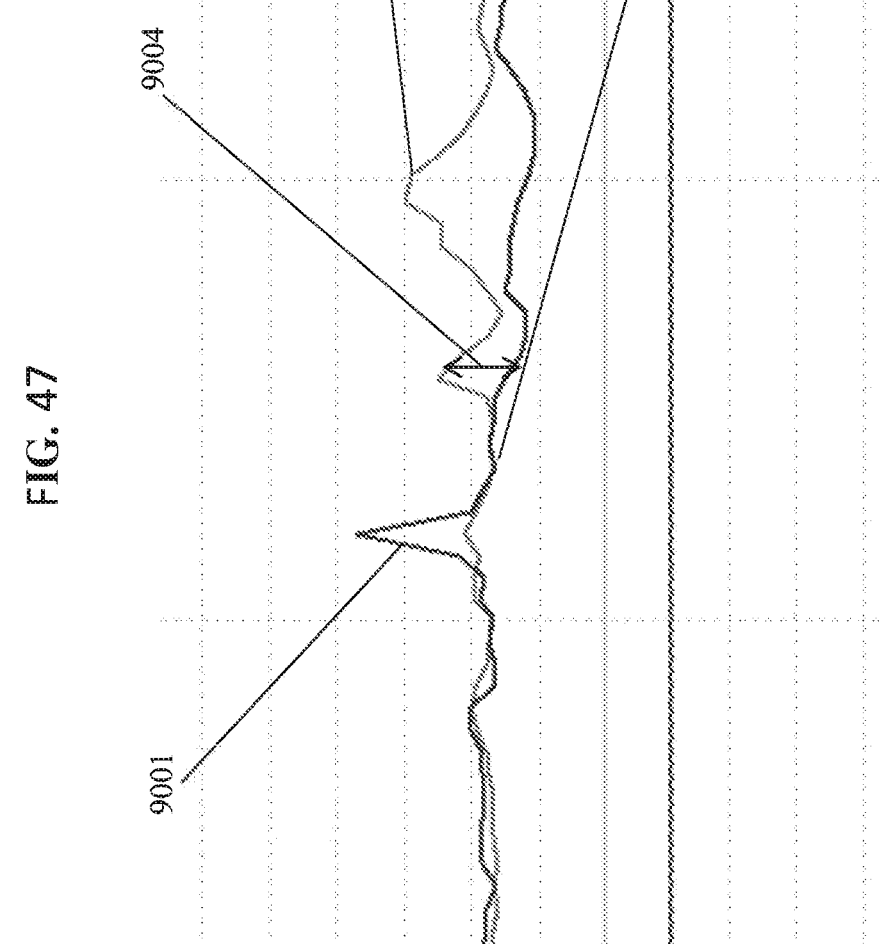
FIG. 47 illustrates a representative reflectance measurement and height off target.
Figure 48:
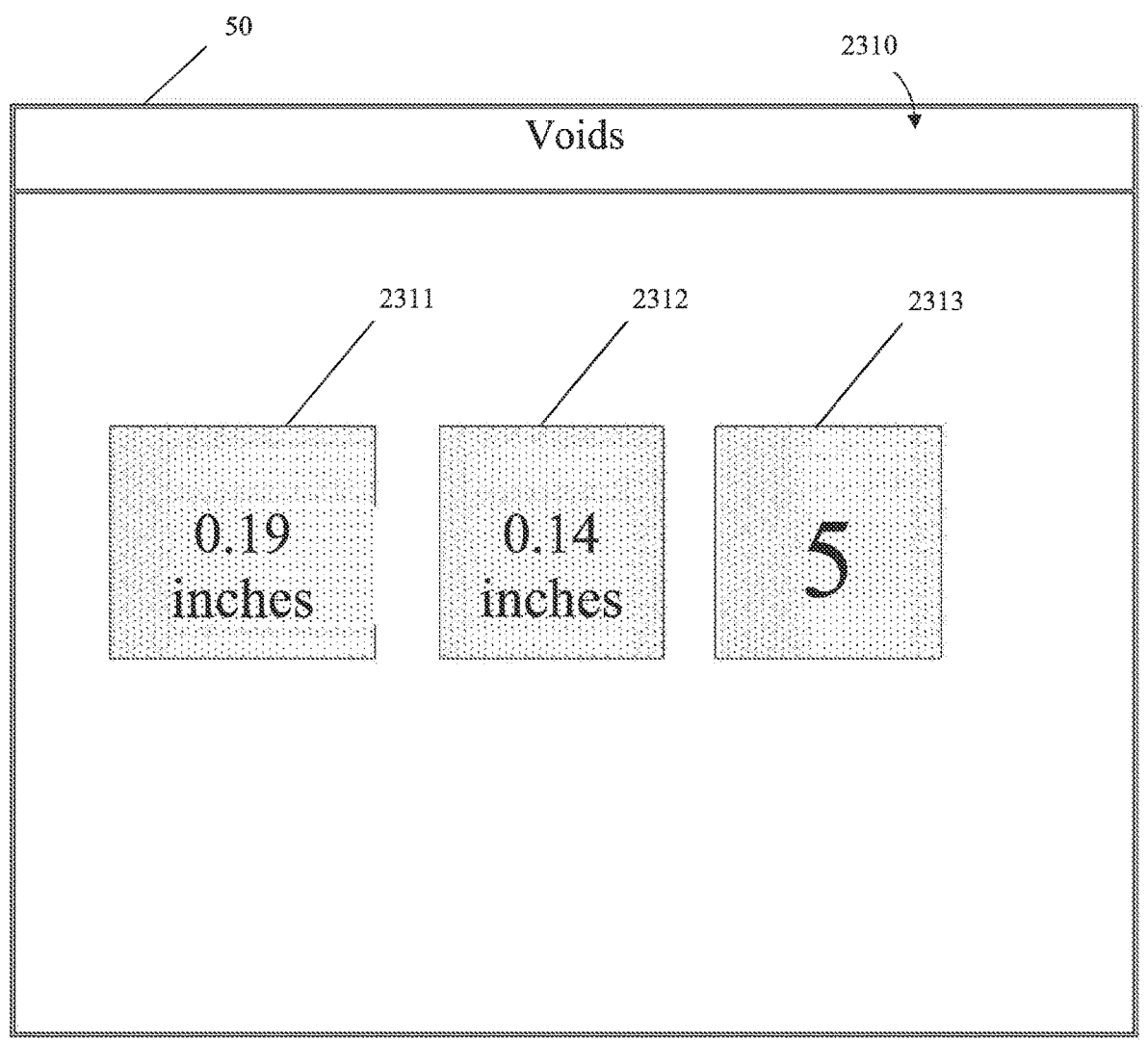
FIG. 48 illustrates an embodiment of a void screen.

The depth away from seed firmer 400, 400' and the length of void spaces can be measured by this arrangement. For short distances (generally up to 2.5 cm (1 inch) or up to about 1.27 cm (0.5 inches), the signal output from detector 350-*d*-2 increases as the distance to the target surface increases. While the signal from the primary reflectance detector, 350-*d*-1, stays mostly constant to slightly decreasing. An illustrative reflectance measurement is shown in FIG. 47 along with a corresponding calculated height off of target for a soil apparatus. The reflectance measurement from 350-*d*-1 9001 and the reflectance measurement from 350-*d*-2 9002 are shown. When reflectance measurement from 350-*d*-1 9001 and the reflectance measurement from 350-*d*-2 9002 are approximately the same, region 9003 is when target soil is flush with lens 402'. As a void is detected at region 9004, reflectance measurement from 350-*d*-1 9001 remains about the same or decreases, and the reflectance measurement from 350-*d*-2 9002 increases. The distance from the target surface is a function of the ratio between signals produced by 350-*d*-1 and 350-*d*-2. In one embodiment, the distance is calculated as (350-*d*-2 signal–350-*d*-1 signal)/(350-*d*-2 signal+350-*d*-1 signal)*scaling constant. The scaling constant is a number that converts the reflectance measurement into distance. For the illustrated configuration, the scaling factor is 0.44. The scaling factor is measured and depends on emitter and detector placement, aperture plate dimensions, and prism geometry. In one embodiment, a scaling factor can be determined by placing a target at a known distance. A plot of the calculated target distance produces an elevation profile 9005 along the scanned surface. Knowing travel speed, the length 9006, depth 9007, and spacing 9008 of these voids can be calculated. A running average of these void characteristics (length 9006, depth 9007, and spacing 9008) can be calculated and then reported as another metric to characterize the texture of the soil being scanned. For example, once every second, a summary of average void length, average void depth, and number of voids during that period could be recorded/transmitted to monitor 50. The timing interval can be any selected amount of time greater than 0. Having a shorter amount of time, a smaller space is analyzed. An example of monitor 50 displaying on screen 2310 void length 2311, void depth 2312, and number of voids 2313 is illustrated in FIG. 48.

Figures 67, 68:
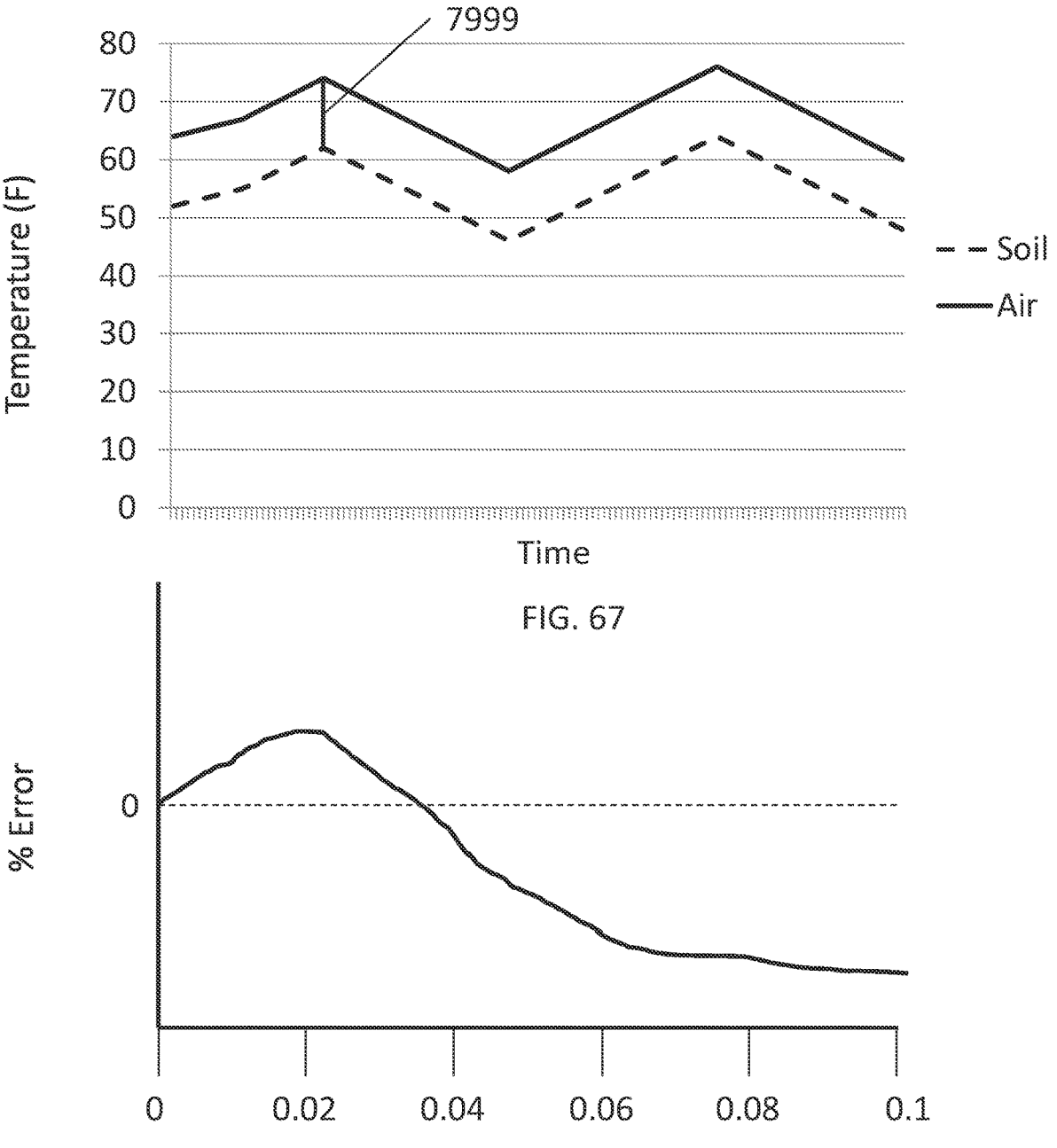
FIG. 67 illustrates a soil temperature and air temperature graph with a temperature offset.
FIG. 68 illustrates a correction factor curve for reflectance based on height off target.

There can be an error in measuring reflectance as the height off target for an apparatus (e.g., soil apparatus, seed firmer, sensor arm, etc.) increases. A correction can be used to convert the raw measured reflectance into a corrected measurement. A correction factor can be obtained by measuring reflectance at different heights off target. FIG. 68 illustrates an example of a correction curve. There can be regions where the percent error is greater than zero, such as at a short height off target, and there can be regions where the percent error is negative, such as at a long height off target. The percent error can be multiplied by a factor to obtain a 0% error. For example, if the percent error is 5% above the zero percent error line, then the measured value can be multiplied by about 95%.

In another embodiment, any scratches or films that form on lens 402' will affect the reflectivity detected by reflectivity sensor 350. There will be an increase in internal reflectivity within seed firmer 400, 400'. The increase in reflectivity will increase the reflectance measurement. This increase can be accounted for when seed firmer 400, 400' is removed from trench 38. The reading of seed firmer 400, 400' at this time will become the new base reading, e.g. zeroed out. The next time seed firmer 400, 400' is run in trench 38, the reflectivity above the new base or zero reading will be the actually measured reading.

Figure 45:
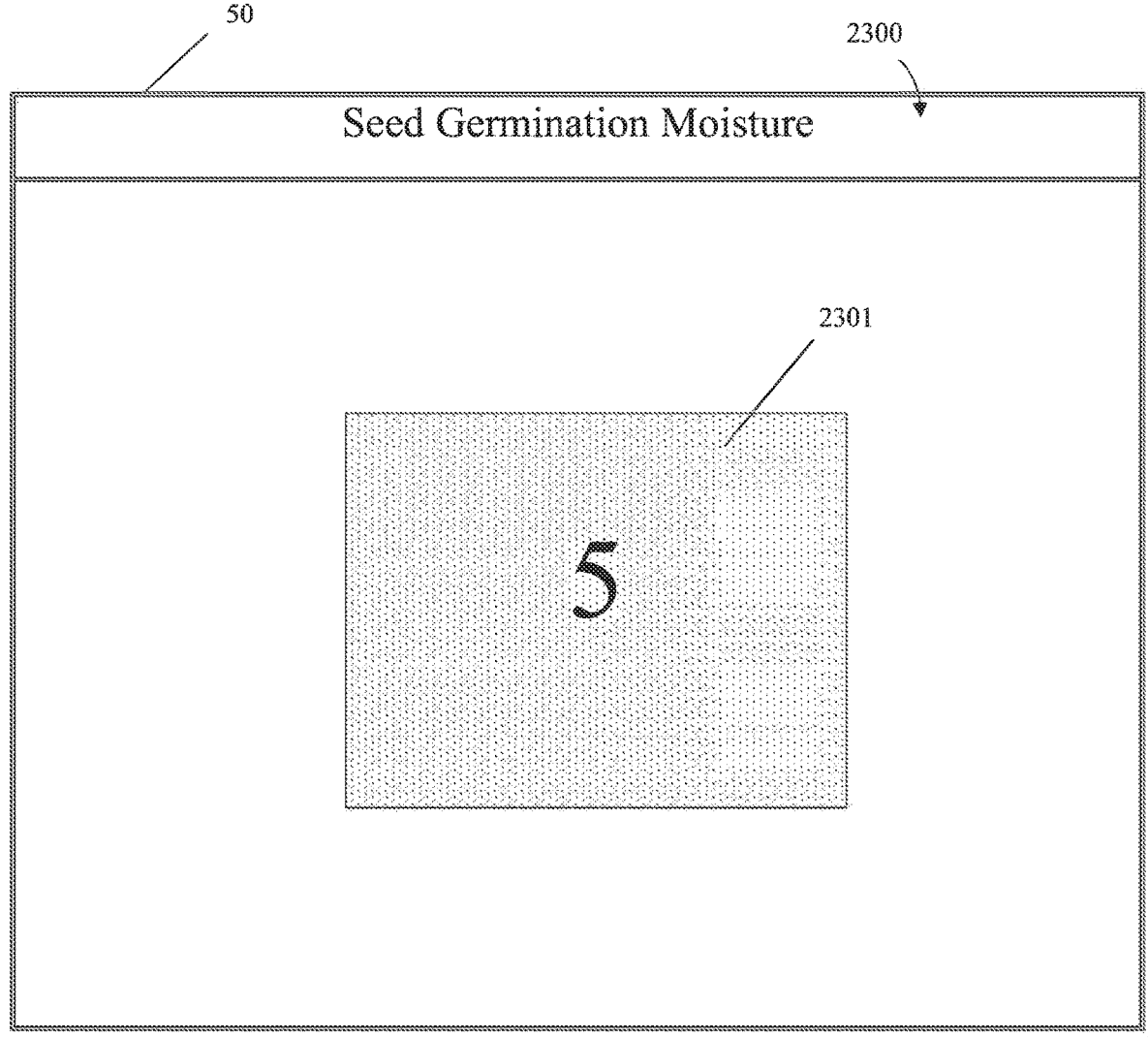
FIG. 45 illustrates an embodiment of a seed germination moisture screen.

In another embodiment, the reflectivity measurement from reflectivity sensor 350 allows for a seed germination moisture value to be obtained from a data table and displayed to an operator on monitor 50. Seed germination moisture is a dimensionless measurement related to the amount of water that is available to a seed for each given soil type. For different types of soil, water is retained differently. For example, sandy soil does not hold onto water as much as clay soil does. Even though there can be more water in clay than sand, there can be the same amount of water that is released from the soil to the seed. Seed germination moisture is a measurement of weight gain of a seed that has been placed in soil. Seed is placed in soil for a sufficient period of time to allow moisture to enter the seed. In one embodiment, three days is the period. The weight of the seed before and after is measured. Also, the reflectivity of soils at different water contents is stored in a data table. A scale of 1 to 10 can be used. Numbers in the middle of the scale, such as 4-7, can be associated with water contents in each soil type that is an acceptable level of water for seeds. Low numbers, such as 1-3, can be used to indicate that soil is too dry for the seed. High numbers, such as 8-10, can be used to indicate that soil is too wet for the seed. Knowing the soil type as input by the operator and the measured reflectivity, seed germination moisture can be obtained from the data table. The result can be displayed on monitor 50 with the actual number. Also, the result can be accompanied by a color. For example, the font color of the reported result or the screen color on monitor 50 can use green for values within the acceptable level and another color, such as yellow or red, for values that are high or low. An example of monitor 50 displaying on screen 2300 seed germination moisture 2301 is illustrated in FIG. 45. Alternatively, seed generation moisture 2301 can be displayed on monitor 50 in FIG. 20. Also, a uniform moisture can be displayed on monitor 50 (not shown). Uniform moisture is the standard deviation of seed germination moisture.

Depending on the seed germination moisture reading, the depth of planting can be adjusted as described herein. If the seed germination moisture is indicating too dry of conditions, then the depth can be increased to go deeper until a specified moisture level is achieved. If the seed germination moisture is indicating too moist, then the depth can be decreased to go shallower until a specified moisture level is achieved.

Figure 50:
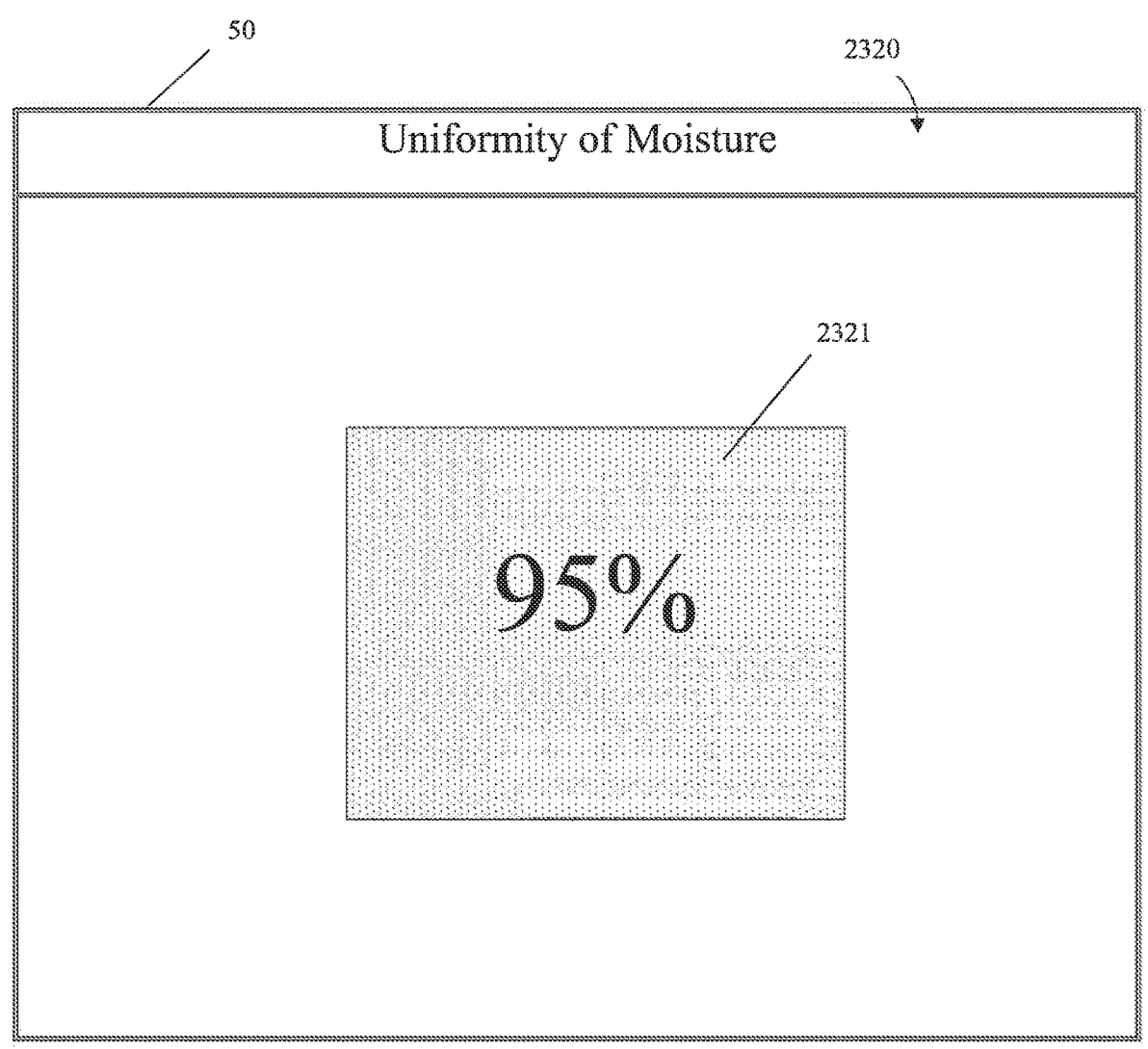
FIG. 50 illustrates an embodiment of a uniformity of moisture screen.
Figure 51:
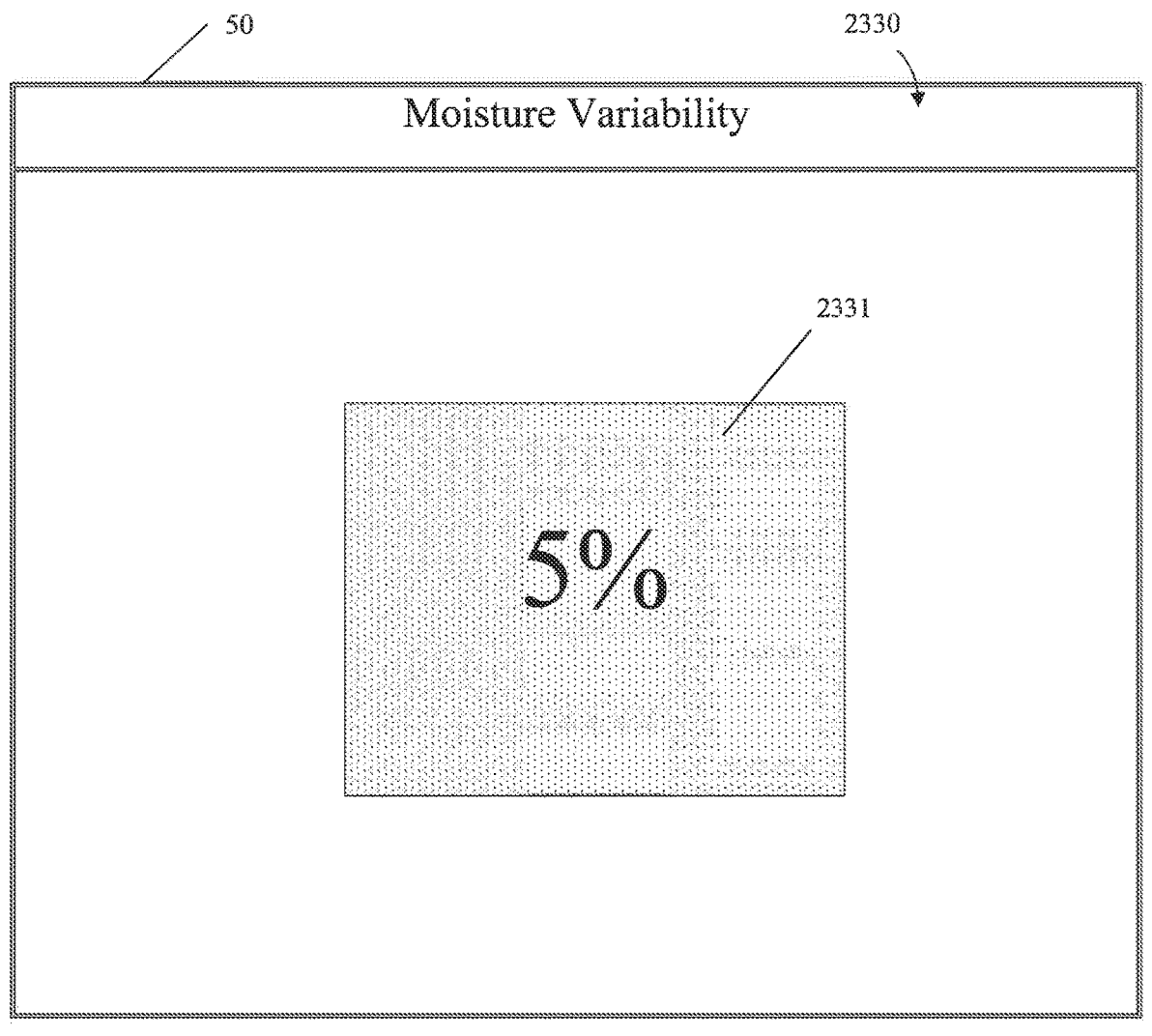
FIG. 51 illustrates an embodiment of a moisture variability screen.

In another embodiment, the uniformity of moisture or moisture variability can be measured and displayed on monitor 50. An example of monitor 50 displaying on screen 2320 uniformity of moisture 2321 and/or displaying on screen 2330 moisture variability 2331 are illustrated in FIGS. 50 and 51. One or both can be displayed, or both can be displayed on the same screen. Uniformity of moisture is 1—moisture variability. Any of the moisture readings can be used, such as capacitance moisture, seed germination moisture, or even volumetric water content or matrix potential or days until germination, to calculate uniformity of moisture and moisture variability. Moisture variability is deviation from the average measurement. In one embodiment, moisture variability is calculated by dividing the standard deviation by the average using any of the moisture measurements. This provides a percentage. Any other mathematical method for expressing variation in measurement can also be used. In one embodiment, root mean square can be used in place of the standard deviation. In addition to displaying the result on monitor 50, the result can be accompanied by a color. For example, the font color of the reported result or the screen color on monitor 50 can use green for values within the acceptable level and another color, such as yellow or red, for values that are unacceptable. For the above days to germination, this is determined by creating a database by placing seeds in different moisture levels and measuring the days until germination. Uniformity of moisture and moisture variability is then the variability in the days until germination.

Depending on the uniformity of moisture reading or moisture variability reading, the depth of planting can be adjusted as described herein. In one embodiment, depth can be adjusted to maximize uniformity of moisture and minimize moisture variability.

Figure 52:
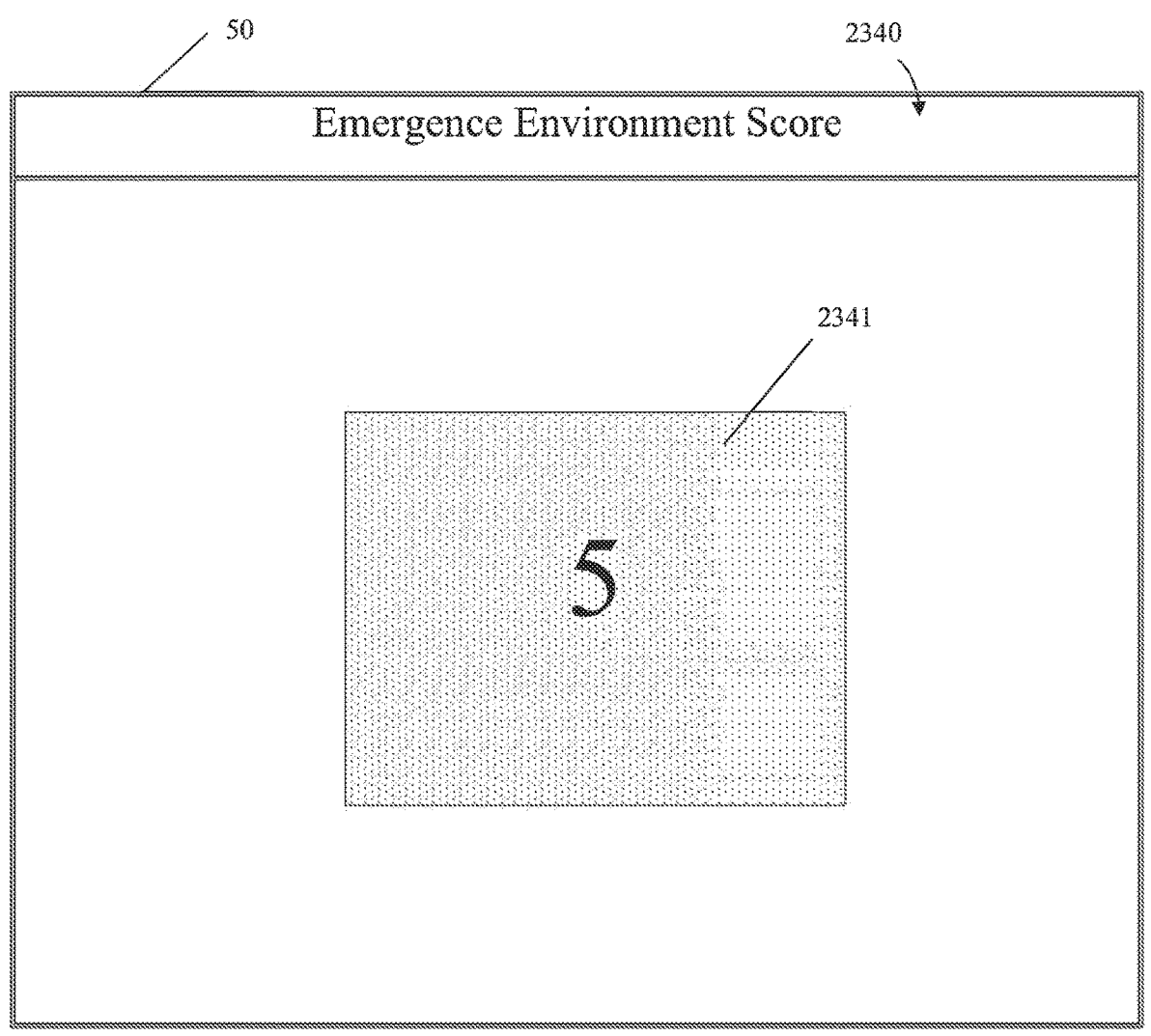
FIG. 52 illustrates an embodiment of an emergence environment score.

In another embodiment, an emergence environment score can be calculated and displayed on monitor 50. An example of monitor 50 displaying on screen 2340 an emergence environment score 2341 is illustrated in FIG. 52. The emergence environment score is a combination of temperature and moisture correlated to how long a seed takes to germinate under these conditions. A database can be created by placing seeds in different combinations of temperature and moisture and measuring the days until germination. The emergence environment score displayed on monitor 50 can be the days until germination from the database. In another embodiment, the emergence environment score can be the percentage of seeds planted that will germinate within a selected number of days. The selected number of days can be input into monitor 50. In another embodiment, a scaled score can be used that is based on a scale of 1 to 10 with 1 representing the shortest number of days that a seed takes to germinate and 10 representing the longest number of days that a seed takes to germinate. For example, if a seed can germinate within 2 days, this is assigned a value of 1, and if the longest that the seed takes to germinate is 17 days, this is assigned a value of 10. In addition to displaying the result on monitor 50, the result can be accompanied by a color. For example, the font color of the reported result or the screen color on monitor 50 can use green for values within the selected number of days and another color, such as yellow or red, for values that are greater than the selected number of days.

Depending on the emergence environment score, the depth of planting can be adjusted as described herein. In one embodiment, depth can be adjusted to minimize the number of days to germination.

In another embodiment, a uniform furrow score can be calculated with a processing unit (e.g., processing unit of soil apparatus, implement, tractor, monitor, computer, etc.). Uniform Furrow can be calculated based on one or more of moisture, temperature, residue, soil clods, tillage differences for different soil regions, and row unit issues. Row unit issues can be a seized opener discs 244, loose gauge wheels 248 (which can cause dry soil to fall into the furrow), or clogged closing system 236. Row unit issues can cause the sensor implement (such as firmer 400, 400') to rise out of the furrow, and this is detected by sensing an increase in ambient light. Uniform Furrow can be calculated as Uniform Furrow=100%−(% voids+% out of trench+% moisture variation). This is done for a selected amount of time, such as 200 ms. In one example, % voids is the % of time during a certain window (e.g., 200 ms window) that the height off target (which can be at the 850 nm) is greater than a threshold (e.g., 0.15" (0.38 cm)). This can be triggered by clods or voids in the soil. % out of trench is the time (or % of time in a window) that ambient light is detected with a sensor implement or height off target is greater than a threshold (e.g., greater than 0.4" (1 cm)). % moisture variation is based on the absolute value of a difference that the 1200 nm/1450 nm reflectance ratio varies by more than a specified amount, such as 0.01 to 0.5, from the running average of the 1200 nm/1450 nm reflectance ratio. In one example, the % moisture variation is % of time in a window (e.g., 200 ms window) that the 1200 nm/1450 nm reflectance ratio varies by more than a specified amount and can be calculated based on [abs(1200 nm instant reflection/1450 nm instant reflection)−(1200 nm running average reflection/1450 nm running average reflection)]. In other embodiments, the specified amount is 0.1 to 0.25, greater than or equal to about 0.15, 0.01 to 0.05, or greater than or equal to about 0.07. When the calculated value is above the specified amount, then a value of 1 is subtracted from the value of Uniform Furrow each time this occurs in the time window (e.g., 200 ms time window). Running average can be a is moving average. Instant reflection is values captured in a range of 500 Hz to 5 kHz.

In another embodiment, % moisture variation can be calculated as follows with a processing unit (e.g., processing unit of soil apparatus, implement, tractor, monitor, computer, etc.). First an estimated reflectance for dry soil at 1450 nm is calculated as E1450 dry=1200 nm reflectance*2–850. Moisture indicator is then (1450 actual–E1450 dry)/(1450 actual+E1450 dry), and then selected value is abs[moisture indicator (using instant reflectance values)–moisture indicator (using running average reflectance values)]. In certain embodiments using this formula, for a selected value greater than or equal to 0.07, a value of 1 is subtracted from the value of Uniform Furrow each time this occurs in the 200 ms time window.

In another embodiment, predicted air temperature can be used to determine whether planted seeds will experience a ground temperature that is less than or greater than a desired temperature for effective planting at a point in time after planting. For example, 50° F. (10° C.) can be considered the minimum temperature for planting so that the seed will germinate. Even though the soil temperature could be above this minimum temperature as the seed is planted, future weather could cause the soil temperature to drop below the minimum temperature. Soil temperature tends to follow air temperature. At a specific point in time, e.g. 10 AM, soil temperature and air temperature can be measured to obtain a temperature offset 7999. Predicted air temperature can be obtained with a network interface and downloaded from a weather service into memory, such as in monitor 50 or memory 1205 of FIG. 79. Using the offset temperature 7999 that is calculated with monitor 50 or with a processing system (e.g., 1220, 1262), predicted soil temperature can be obtained from the predicted air temperature. This is illustrated in FIG. 67. An alarm can be set with the monitor 50 or processing system if the soil temperature will be below the minimum soil temperature, greater than the maximum soil temperature, or deviate by a defined amount from an average temperature at a point in time in the future.

In addition to future temperature, future weather can also be downloaded (or input manually) and used to determine planting depth in combination with current moisture in the soil, current temperature in the soil, the type of soil (e.g., sand, silt, and/or clay), and combinations thereof. Current moisture can be based on the quantity of water in the soil, matric potential of water in the soil, or Seed Germ Moisture. Future weather can be air temperature, rainfall, wind speed, wind direction, solar radiation (amount of cloudiness), and combinations thereof. It is desired to have a moisture and temperature for the seed during germination and/or emergence that are in an acceptable range for the seed to germinate and/or emerge. The combination of current conditions and predicted weather can be used to determine planting depth. For soil type, different soils will respond differently to added water (such as from rain). Depending on the holding capacity of the soil, added rainfall will be retained in the soil, flow through the soil, or run off. So not only knowing the current moisture, the future rainfall, and the holding capacity of the specific type of soil, a future moisture can be calculated. Future soil temperature and future soil moisture will change based on future wind speed and/or future cloud cover. Wind speed will change the evaporative rate of the soil and the temperature of soil. Cloud cover (or amount of sunshine) will also change the evaporative rate of the soil and the temperature of soil.

Figure 69:
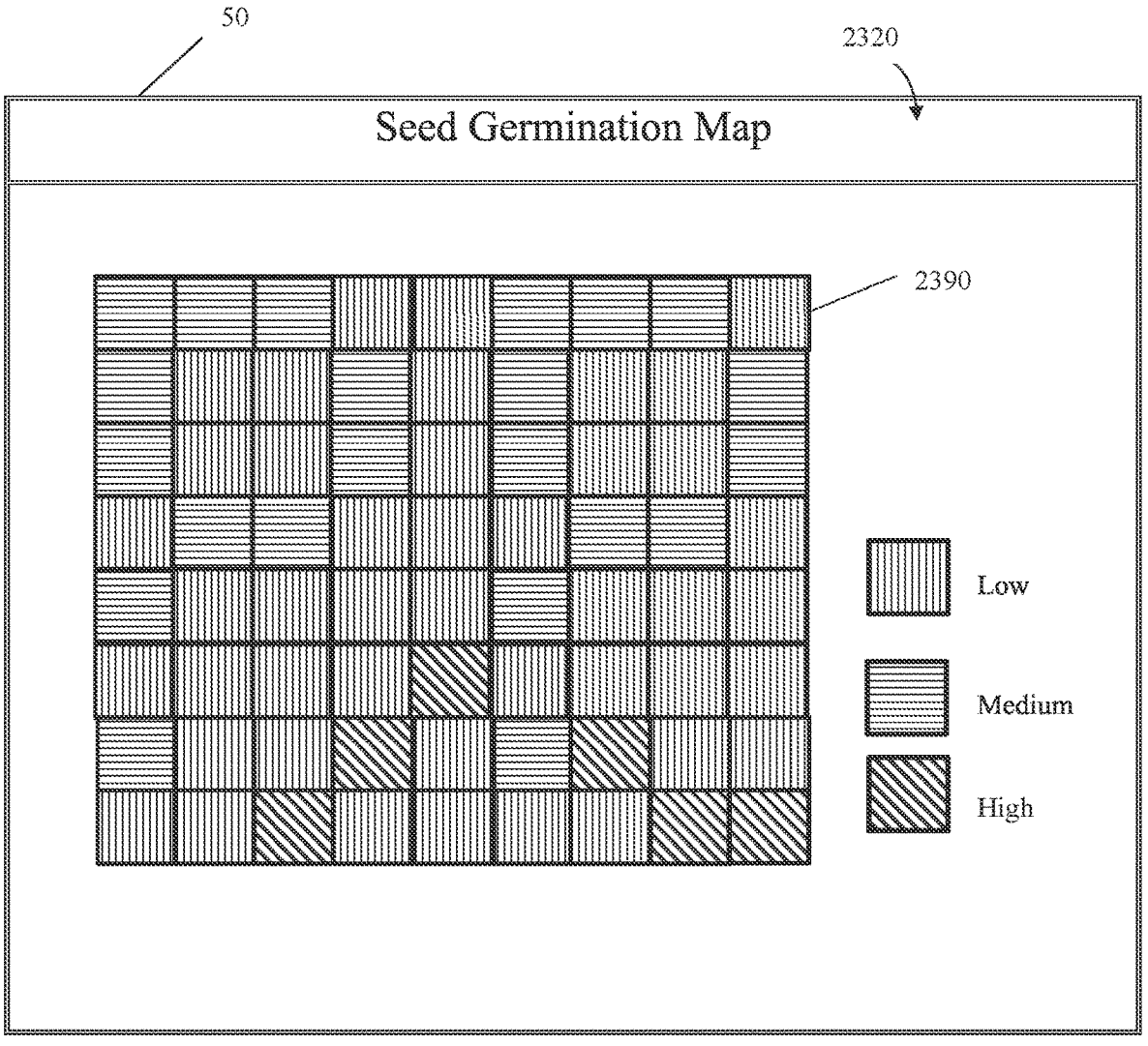
FIG. 69 illustrates an embodiment of a seed germination map.

In another embodiment, seed germination data and a seed germination map can be calculated with a processing unit (e.g., processing unit of soil apparatus, implement, tractor, monitor, computer, etc.) and displayed on monitor 50 or a display device. An example of monitor 50 displaying on screen 2320 a seed germination map/score 2390 is illustrated in FIG. 69. It can be one or more of time to germination, time to emergence, or germination risk. Time to germination and time to emergence can be expressed in hours or days. Time can be blocked together into ranges and represented by different colors, shapes, patterns, etc. In one embodiment, time to germination can be expressed in hours such as 0 to 8 hours (assigned a green color), 8 to 16 hours (assigned a yellow color), 16 to 24 hours (assigned an orange color), and greater than 24 hours (assigned a red color). Seed germination risk can be germination/emergence (no germination/emergence, on time germination/emergence, or late germination/emergence) or factors other than time, such as, deformities, damaged seed, reduced vigor, or disease. Seed germination risk can be high, medium, or low, or it can be on-time emergence, late emergence, or no emergence. Colors, shapes, patterns, etc. can be assigned to each of these. For example, low risk can be green, medium risk, can be yellow, and high risk can be red. To calculate the seed germination map/score, one or more (or two or more) of the following measurements can be measured: soil moisture (quantity of water in the soil, matric potential of water in the soil, seed germ moisture), soil temperature, soil organic matter, uniform furrow, furrow residue, soil type (sand, silt, clay), and residue cover (amount, location, distribution, and pattern of old and current crop matter on the soil surface). A database can be created by placing seeds in different combinations of these conditions to measure time to germination, time to emergence, and seed germination risk. This database can then be accessed during planting as the properties are acquired to then provide time to germination, time to emergence, or seed germination risk.

In other embodiments, below is a table relating measured properties (some listed above), each of the property's impact on seed germination and/or emergence; how the property is measured; output of the information as raw data, seed environment score, time to germination, time to emergence, and/or seed germination risk; and actuation of equipment or action to take. Note, a Stop Planting Action may be listed below for a Measured Property for which Stop Planting alone may not be taken, but Stop Planting may be an action for this Measured Property in combination with one or more other Measured Properties. For example, soil color alone may not be a reason to stop planting, but soil color in combination with other Measured Properties may result in a Stop Planting Action. This can also be the situation for other actions, such as Row Cleaner Aggressiveness.

| Measured Property | Impact on germination/ emergence | How Measured | Output | Actuation/ Action |
|---|---|---|---|---|
| Soil Color | Radiative heat absorption | Seed firmer 400, 400' Imagery | Raw data | Adjust depth |
| | | | Days to Germination | Adjust downforce |
| | | | Days to Emergence | Hybrid selection |
| | | | Seed Germination Risk | Row cleaner |
| | | | Seed Environment Score | aggressiveness |
| | | | | Stop planting |

-continued

| Measured Property | Impact on germination/ emergence | How Measured | Output | Actuation/ Action |
|---|---|---|---|---|
| Residue | Radiative heat absorption Residue in furrow Seed environment quality | Seed firmer 400, 400' Imagery | Raw data Days to Germination Days to Emergence Seed Germination Risk Seed Environment Score | Row cleaner aggressiveness Adjust depth Adjust downforce |
| Topography | Watershed runoff or infiltration | Reference source | Raw data Days to Germination Days to Emergence Seed Germination Risk Seed Environment Score | Adjust depth Adjust downforce Row cleaner aggressiveness Stop planting |
| Soil Texture/Type | Water holding capacity Seed imbibing rate Thermal insulative factor | Seed firmer 400, 400' Imagery | Raw data Days to Germination Days to Emergence Seed Germination Risk Seed Environment Score | Adjust depth Adjust downforce Hybrid selection Row cleaner aggressiveness Stop planting |
| Organic Matter | Water holding capacity Seed imbibing rate Thermal insulative factor | Seed firmer 400, 400' Imagery | Raw data Days to Germination Days to Emergence Seed Germination Risk Seed Environment Score | Adjust depth Adjust downforce Population Hybrid selection Row cleaner aggressiveness Stop planting |
| Soil Temperature | Impact on germination | Seed firmer 400, 400' | Raw data Days to Germination Days to Emergence Seed Germination Risk Seed Environment Score | Adjust depth Adjust downforce Population Stop planting Row cleaner aggressiveness |
| Soil Moisture | Impact on germination | Seed firmer 400, 400' | Raw data Days to Germination Days to Emergence Seed Germination Risk Seed Environment Score | Adjust depth Adjust downforce Population Stop planting Row cleaner aggressiveness |
| Seed Shape/Size | Volume of water to germinate | User input | Raw data Days to Germination Days to Emergence Seed Germination Risk Seed Environment Score | Adjust depth Adjust downforce Hybrid selection Row cleaner aggressiveness Stop planting |
| Seed Cold Germ | Risk of no germination based on temperature | User input | Raw data Days to Germination Days to Emergence Seed Germination Risk Seed Environment Score | Adjust depth Adjust downforce Hybrid selection Row cleaner aggressiveness Stop planting |
| Time of Day | Bias of current temperature, moisture | Monitor | Raw data | N/A |
| Furrow Depth | Insulative effect of soil, Time required to emerge from this depth | Depth Actuator/ Depth Sensor | Raw data Days to Germination Days to Emergence Seed Germination Risk Seed Environment Score | Adjust depth Adjust downforce Row cleaner aggressiveness Stop planting |
| Temperature Forecast | Temperature impact on germination | Weather source | Raw data Days to Germination Days to Emergence Seed Germination Risk Seed Environment Score | Adjust depth Adjust downforce Population Hybrid selection Stop planting Row cleaner aggressiveness |
| Precipitation Forecast | Moisture impact on germination | Weather source | Raw data Days to Germination Days to Emergence Seed Germination Risk Seed Environment Score | Adjust depth Adjust downforce Population Hybrid selection Stop planting Row cleaner aggressiveness |
| Wind Speed Forecast | Thermal and evaporative impact on soil temperature and/or moisture | Weather source | Raw data Days to Germination Days to Emergence Seed Germination Risk Seed Environment Score | Adjust depth Adjust downforce Population Hybrid selection Stop planting Row cleaner aggressiveness |

-continued

| Measured Property | Impact on germination/ emergence | How Measured | Output | Actuation/ Action |
|---|---|---|---|---|
| Cloud Cover Forecast | Thermal and evaporative impact on soil temperature and/or moisture | Weather source | Raw data Days to Germination Days to Emergence Seed Germination Risk Seed Environment Score | Adjust depth Adjust downforce Population Hybrid selection Stop planting Row cleaner aggressiveness |

Residue coverage and soil color can be obtained from imagery. Imagery can be obtained from a satellite or an aircraft, such as a drone, or from a camera disposed over the field, such as on a pole. For user input of seed shape/size or cold germ, a user can input this information directly, a user can scan a code (bar code or QR code from a package), or a user can input the specific type of seed (or scan a code), and then the size, shape, and cold germ can be referenced from a database based on the seed type. The reference source for topography can be from stored information, such as a map, that was previously measured. Any method of measuring topography can be used. As an alternative to adjusting depth, downforce can be adjusted to effect a change in depth, or row cleaner aggressiveness can be changed.

Figure 71:
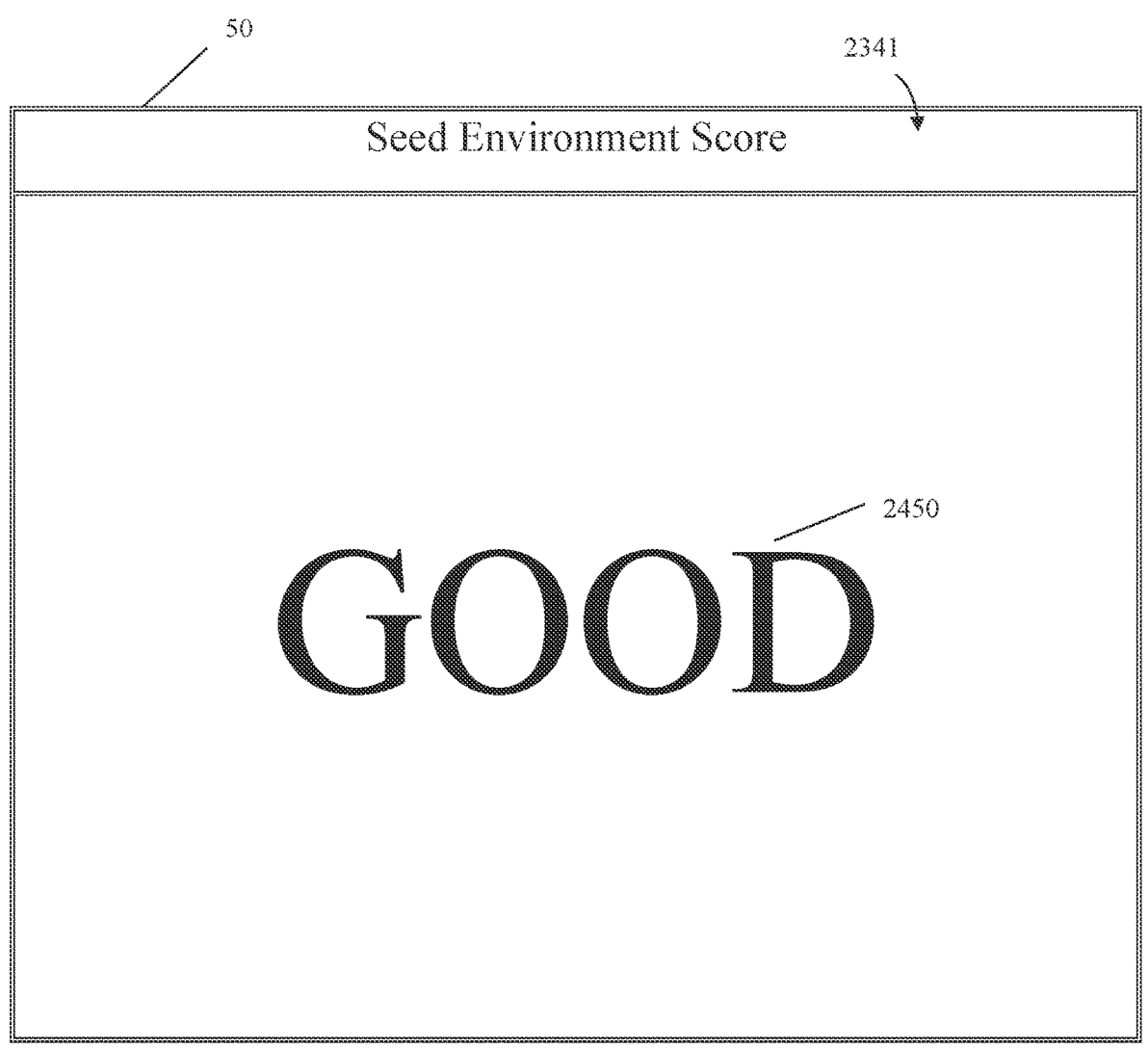
FIG. 71 illustrates an embodiment of a seed environment score screen.

In another embodiment, seed environment data and a seed environment score 2450 can be calculated with a processing unit (e.g., processing unit of soil apparatus, implement, tractor, monitor, computer, etc.) and displayed on monitor 50 or a display device (e.g., display device 1225 or 1230). An example of monitor 50 or display device displaying on screen 2341 a seed environment score 2450 is illustrated in FIG. 71. It can be a display of "Good" or "Bad" or similar status indicator to indicate whether the soil conditions are currently ready for planting and optionally whether the soil conditions will remain acceptable through at least germination and optionally emergence. The seed environment score 2450 can be a score based on one or more properties from the table above that lists an output to seed environment score. If the one or more properties that are measured will be within a selected range during the time selected (e.g., one or more of at planting, at germination, and at emergence), the seed environment score 2450 can display a status that planting can occur, such as Good or OK. If one or more of the properties that are measured will be outside of the selected range during the time selected, then the seed environment score 2450 can display a status that planting should not occur, such as Bad or Unacceptable. Also, a color, such as green or red can be associated with the status. If a negative status is displayed, such as Bad or Unacceptable, a user can review one or more of the properties on a Seed Environment Score Properties 2342 screen on monitor 50. The value of each property can be displayed, and optionally, an indication of whether the property is within an acceptable range can be displayed. An example of a Seed Environment Properties 2342 screen is illustrated in FIG. 72.

Figure 46:
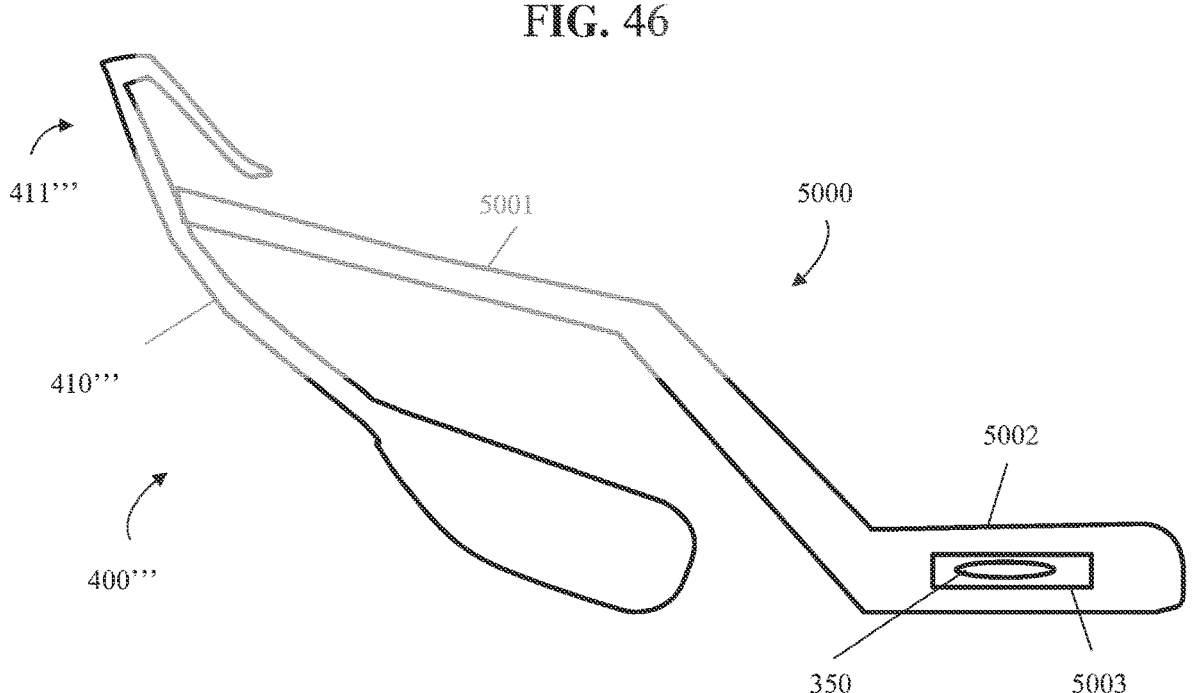
FIG. 46 is a side view of a seed firmer and sensor arm according to one embodiment.

In another embodiment, any of the previous embodiments can be in a device separate from seed firmer 400, 400'. As illustrated in FIG. 46, any of the sensors described herein (sensor 350 is illustrated in the Figure) is disposed in sensor arm 5000. Sensor arm 5000 has flexible portion 5001 that is attached to seed firmer 400' at an end of flexible portion 410''' of seed firmer 400' proximate to bracket insert portion 411'''. At the opposite end of flexible portion 5001 is base 5002. Sensor 350 is disposed in base 5002 behind lens 5003.

While it is desirable for any of the sensors to be in seed firmer 400', there may be times when a difference in the applied force is needed. In one embodiment, seed firmer 400''' may need a lower amount of force to firm a seed but a greater force is needed to keep the sensor in soil contact. A different amount of stiffness can be designed into flexible portion 5001 as compared to flexible portion 410'. By having the seed firmed by seed firmer 400, 400' first, then the biasing from sensor arm 5000 does not touch the seed that is already firmed into trench 38 or does not move the seed if contact is made.

In other embodiments, any of the sensors do not need to be disposed in a firmer, and in particular any of the embodiments illustrated in FIGS. 27A to 54. The sensors can be in any implement that is disposed on an agricultural implement in contact with the soil. For example, firmer body 490 can be mounted to any bracket and disposed anywhere on an agricultural implement and in contact with soil. Examples of an agricultural implement include, but are not limited to, planters, harvesters, sprayers, side dress bars, tillers, fertilizer spreaders, and tractor.

FIG. 49 illustrates a flow diagram of one embodiment for a method 4900 of obtaining soil measurements and then generating a signal to actuate any implement on any agricultural implement. The method 4900 is performed by hardware (circuitry, dedicated logic, etc.), software (such as is run on a general purpose computer system or a dedicated machine or a device), or a combination of both. In one embodiment, the method 4900 is performed by at least one system or device (e.g., monitor 50, soil monitoring system, seed firmer, sensors, implement, row unit, etc). The system executes instructions of a software application or program with processing logic. The software application or program can be initiated by a system or may notify an operator or user of a machine (e.g., tractor, planter, combine) depending on whether soil measurements cause a signal to actuate an implement.

In any embodiment herein, at operation 4902, a system or device (e.g., soil monitoring system, monitor 50, seed firmer, sensors) can obtain soil measurements (e.g., measurements for moisture, organic matter, porosity, texture/type of soil, furrow residue, etc.). At operation 4904, the system or device (e.g., soil monitoring system, monitor 50) can generate a signal to actuate any implement on any agricultural implement (e.g., change a population of planted seeds by controlling a seed meter, change seed variety (e.g., hybrid), change furrow depth, change application rate of fertilizer, fungicide, and/or insecticide, change applied downforce or upforce of an agricultural implement, such as a planter or tiller, control the force applied by a row cleaner) in response to obtaining soil measurements. This can be done in real time on the go. Examples of soil measurements that can be measured and the control of implements include, but are not limited to:

A) moisture, organic matter, porosity, or texture/type of soil to change a population of planted seeds by controlling a seed meter;

B) moisture, organic matter, porosity, or texture/type of soil to change seed variety (e.g., hybrid);

C) moisture, organic matter, porosity, or texture/type of soil to change furrow depth:

D) moisture, organic matter, porosity, or texture/type of soil to change application rate of fertilizer, fungicide, and/or insecticide;

E) moisture, organic matter, porosity, or texture/type of soil to change applied downforce or upforce of an agricultural implement, such as a planter or tiller;

F) furrow residue to control the force applied by a row cleaner.

In one embodiment for downforce or upforce, a combination of moisture and texture/type can be used. Higher downforce can be applied in sandy and/or wet soils, and lower downforce can be used in clay and/or wet soils. Too much downforce for a given soil type can cause compaction of the soil, which decreases the ability of roots to spread throughout the soil. Too little downforce for a given soil type can allow an implement to ride up and not plant seeds to a targeted depth. The downforce is generally applied through the gauge wheels 248 adjacent to the trench.

Data Processing and Display

Figure 20:
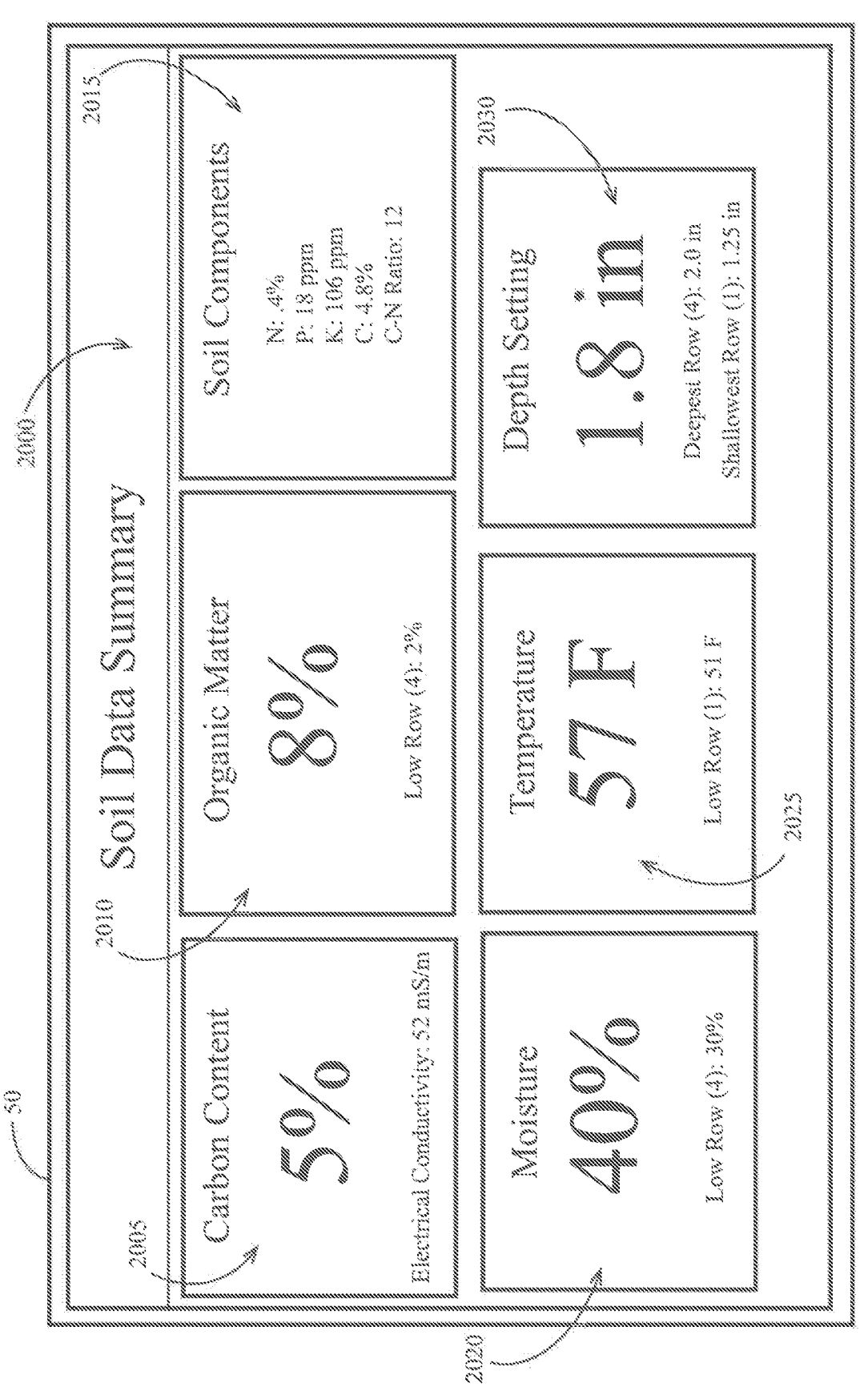
FIG. 20 illustrates an embodiment of a soil data display screen.

Referring to FIG. 20, the implement monitor 50 or display device may display a soil data summary 2000 displaying a representation (e.g., numerical or legend-based representation) of soil data gathered using the seed firmer 400 and associated sensors. The soil data may be displayed in windows such as a soil moisture window 2020 and soil temperature window 2025. A depth setting window 2030 may additionally show the current depth setting of the row units of the implement, e.g., the depth at which the seed firmers 400 are making their respective measurements. A reflectivity variation window may show a statistical reflectivity variation during a threshold period (e.g., the prior 30 seconds) or over a threshold distance traveled by the implement (e.g., the preceding 30 feet). The statistical reflectivity variation may comprise any function of the reflectivity signal (e.g., generated by each reflectivity sensor 350) such as the variance or standard deviation of the reflectivity signal. The monitor 50 may additionally display a representation of a predicted agronomic result (e.g., percentage of plants successfully emerged) based on the reflectivity variation value. For example, values of reflectivity emergence may be used to look up a predicted plant emergence value in an empirically-generated database (e.g., stored in memory of the implement monitor 50 or stored in and updated on a remote server in data communication with the implement monitor) associating reflectivity values with predicted plant emergence.

Each window in the soil data summary 2100 preferably shows an average value for all row units ("rows") at which the measurement is made and optionally the row unit for which the value is highest and/or lowest along with the value associated with such row unit or row units. Selecting (e.g., clicking or tapping) each window preferably shows the individual (row-by-row) values of the data associated with the window for each of the row units at which the measurement is made.

A carbon content window 2005 preferably displays an estimate of the soil carbon content. The carbon content is preferably estimated based on the electrical conductivity measured by the electrical conductivity sensors 370, e.g., using an empirical relation or empirical look-up table relating electrical conductivity to an estimated carbon content percentage. The window 2005 preferably additionally displays the electrical conductivity measured by the electrical conductivity sensors 370.

An organic matter window 2010 preferably displays an estimate of the soil organic matter content. The organic matter content is preferably estimated based on the reflectivity at one or a plurality of wavelengths measured by the reflectivity sensors 350, e.g., using an empirical relation or empirical look-up table relating reflectivity at one or a plurality of wavelengths to an estimated organic matter percentage.

A soil components window 2015 preferably displays an estimate of the fractional presence of one or a plurality of soil components, e.g., nitrogen, phosphorous, potassium, and carbon. Each soil component estimate is preferably based on the reflectivity at one or a plurality of wavelengths measured by the reflectivity sensors 350, e.g., using an empirical relation or empirical look-up table relating reflectivity at one or a plurality of wavelengths to an estimated fractional presence of a soil component. In some embodiments, the soil component estimate is preferably determined based on a signal or signals generated by the spectrometer 373. In some embodiments, the window 2015 additionally displays a ratio between the carbon and nitrogen components of the soil.

A moisture window 2020 preferably displays an estimate of soil moisture. The moisture estimate is preferably based on the reflectivity at one or a plurality of wavelengths (e.g., 930 or 940 nanometers) measured by the reflectivity sensors 350, e.g., using an empirical relation or empirical look-up table relating reflectivity at one or a plurality of wavelengths to an estimated moisture. In some embodiments, the moisture measurement is determined as disclosed in the '975 application.

A temperature window 2025 preferably displays an estimate of soil temperature. The temperature estimate is preferably based on the signal generated by one or more temperature sensors 350.

A depth window 2030 preferably displays the current depth setting. The monitor 50 preferably also enables the user to remotely actuate the row unit 200 to a desired trench depth as disclosed in International Patent Application No. PCT/US2014/029352.

Figure 21:
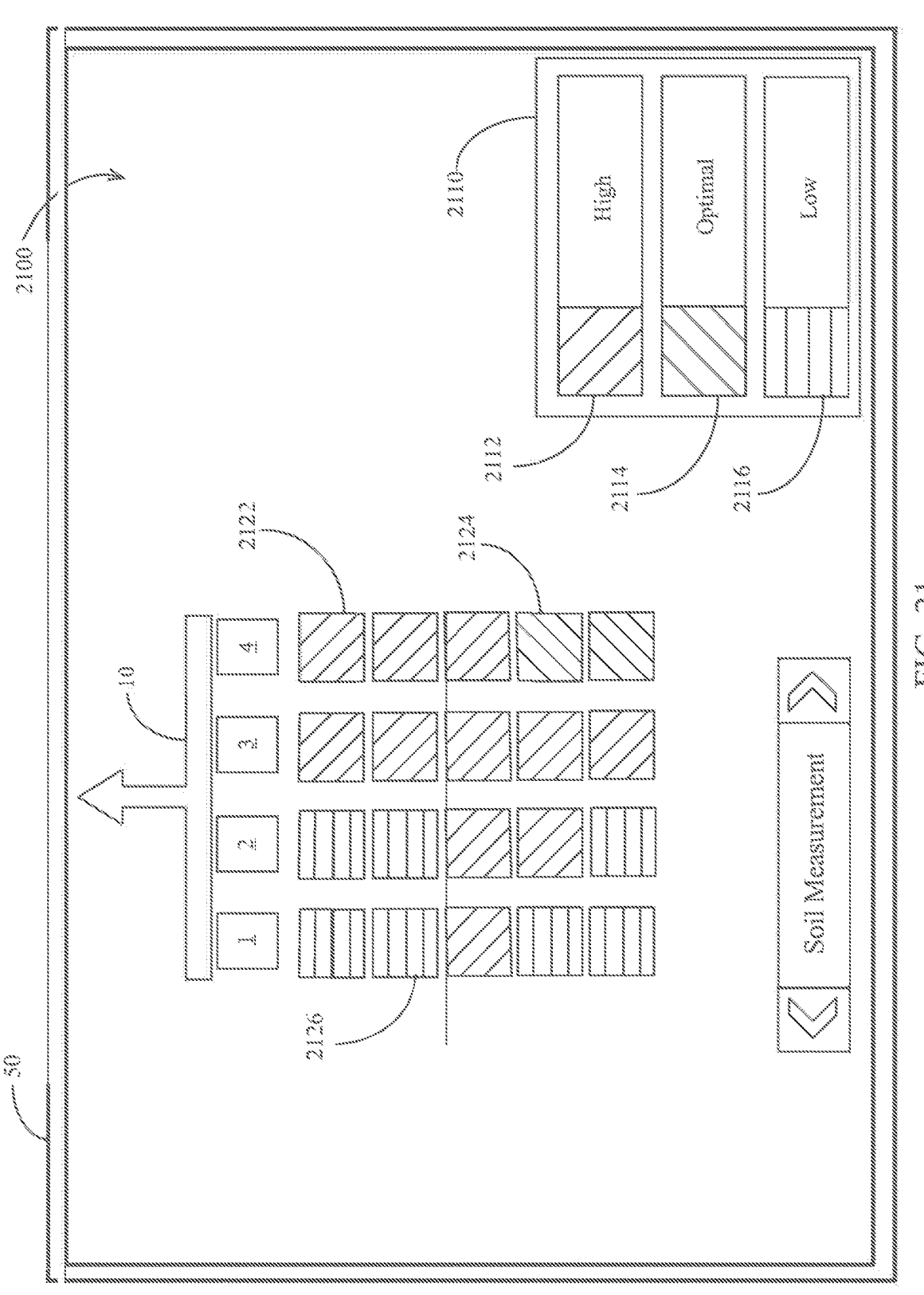
FIG. 21 illustrates an embodiment of a spatial map screen.

Turning to FIG. 21, the monitor 50 is preferably configured to display one or more map windows 2100 in which a plurality of soil data, measurement, and/or estimate values (such as the reflectivity variation) are represented by blocks 2122, 2124, 2126, each block having a color or pattern associating the measurement at the block position to the ranges 2112, 2114, 2116, respectively (of legend 2110) in which the measurements fall. A map window 2100 is preferably generated and displayed for each soil data, measurement, and/or estimate displayed on the soil data screen 2000, preferably including carbon content, electrical conductivity, organic matter, soil components (including nitrogen, phosphorous, and potassium), moisture and soil temperature. The subsets may correspond to numerical ranges of reflectivity variation. The subsets may be named according to an agronomic indication empirically associated with the range of reflectivity variation. For example, a reflectivity variation below a first threshold at which no emergence failure is predicted may be labeled "Good"; a reflectivity variation between the first threshold and a second threshold at which predicted emergence failure is agronomically unacceptable (e.g., is likely to affect yield by more than a yield threshold)

may be labeled "Acceptable"' a reflectivity variation above the second threshold may be labeled "Poor emergence predicted".

Figure 17:
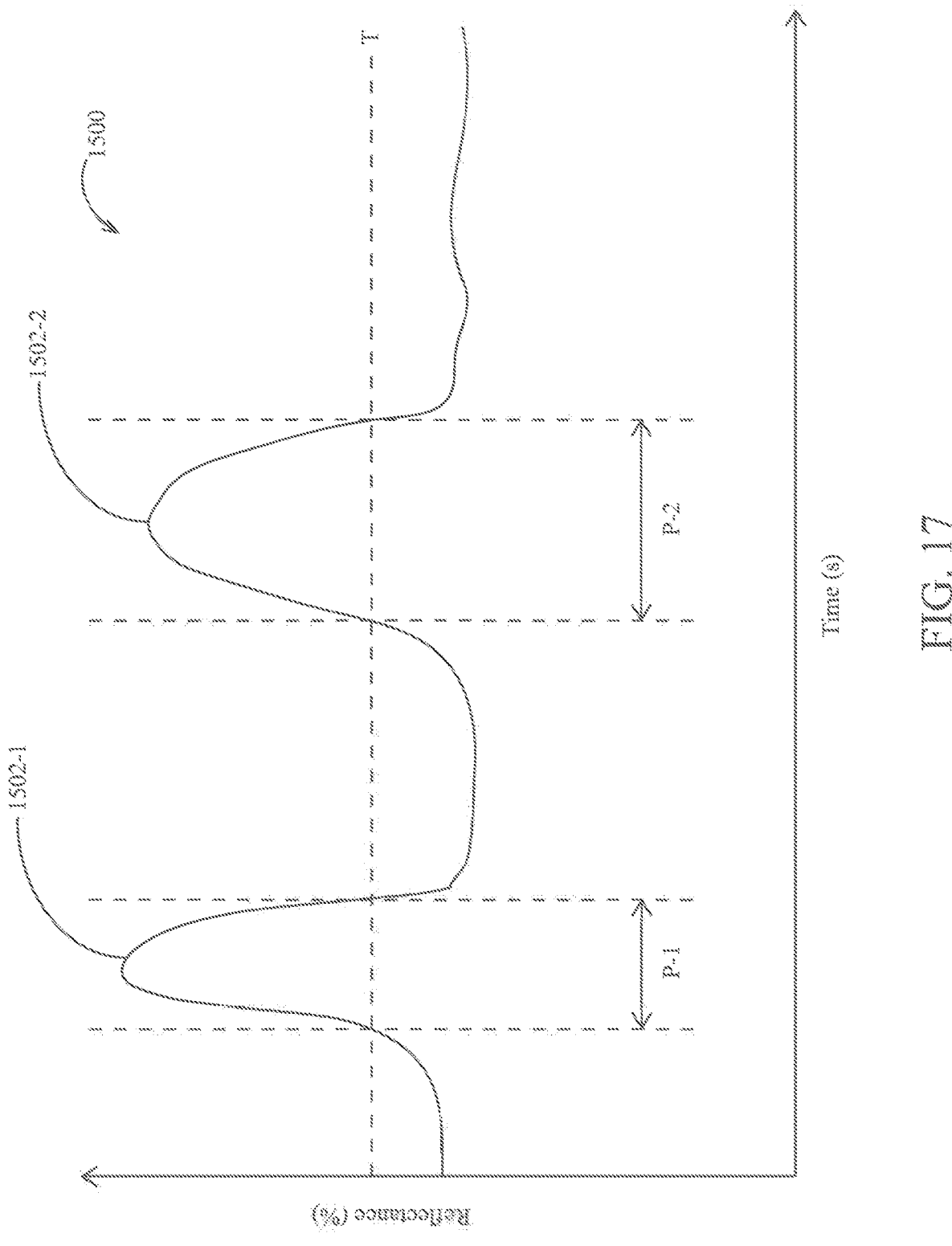
FIG. 17 is a plot of a reflectivity sensor signal.
Figure 22:
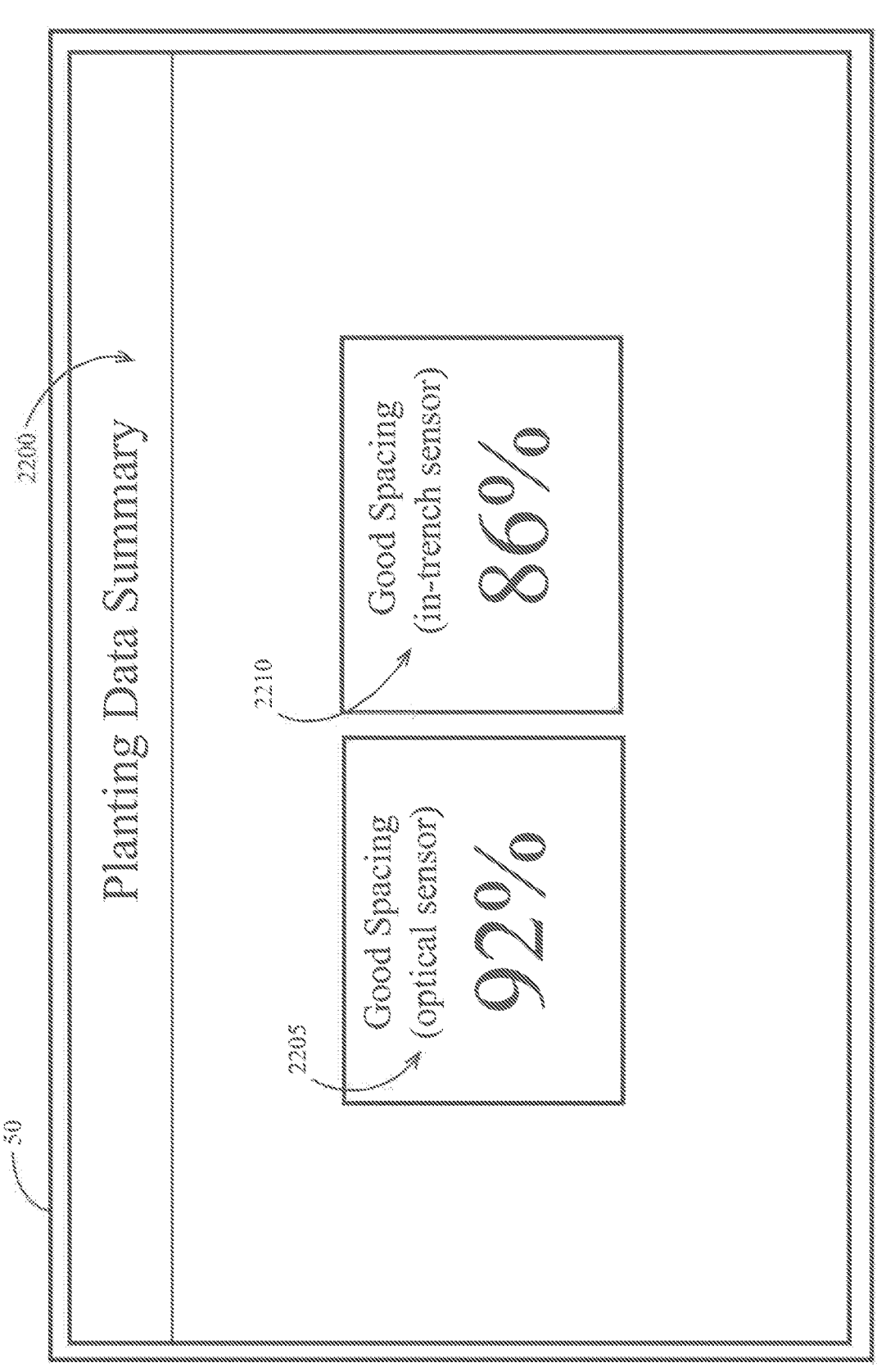
FIG. 22 illustrates an embodiment of a seed planting data display screen.

Turning to FIG. 22, the monitor 50 is preferably configured to display one or more planting data windows including planting data measured by the seed sensors 305 and/or the reflectivity sensors 350. The window 2205 preferably displays a good spacing value calculated based on seed pulses from the optical (or electromagnetic) seed sensors 305. The window 2210 preferably displays a good spacing value based on seed pulses from the reflectivity sensors 350. Referring to FIG. 17, seed pulses 1502 in a reflectivity signal 1500 may be identified by a reflectance level exceeding a threshold T associated with passage of a seed beneath the seed firmer. A time of each seed pulse 1502 may be established to be the midpoint of each period P between the first and second crossings of the threshold T. Once times of seed pulses are identified (whether from the seed sensor 305 or from the reflectivity sensor 350), the seed pulse times are preferably used to calculate a good spacing value as disclosed in U.S. patent application Ser. No. 13/752,031 ("the '031 application"). In some embodiments, in addition to good spacing other seed planting information (including, e.g., population, singulation, skips and multiples) is also calculated and displayed on the screen 2200 according to the methods disclosed in the '031 application. In some embodiments, the same wavelength (and/or the same reflectivity sensor 350) is used for seed detection as moisture and other soil data measurements; in some embodiments the wavelength is about 940 nanometers. Where the reflectivity signal 1500 is used for both seed detection and soil measurement (e.g., moisture), the portion of the signal identified as a seed pulse (e.g., the periods P) are preferably not used in calculating the soil measurement; for example, the signal during each period P may be assumed to be a line between the times immediately prior to and immediately following the period P, or in other embodiments it may be assumed to be the average value of the signal during the previous 30 seconds of signal not falling within any seed pulse period P. In some embodiments, the screen 2200 also displays a percentage or absolute difference between the good spacing values or other seed planting information determined based on seed sensor pulses and the same information determined based on reflectivity sensor pulses.

In some embodiments, seed sensing is improved by selectively measuring reflectivity at a wavelength or wavelengths associated with a characteristic or characteristics of the seed being planted. In some such embodiments, the system 300 prompts the operator to select a crop, seed type, seed hybrid, seed treatment and/or another characteristic of the seed to be planted. The wavelength or wavelengths at which reflectivity is measured to identify seed pulses is preferably selected based on the seed characteristic or characteristics selected by the operator.

In some embodiments, the "good spacing" values are calculated based on both the seed pulse signals generated by the optical or electromagnetic seed sensors 305 and the reflectivity sensors 350.

In some such embodiments, the "good spacing" value for a row unit is based on the seed pulses generated the reflectivity sensor 350 associated with the row unit, which are filtered based on the signal generated by the optical seed sensor 305 on the same row unit. For example, a confidence value may be associated with each seed pulse generated by the optical seed sensor, e.g., directly related to the amplitude of the optical seed sensor seed pulse; that confidence value may then be modified based on the optical seed sensor signal, e.g., increased if a seed pulse was observed at the optical seed sensor within a threshold period prior to the reflectivity sensor seed pulse, and decreased if the a seed pulse was not observed at the optical seed sensor within a threshold period prior to the reflectivity sensor seed pulse. A seed pulse is then recognized and stored as a seed placement if the modified confidence value exceeds a threshold.

In other such embodiments, the "good spacing" value for a row unit is based on the seed pulses generated the optical seed sensor 305 associated with the row unit, which are modified based on the signal generated by the reflectivity sensor 350 on the same row unit. For example, the seed pulses generated by the optical seed sensor 305 may be associated with the time of the next seed pulse generated by the reflectivity sensor 350. If no seed pulse is generated by the reflectivity sensor 350 within a threshold time after the seed pulse generated by the seed sensor 305, then the seed pulse generated by the seed sensor 305 may be either ignored (e.g., if a confidence value associated with the seed sensor seed pulse is below a threshold) or adjusted by an average time delay between reflectivity sensor seed pulses and seed sensor seed pulses (e.g., the average time delay for the last 10, 100 or 300 seeds).

In addition to displaying seed planting information such as good spacing values, in some embodiments the seed pulses measured may be used to time deposition of in-trench liquid and other crop inputs in order to time application such that the applied crop input lands on the seed, adjacent to the seed, or between seeds as desired. In some such embodiments, a liquid applicator valve selectively permitting liquid to flow from outlet 507 of the liquid conduit 506 is briefly opened a threshold time (e.g., 0 seconds, 1 ms, 10 ms, 100 ms or 1 second) after a seed pulse 1502 is identified in signal 1500 from the reflectivity sensor 350 associated with the same row unit 200 as the liquid applicator valve.

A signal generated by the reflectivity sensor may also be used to identify the presence of crop residue (e.g., corn stalks) in the seed trench. Where reflectivity in a range of wavelengths associated with crop residue (e.g., between 560 and 580 nm) exceeds a threshold, the system 300 preferably determines that crop residue is present in the trench at the current GPS-reported location. The spatial variation in residue may then be mapped and displayed to a user. Additionally, the downpressure supplied to a row cleaner assembly (e.g., a pressure-controlled row cleaner as disclosed in U.S. Pat. No. 8,550,020B2 may be adjusted either automatically by the system 300 in response to the identification of residue or adjusted by the user. In one example, the system may command a valve associated with a row cleaner downpressure actuator to increase by 5 psi in response to an indication that crop residue is present in the seed trench. Similarly, a closing wheel downforce actuator may also be adjusted by the system 300 or the operator in response to an indication that crop residue is present in the seed trench.

In some embodiments, an orientation of each seed is determined based on the width of reflectivity-based seed pulse periods P. In some such embodiments, pulses having a period longer than a threshold (an absolute threshold or a threshold percentage in excess of the mean pulse period) are categorized in a first category while pulses having a shorter period than the threshold are categorized in a second category. The first and second category preferably correspond to first and second seed orientations. Percentages of seeds over the previous 30 seconds falling in the first and/or second category may be displayed on the screen 2200. The orientation of each seed is preferably mapped spatially using the GPS coordinates of the seed such that individual plant performance may be compared to seed orientation during scouting operations.

In some embodiments, a determination of seed-to-soil contact is made based on the existence or lack of a recognized seed pulse generated by the reflectivity sensor 350. For example, where a seed pulse is generated by the optical seed sensor 305 and no seed pulse is generated by the reflectivity sensor 350 within a threshold time after the optical seed sensor seed pulse, a "Poor" seed-to-soil contact value is preferably stored and associated with the location at which the reflectivity sensor seed pulse was expected. An index of seed-to-soil contact may be generated for a row or rows by comparing the number of seeds having "Poor" seed-to-soil contact over a threshold number of seeds planted, distance traveled, or time elapsed. The operator may then be alerted via the monitor 50 as to the row or rows exhibiting seed-to-soil contact below a threshold value of the index. Additionally, the spatial variation in seed-to-soil contact may be mapped and displayed to the user. Additionally, a criterion representing the percentage of seeds firmed (e.g., not having "Poor" seed-to-soil contact) over a preceding time period or number of seeds may be displayed to the operator.

In one embodiment, the depth of planting can be adjusted based on soil properties measured by the sensors and/or camera so that seeds are planted where the desired temperature, moisture, and/or conductance is found in trench 38. A signal can be sent to the depth adjustment actuator 380 to modify the position of the depth adjustment rocker 268 and thus the height of the gauge wheels 248 to place the seed at the desired depth. In one embodiment, an overall goal is to have the seeds germinate at about the same time. This leads to greater consistency and crop yield. When certain seeds germinate before other seeds, the earlier resulting plants can shade out the later resulting plants to deprive them of needed sunlight and can disproportionately take up more nutrients from the surrounding soil, which reduces the yield from the later germinating seeds. Days to germination is based on a combination of moisture availability (soil moisture tension) and temperature.

In another embodiment, the depth can be adjusted based on a combination of current temperature and moisture conditions in the field and the predicted temperature and moisture delivery from a weather forecast. This process is described in U.S. Patent Publication No. 2016/0037709A1.

In any of the foregoing embodiments for depth control for moisture, the control can be further limited by a minimum threshold temperature. A minimum threshold temperature (for example 10° C. (50° F.)) can be set so that the planter will not plant below a depth where the minimum threshold temperature is. This can be based on the actual measured temperature or by accounting for the temperature measured at a specific time of day. Throughout the day, soil is heated by sunshine or cooled during night time. The minimum threshold temperature can be based on an average temperature in the soil over a 24 hour period. The difference between actual temperature at a specific time of day and average temperature can be calculated and used to determine the depth for planting so that the temperature is above a minimum threshold temperature.

The soil conditions of conductivity, moisture, temperature, and/or reflectance can be used to directly vary planted population (seeds/acre), nutrient application (gallons/acre), and/or pesticide application (lb./acre) based off of zones created by organic matter, soil moisture, and/or electrical conductivity.

In another embodiment, any of the sensors or camera can be adapted to harvest energy to power the sensor and/or wireless communication. As the sensors are dragged through the soil, the heat generated by soil contact or the motion of the sensors can be used as an energy source for the sensors.

Figure 55:
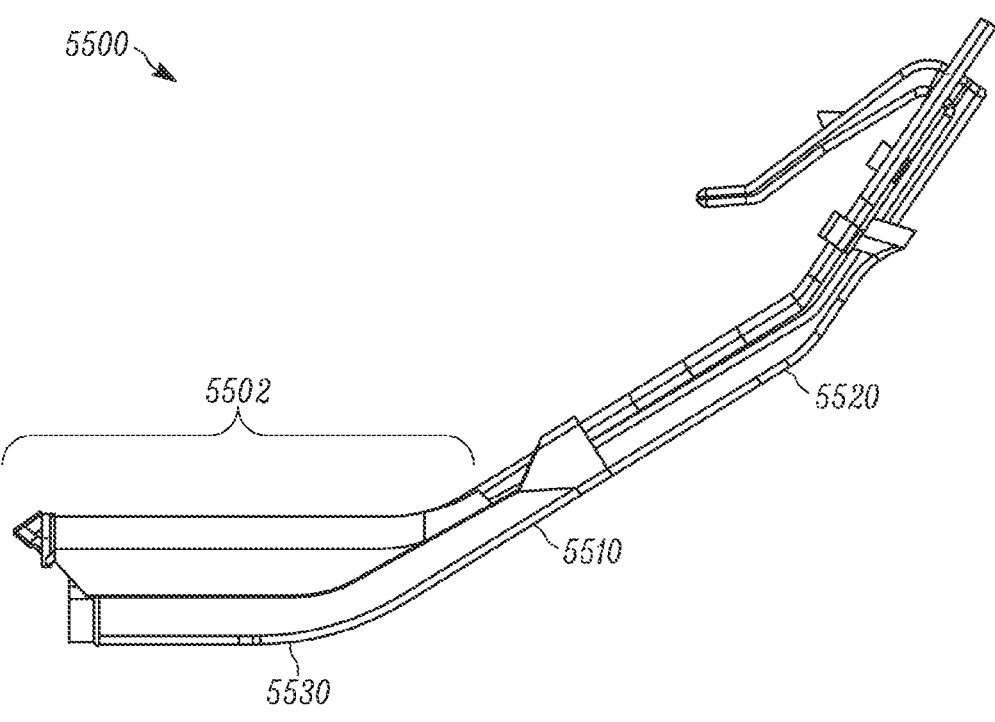
FIGS. 55-56 illustrate a soil apparatus (e.g., firmer) having a locking system in accordance with one embodiment.

FIGS. 55-66 illustrate a soil apparatus (e.g., firmer) having a locking system in accordance with one embodiment. The firmer 5500 includes a base 5502 and a mounting portion 5520 (e.g., neck portion 5520) as illustrated in FIG. 55. The mounting portion 5520 is preferably stiffened by inclusion of a stiffening insert made of stiffer material than the mounting portion (e.g., the mounting portion may be made of plastic and the stiffening insert may be made of metal) in an inner cavity of the mounting portion 5520. An upper portion 5510 of the base as illustrated in FIGS. 55, 56, 60, and 61 may include an internal cavity that is sized or designed to receive a liquid application conduit. The internal cavity may include a rearward aperture through which the liquid application conduit extends for dispensing liquid behind the firmer 5500. It should be appreciated that a plurality of liquid conduits may be inserted in the internal cavity; additionally, a nozzle may be included at a terminal end of the conduit or conduits to redirect and/or split the flow of liquid applied in the trench behind the firmer 5500.

The base 5502 includes a ground-engaging lower portion 5530 of the base as illustrated in FIGS. 55, 56, 59, 62, and 66 that can be removably inserted and connected to the upper portion 5510; but in other embodiments the ground-engaging lower portion may be installed and removed without the use of tools, e.g. by a slot-and-groove arrangement. The ground-engaging lower portion 5530 is preferably made of a material having greater wear-resistance than plastic such as metal (e.g., stainless steel or hardened white iron), may include a wear-resistant coating (or a non-stick coating as described herein), and may include a wear-resistant portion such as a tungsten carbide insert.

The ground-engaging lower portion 5530 of the base preferably includes at least one sensor for detecting characteristics of soil or a trench (e.g., soil moisture, soil organic matter, soil temperature, seed presence, seed spacing, percentage of seeds firmed, soil residue presence) such as a reflectivity sensor, preferably housed in a cavity of the ground-engaging lower portion. The reflectivity sensor preferably includes a sensor circuit board having a sensor disposed to receive reflected light from the trench through a transparent window 5592. The transparent window 5592 is preferably mounted flush with a lower surface of the ground-engaging lower portion such that soil flows underneath the window without building up over the window or along an edge thereof. An electrical connection preferably connects the sensor circuit board to a wire or bus (not shown) placing the sensor circuit board in data communication with the monitor 50.

Figure 57:
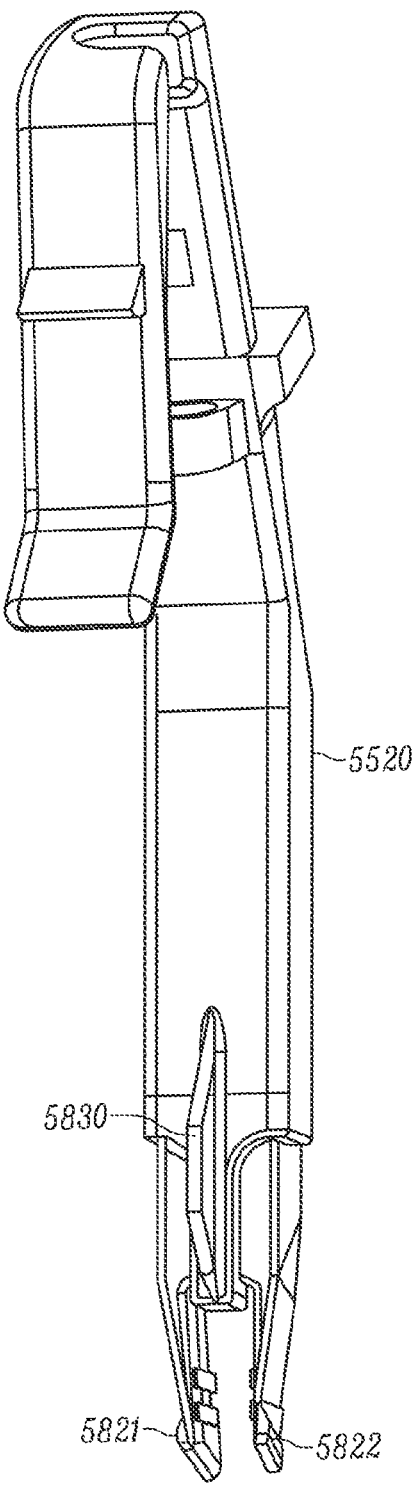
FIG. 57 illustrates a neck portion of a soil apparatus having protrusions (e.g., two prongs 5821-5822) to insert into a lower portion of a base in accordance with one embodiment.

The firmer 5500 includes a locking system for different components of the firmer. In one example, a neck portion 5520 has protrusions (e.g., two prongs 5821-5822) as illustrated in FIG. 57 that insert into a lower portion 5530 of the base. This does not lock until an upper portion 5510 of the base with a region (e.g., "post 6010") is inserted into the lower portion and the region (e.g., "post 6010") presses the protrusions (e.g., two prongs apart) to lock the neck portion to the base.

Alternatively, protrusions 5821 and 5822 could alternatively lock to the base (e.g., lower base portion, upper base portion) without the need of the post. The base could have holes (e.g., circular holes, stepped holes) to accept the tabs on protrusions 5821 and 5822.

In one example, a dividing ridge 5830 on the neck portion divides a fluid tube and the electrical line and holds them against U-shaped clips integrated into the side of the neck portion.

Figure 59:
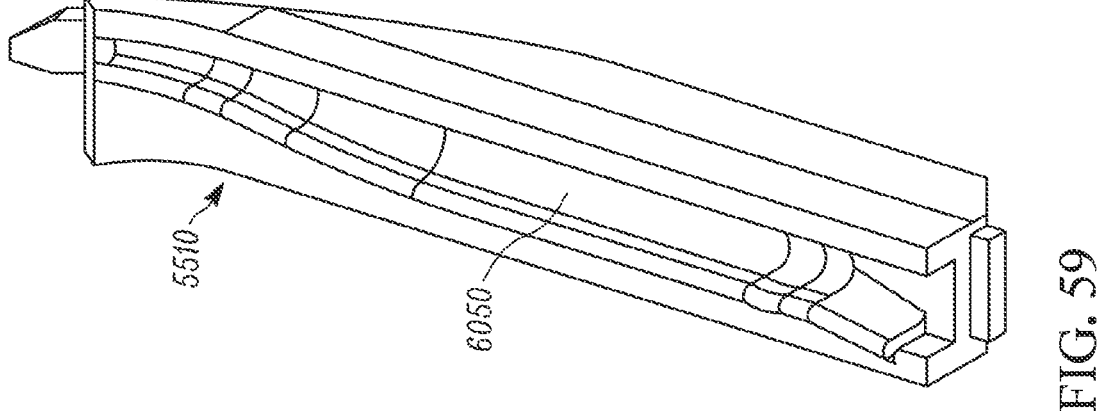
FIGS. 59-60 illustrate an upper portion of a base of a soil apparatus in accordance with one embodiment.
Figure 58:
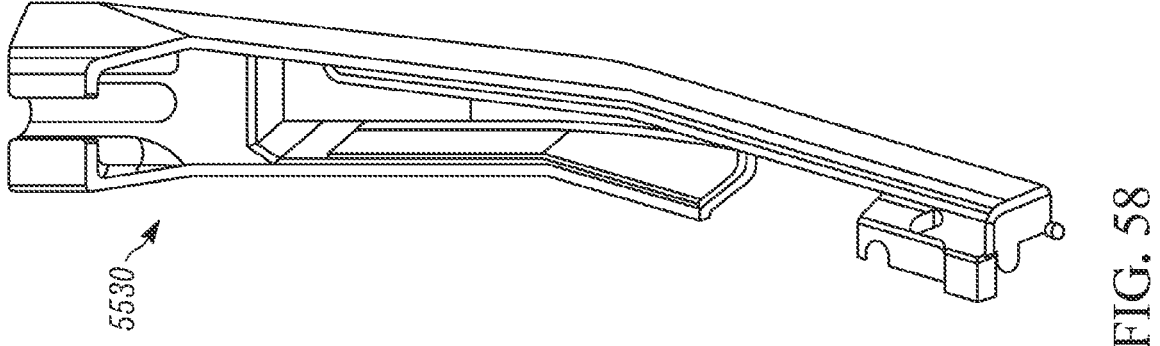
FIG. 58 illustrates a ground-engaging lower portion of a base of a soil apparatus in accordance with one embodiment.
Figure 60:
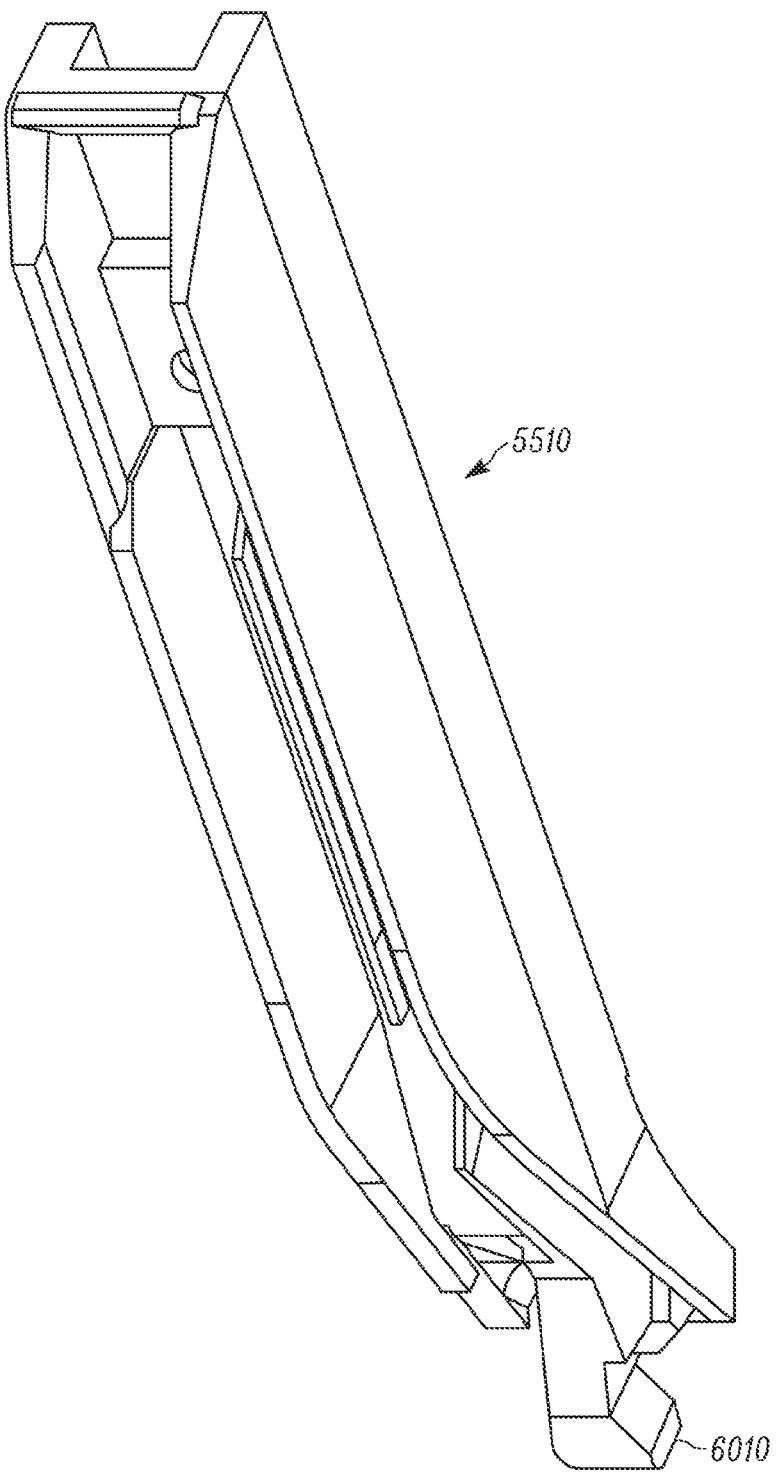
Figure 61:
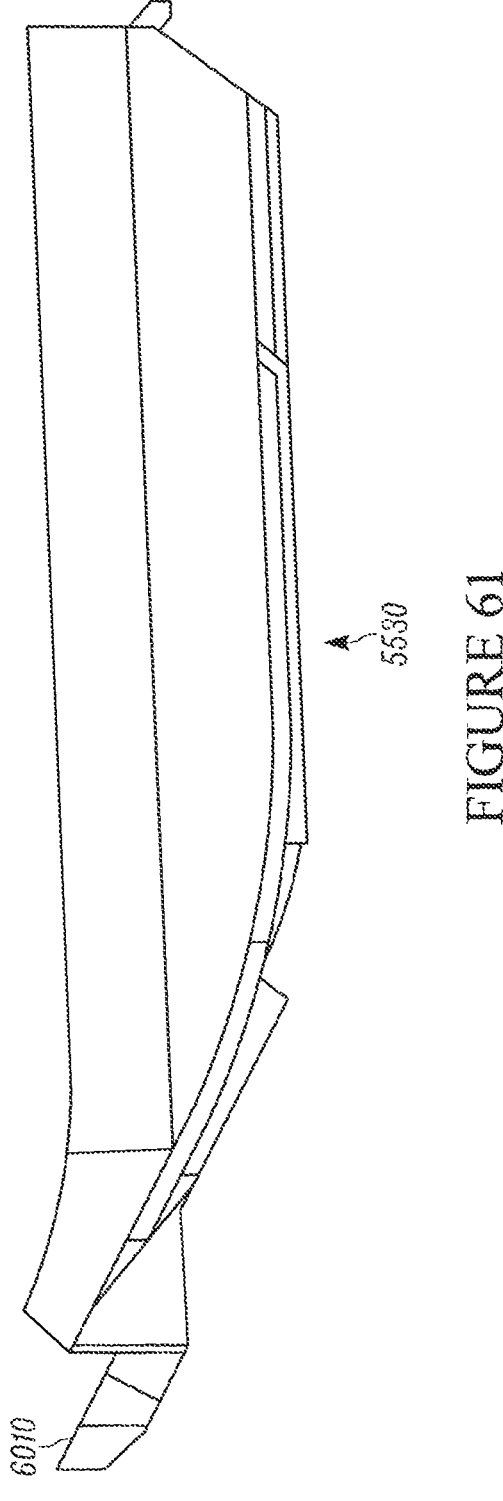
FIG. 61 illustrates a ground-engaging lower portion of a base of a soil apparatus in accordance with one embodiment.
Figure 62:
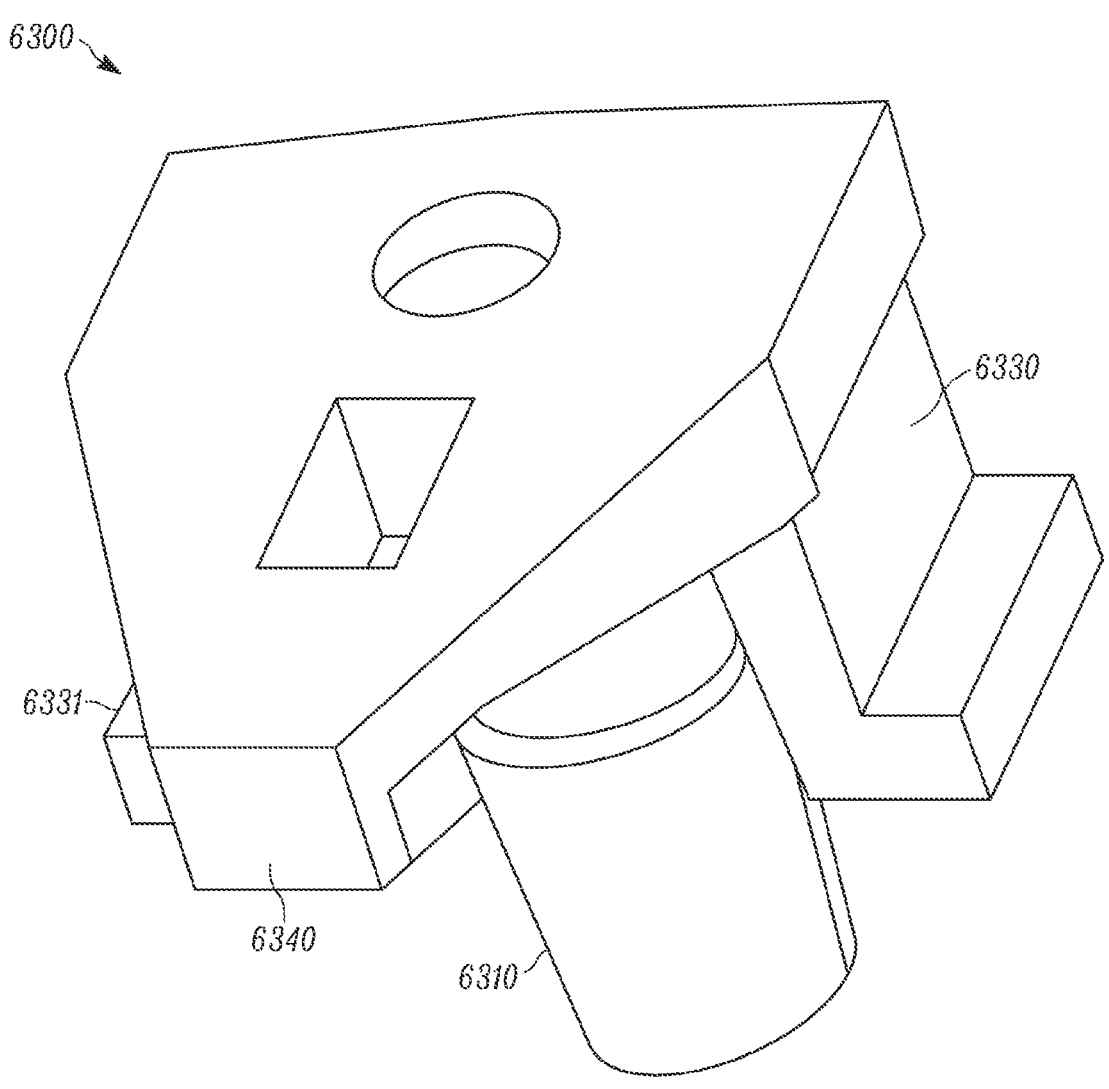
FIGS. 62 and 63 illustrate a connector 6300 having a nipple 6310 to insert into the fluid tube in accordance with one embodiment.
Figure 63:
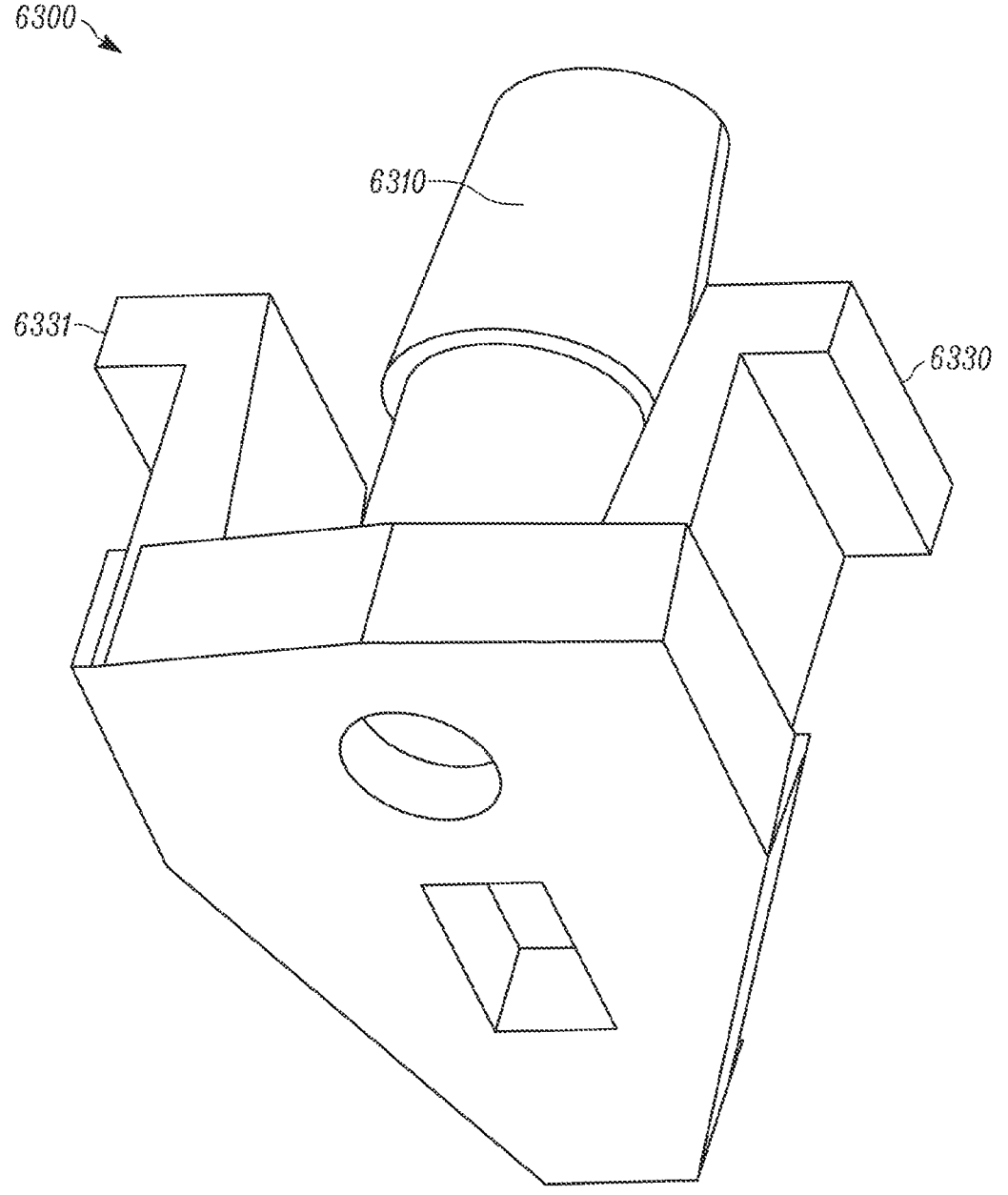

A fluid tube lies in a channel 6050 in the upper portion 5510 of the base 5502 as illustrated in FIG. 59. FIGS. 62 and 63 illustrate a connector 6300 having a nipple 6310 to insert into the fluid tube in accordance with one embodiment. The connector has wings 6330-6331 that engage the upper portion of the base. There is a clip 6340 at the bottom of the front face to clip the connector to the upper portion.

Figure 56:
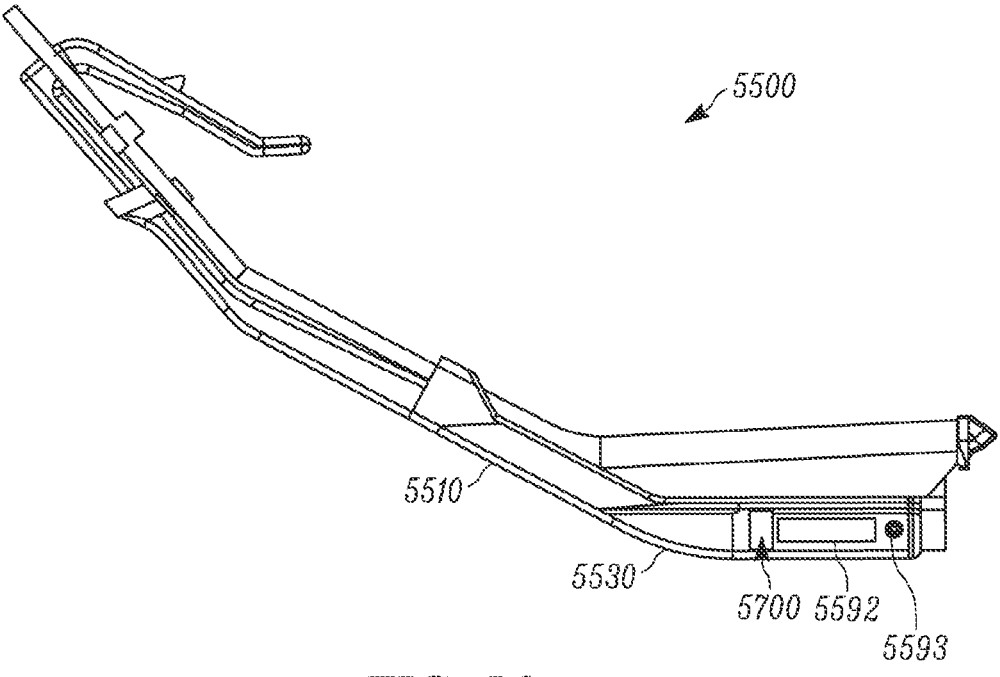

A wear resistant insert 5700 is positioned ahead of the window 5592 to provide wear resistance for the window as illustrated in FIG. 56. In one example, the material of the insert is preferably tungsten carbide though other wear resistance materials can be used. In another example, the insert 5700 can also be above and/or below the window 5592 in addition to or in place of before the window. Also, a temperature sensor 5593 is positioned adjacent to window 5592. Temperature sensor 5593 can be a temperature sensor described in U.S. Application No. 62/516,553, filed on 7 Jun. 2017, which was later incorporated into U.S. Patent Application Number 2018/0168094A1.

Figure 64:
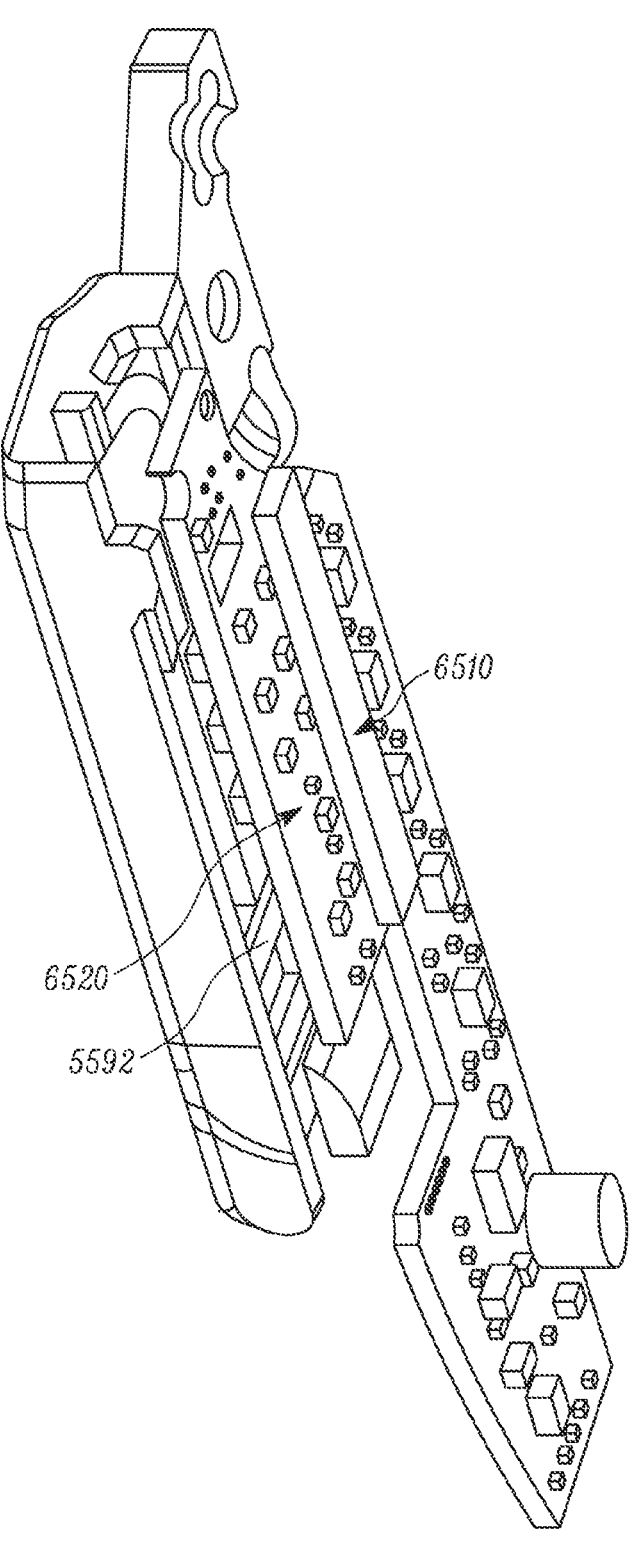
FIG. 64 illustrates a side view of a layer 6510 of resilient material (e.g., foam) to push a circuit board 6520 (e.g., printed circuit board, sensor circuit board) into a transparent window 5592 of a base 5502 or in close proximity to the window in accordance with one embodiment.

FIG. 64 illustrates a side view of a layer 6510 of resilient material (e.g., foam) to push a circuit board 6520 (e.g., printed circuit board, sensor circuit board) into a transparent window 5592 of a base 5502 or in close proximity to the window. The resilient layer 6510 functions as a "Locking spring" for positioning the circuit board 6520 with respect to the window 5592.

Figure 65:
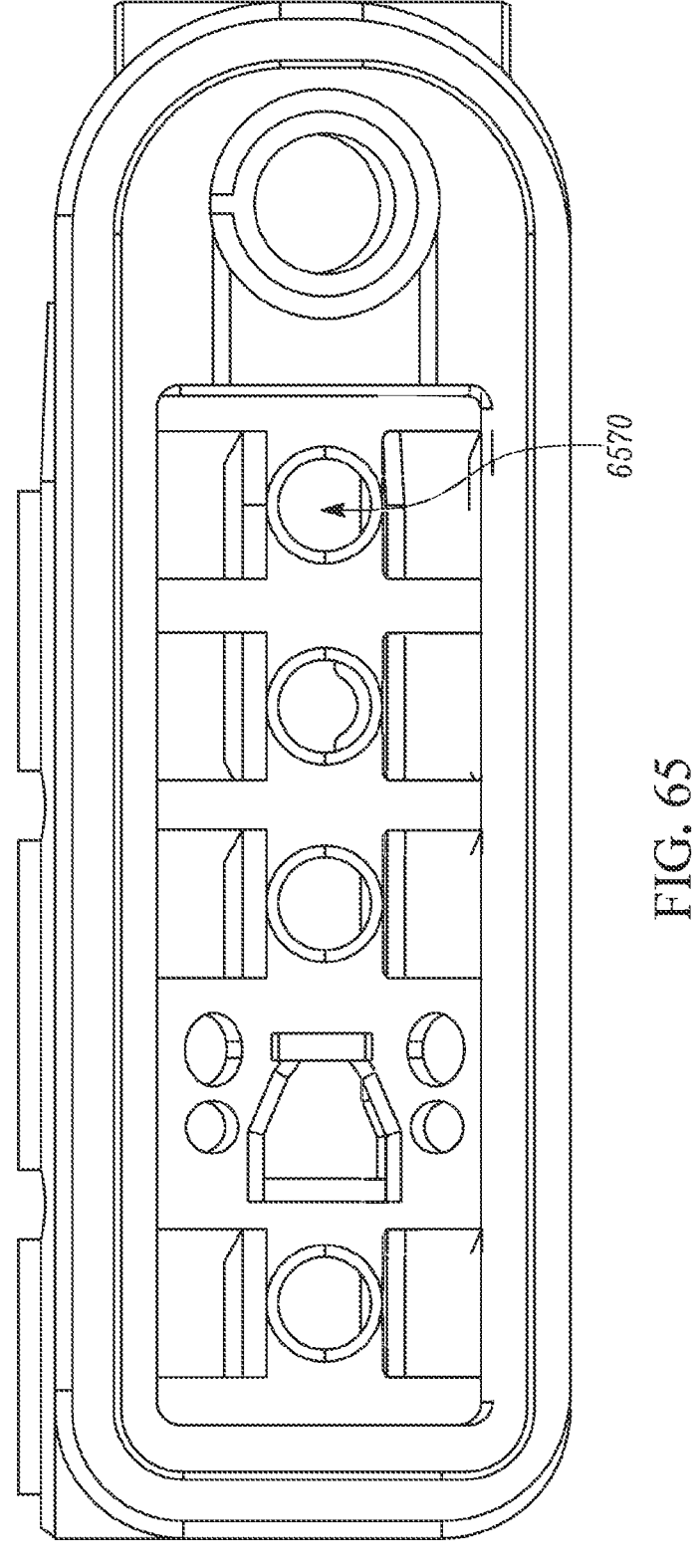
FIG. 65 illustrates a top view of a circuit board in accordance with one embodiment.

For securing a prism and emitters (e.g., sensors) to the board 6520, there are pins and holes 6570 with a snug fit as illustrated in FIG. 65. Screws may allow too much give and allow the emitters to move.

Figure 66:
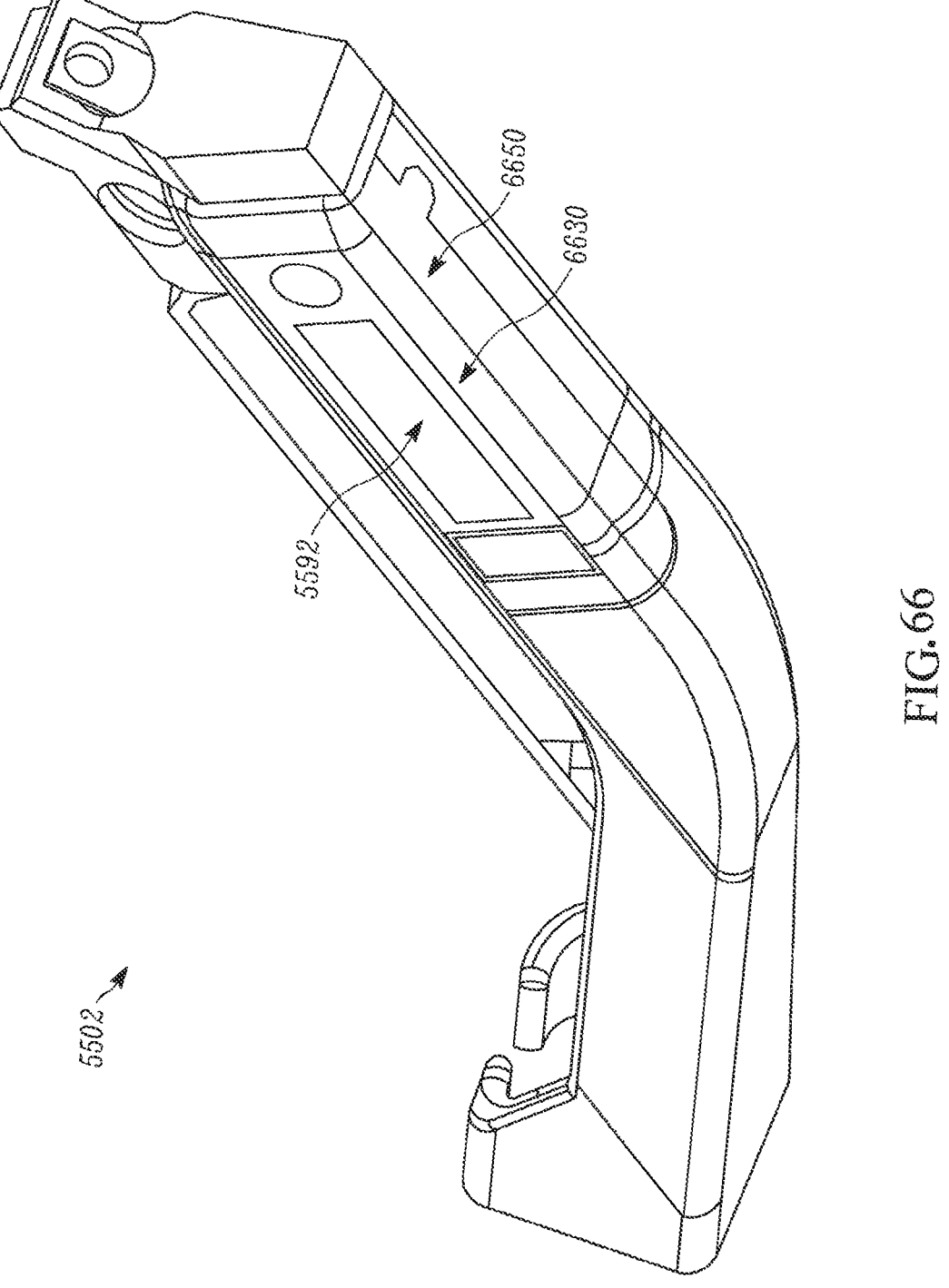
FIG. 66 illustrates a base having a separate window portion in accordance with one embodiment.

FIG. 66 illustrates a base having a separate window portion in accordance with one embodiment. A window portion 6630 is a separate part to allow the window 5592 to be separately serviceable.

A water drain slit 6650 can be a gap in the base 5502. This will be where the window portion of the base mates with the base. The upper portion of the base can be a low friction abrasion resistant material (e.g., ultra high molecular weight polyethylene).

Figure 70A:
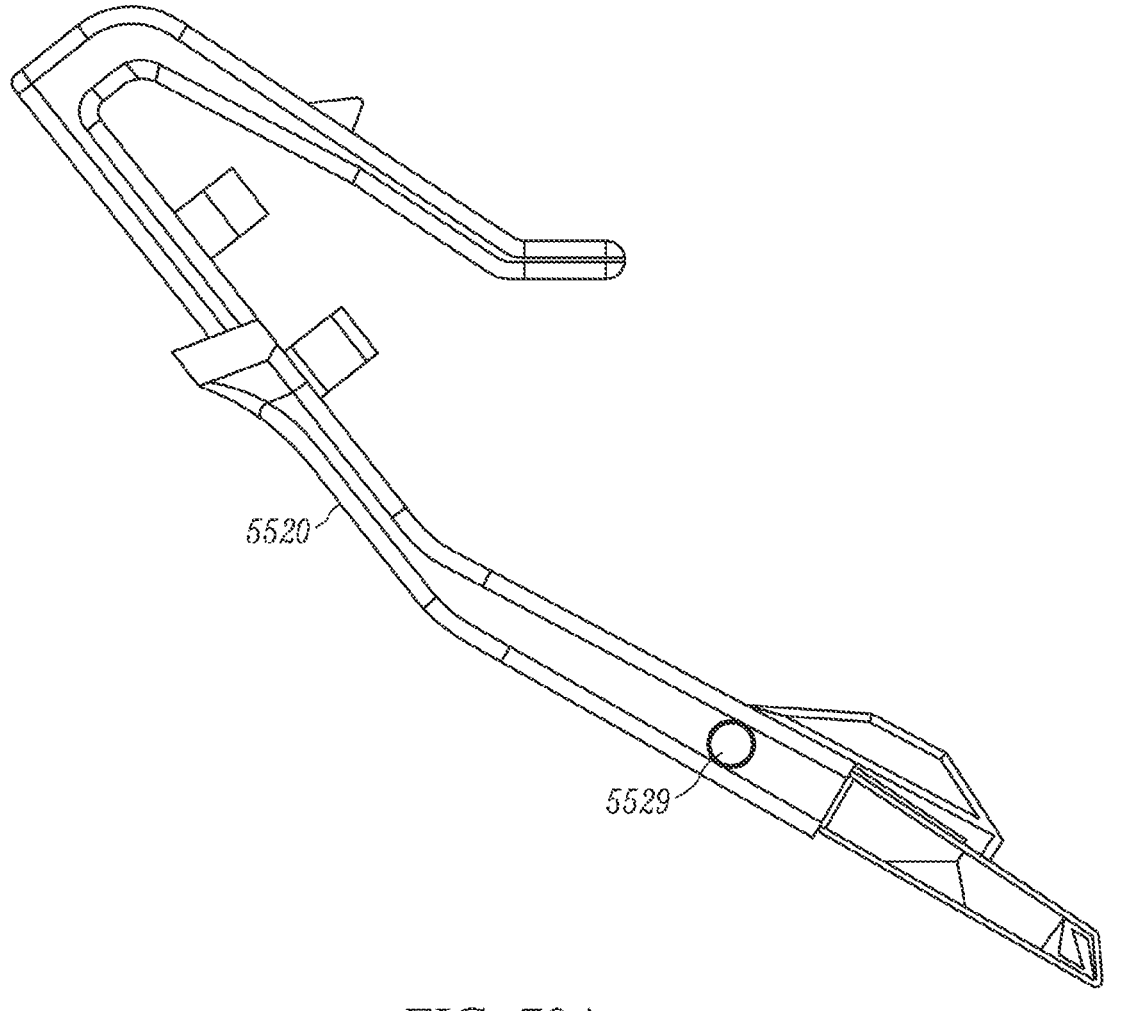
FIG. 70A illustrates a side view of a neck portion having a hole.
Figure 70B:
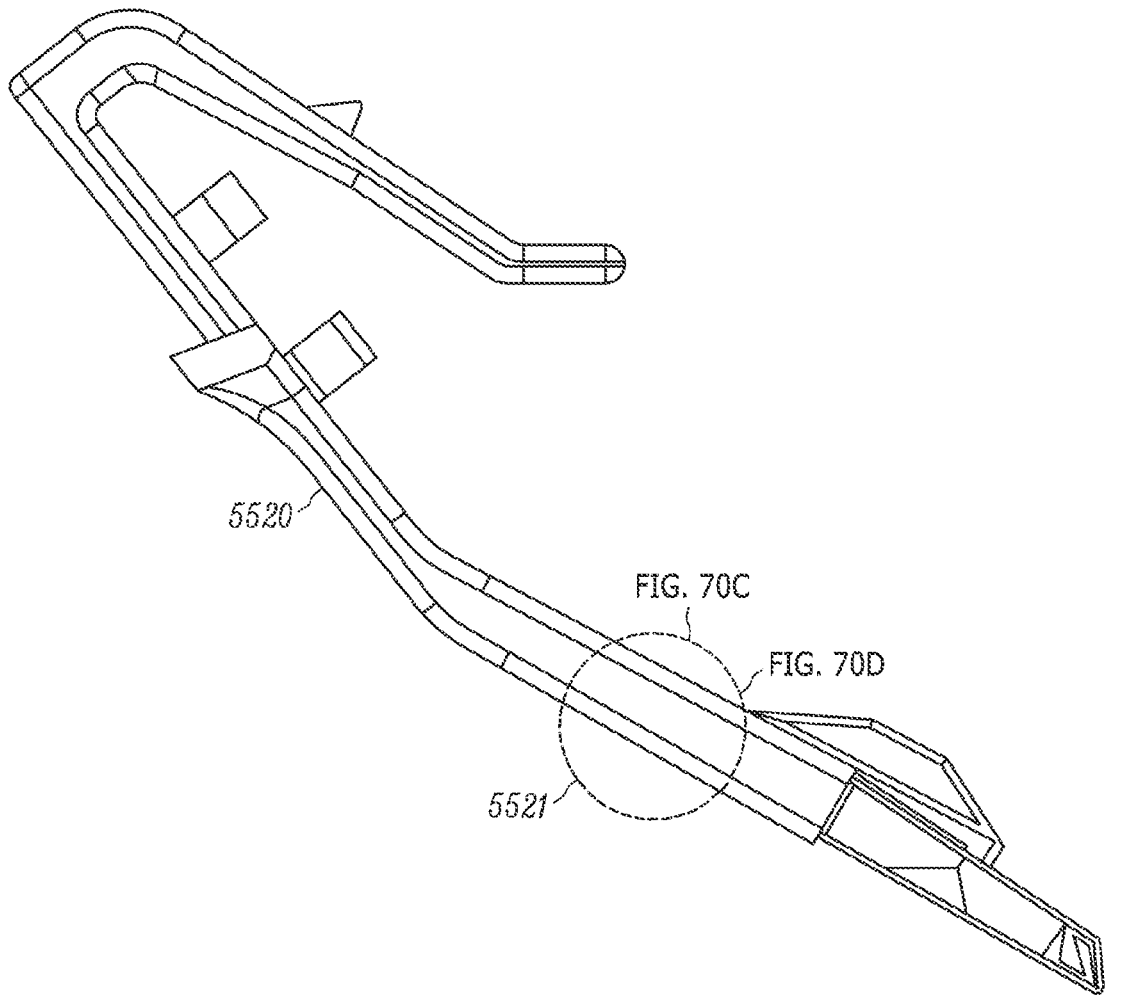
FIG. 70B illustrates a side view of a neck portion having a force relief.
Figure 70C:
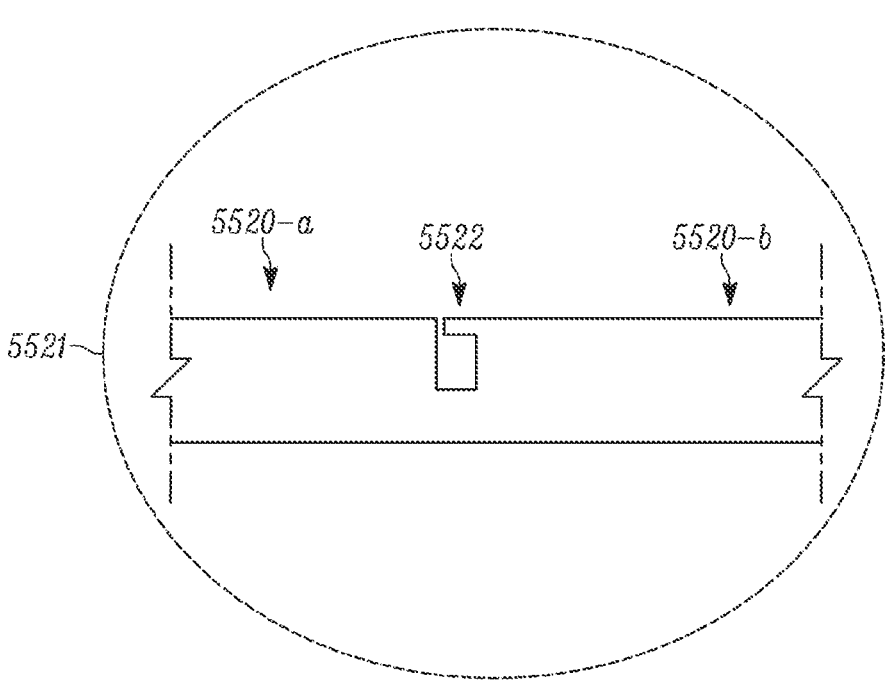
FIG. 70C illustrates a side view of a section of FIG. 70B with a first force relief.
Figure 70D:
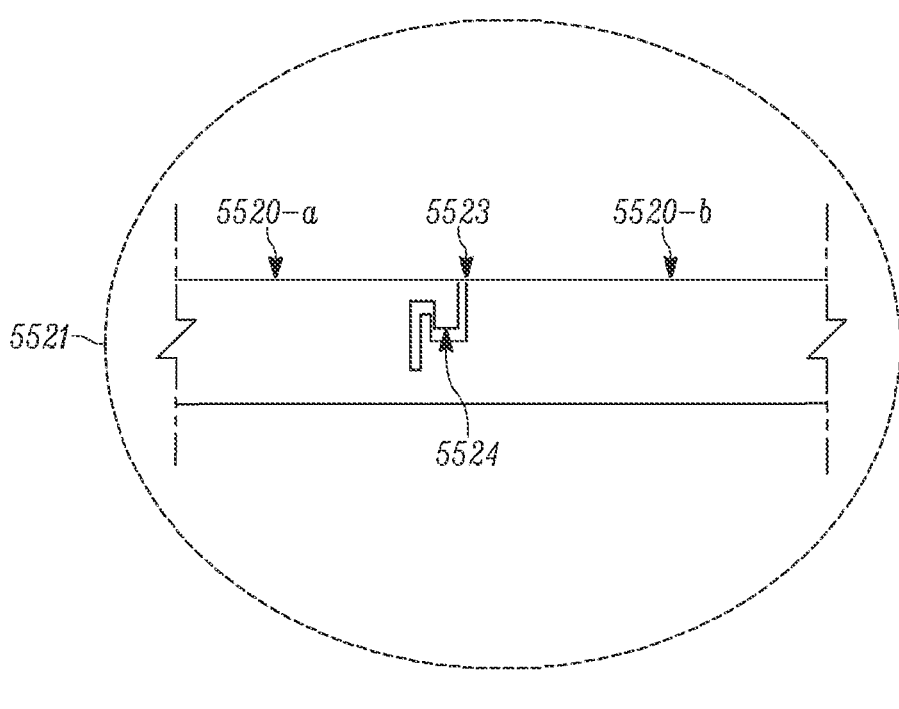
FIG. 70D illustrates a side view of a section of FIG. 70B with a second force relief.

There can be an incident when the agricultural implement is driven in reverse with the sensor implement (such as firmer 400, 400') still engaged with the ground. Doing so, can damage the sensor implement. Base 5502 can be the most expensive part of the sensor implement because it can be made from cobalt or other expensive materials. To prevent damage to base 5502, a force relief (5529, 5522, 5523) can be disposed in mounting portion 5520, or optionally in base 5502 when base 5502 is attached directly to the agricultural implement. Illustrated in FIG. 70A, a hole 5529 can be disposed in mounting portion 5520. When the agricultural implement is driven in reverse, the force to sensor implement (such as firmer 400, 400') is transferred to hole 5525 to cause mounting portion 5520 to break to relieve the applied force. Mounting portion 5520 is typically less expensive than base 5502. Instead of having mounting portion 5520 break, a spring (5522, 5523) can be formed in mounting portion 5520. FIG. 70B illustrates where a spring (5522, 5523) can be disposed in mounting portion 5520. FIG. 70C illustrates a first spring 5522 that is a partial opening in mounting portion 5520. FIG. 70D illustrates a second spring 5523 that is a partial opening in mounting portion 5520 with an interlock 5524. In either figure, as force is applied, portion 5520-b will bend away from portion

5520-a. During normal operation in which the agricultural implement is driven forward, forces keep portion 5520-a and portion 5520-b together. While illustrated as separate parts, mounting portion 5520 (e.g., neck portion 5520) can be unitary with base 5502. Also, as with other embodiments, base 5502 can be multiple parts.

In another embodiment illustrated in FIGS. 73 to 78, a firmer 5600 is modified to reduce adherence of sticky soils to firmer 5600.

Firmer 5600 can contain the same circuit board 6520, emitters 350, temperature sensor 5593, resilient layer 6510, window 5592, holes 6570, wear resistant insert 5700, etc. as firmer 5500, or firmer 5600 can be modified as described below. Firmer 5600 has a mounting portion 5620 (which can be the same as mounting portion 5520) and a base 5602.

Base 5602 has a lower outer portion 5603, which is illustrated in FIGS. 74A to 74D. Lower outer portion 5603 covers the lower portion of base 5602 except for window portion 5631. Lower outer portion 5603 is made from a low coefficient of friction material (less than or equal to 0.3 static or less than or equal to 0.25 dynamic as measured by ASTM D1894). In other embodiments, the coefficient of friction is less than or equal to 0.2 static or less than or equal to 0.15 dynamic. In one embodiment, lower outer portion 5603 is made from UHMW (ultra high molecular weight polyethylene). In other embodiments, lower outer portion 5603 covers at least 50% of the height of base 5602. In other embodiments, lower outer portion 5603 covers at least 80%, at least 85%, at least 90%, at least 95%, or at least 97% of the height of base 5602. Height can be measured perpendicular to any point along the bottom of lower outer portion 5603.

Figure 75:
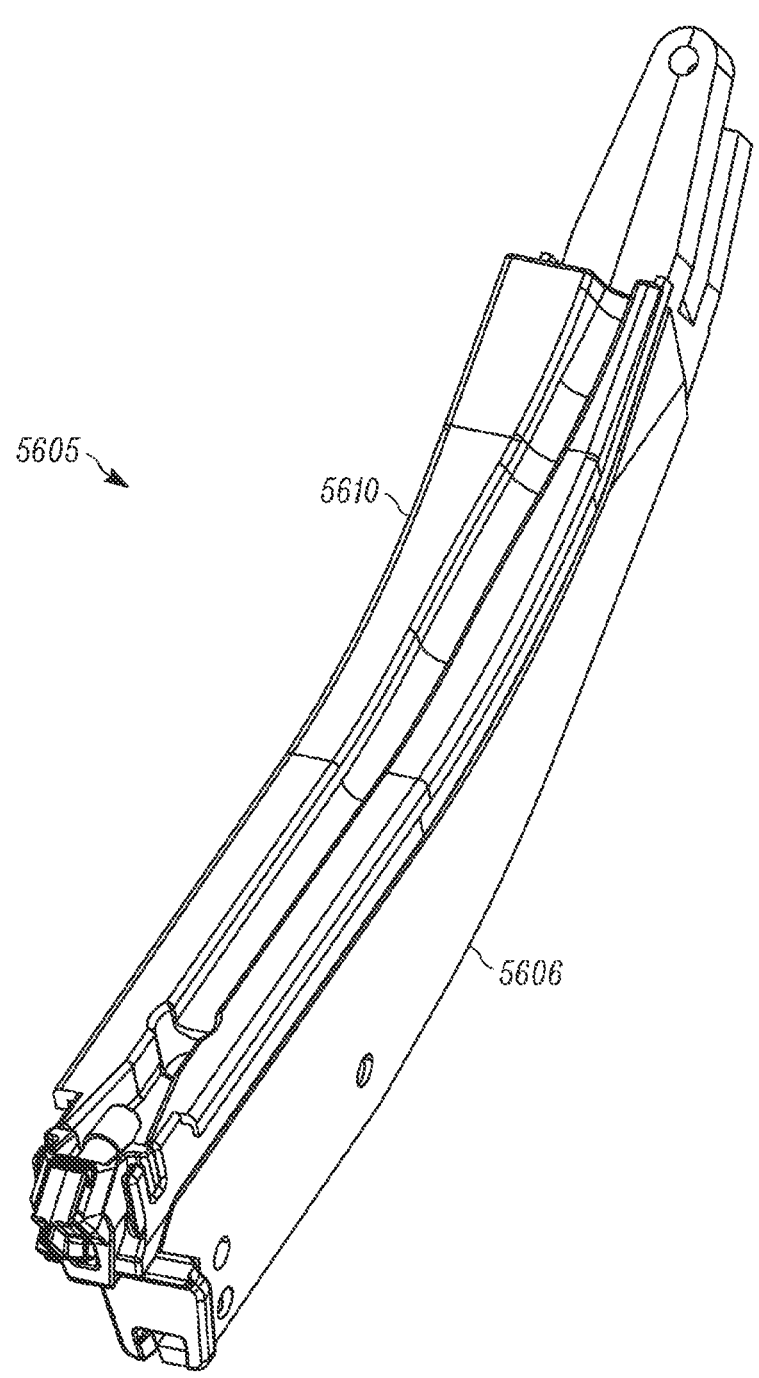
FIG. 75 is a perspective view of a lower portion of the soil apparatus of FIG. 73.
Figure 76A:
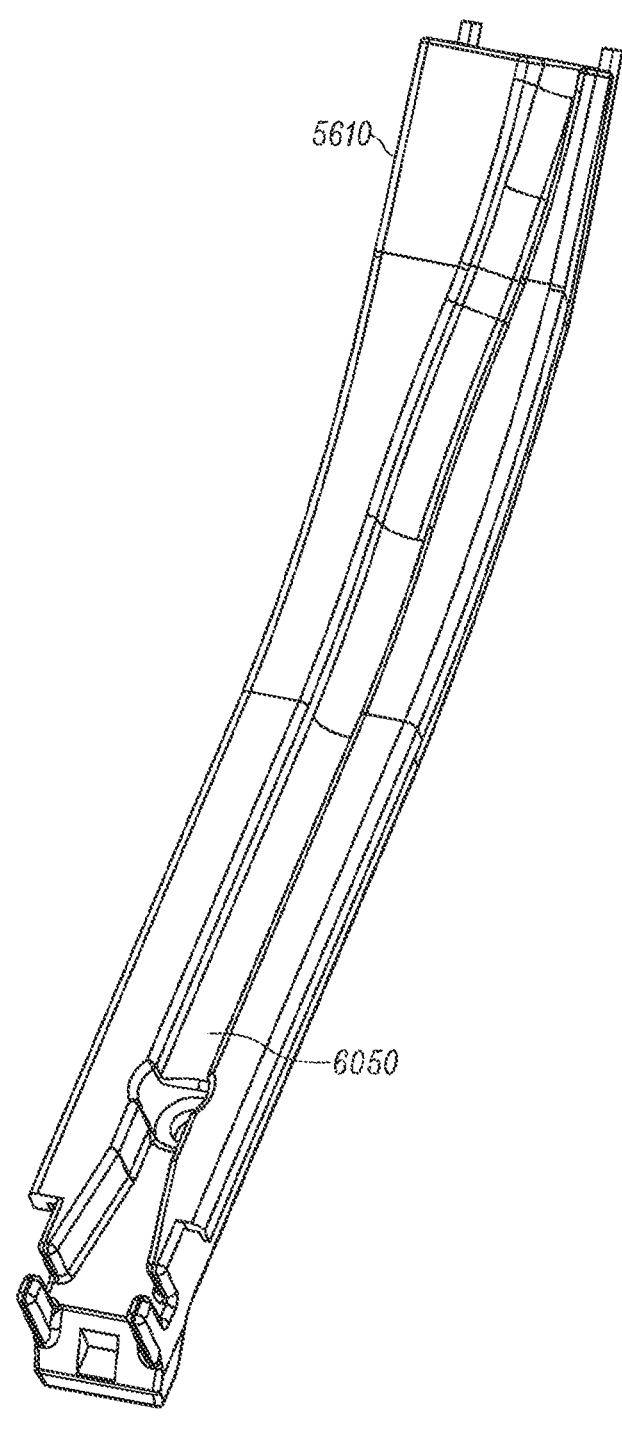
FIG. 76A is a top perspective view of an upper base portion of the soil apparatus of FIG. 73.
Figure 76B:
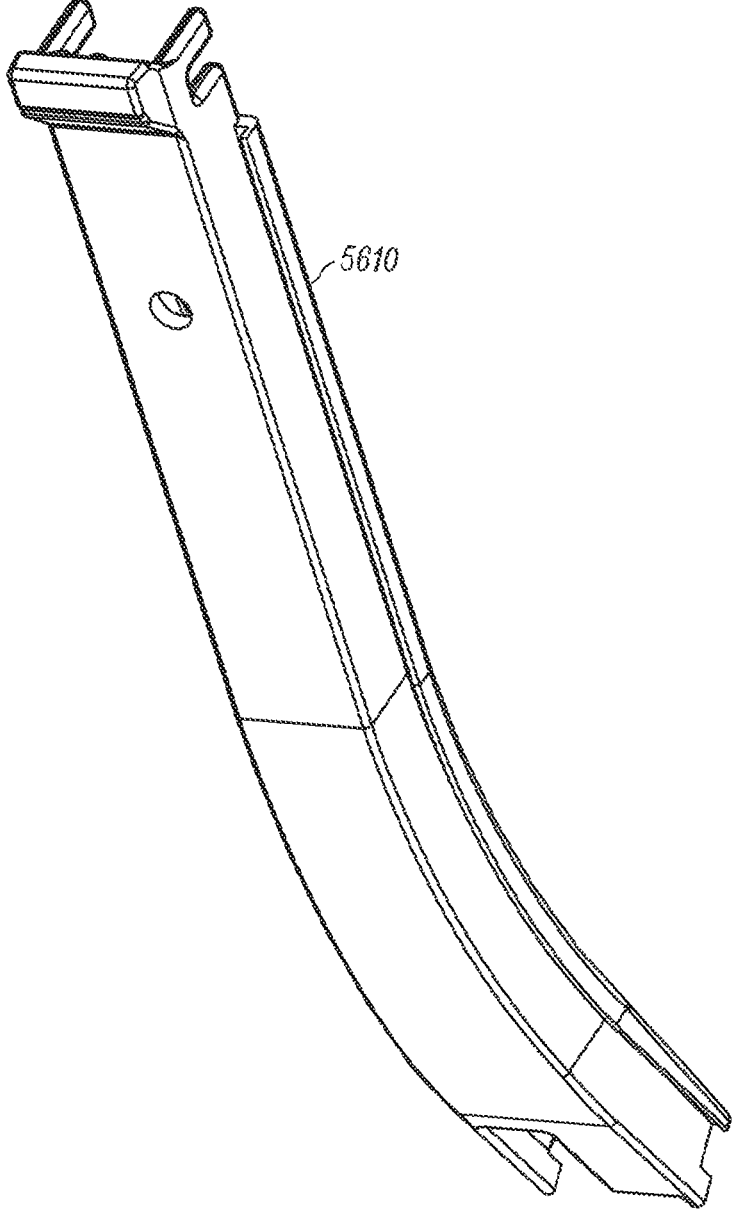
FIG. 76B is a bottom perspective view of an upper base portion of the soil apparatus of FIG. 73.

Base 5602 additionally includes a second portion 5605 having an upper base portion 5610 and lower internal portion 5606 as illustrated in FIG. 75. Upper base portion can contain a channel 6050 as illustrated in FIG. 76A that is similar to channel 6050 for upper base portion 5510.

Figure 77A:
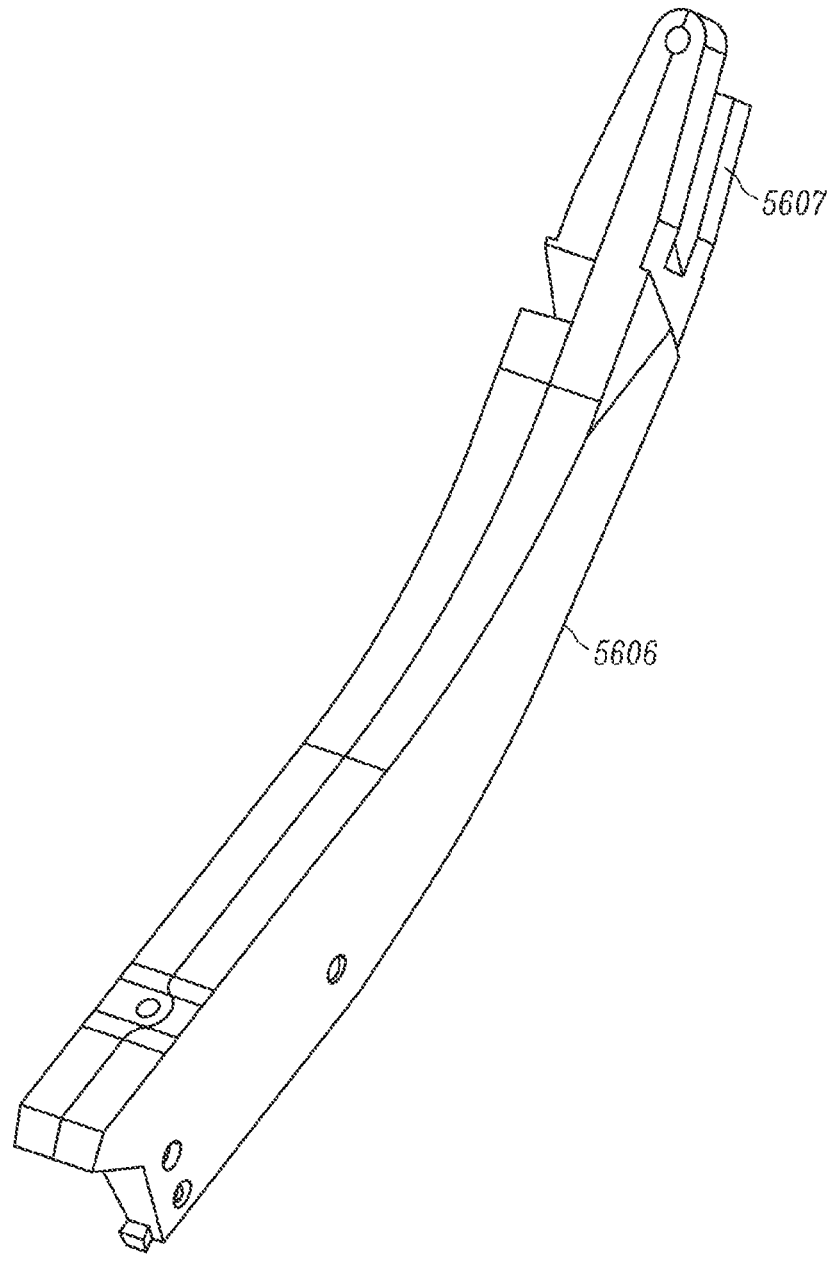
FIG. 77A is a perspective view of a lower base portion of the soil apparatus of FIG. 73.
Figure 77B:
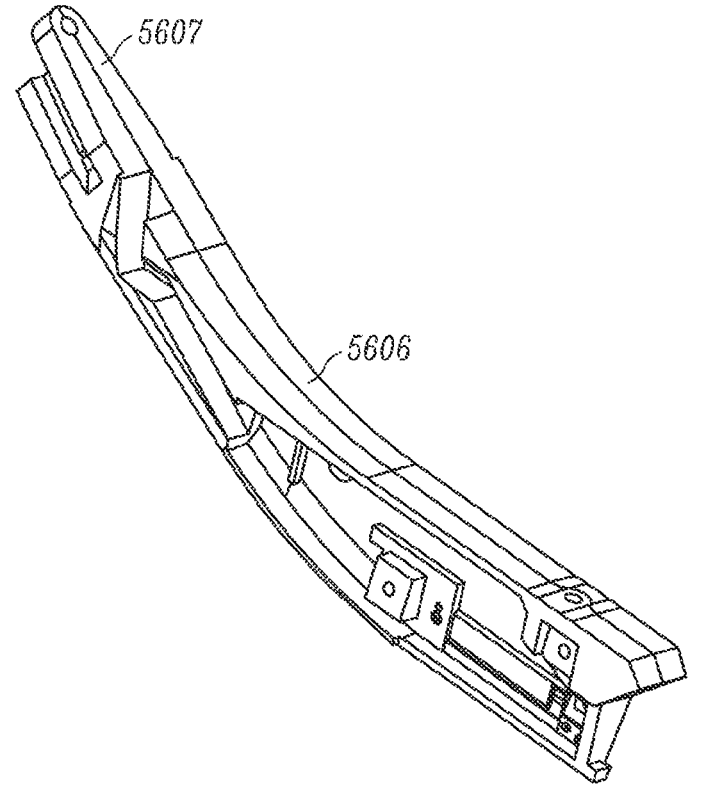
FIG. 77B is a perspective view of the lower base portion of the soil apparatus of FIG. 77A.
Figure 77C:
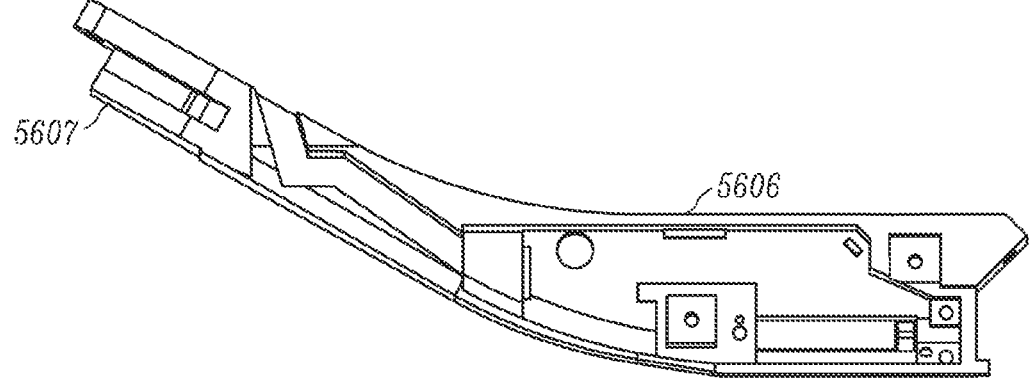
FIG. 77C is a left side elevation view of the lower base portion of the soil apparatus of FIG. 77A.
Figure 78:
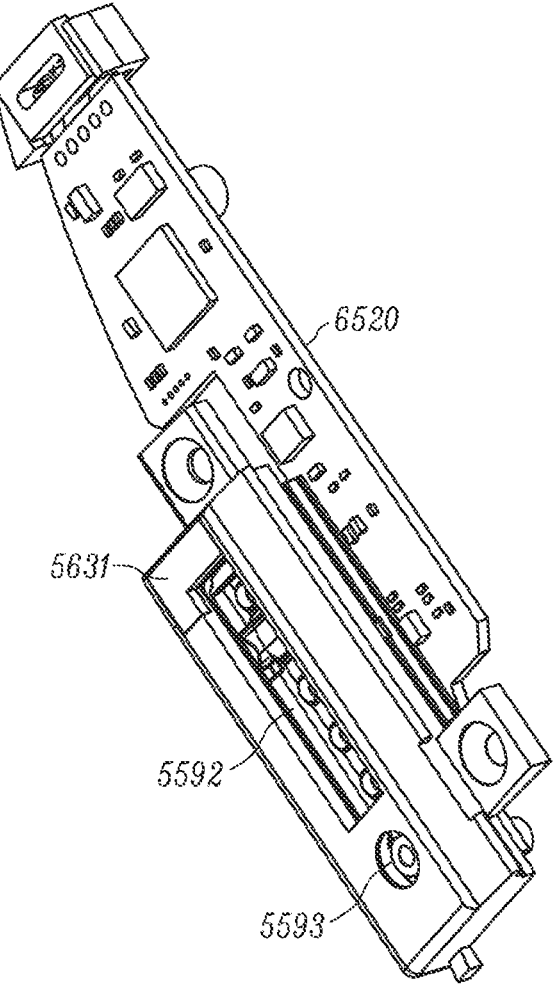
FIG. 78 is a perspective view of the circuit board of FIG. 73.

Lower outer portion 5603 covers lower internal portion 5606 that is disposed below upper base portion 5610. Lower internal portion 5606 has an end 5607 as illustrated in FIGS. 77A, 77B, and 77C for connection to mounting portion 5620. Mounting portion 5620 can be the same as mounting portion 5520. Lower internal portion 5606 can provide structure to firmer 5600, and it can house circuit board 6520 as illustrated in FIG. 78. Lower outer portion 5603 can abut upper base portion at a seam 5604. As the height of lower outer portion 5603 changes, the location of seam 5604 changes.

Figure 73:
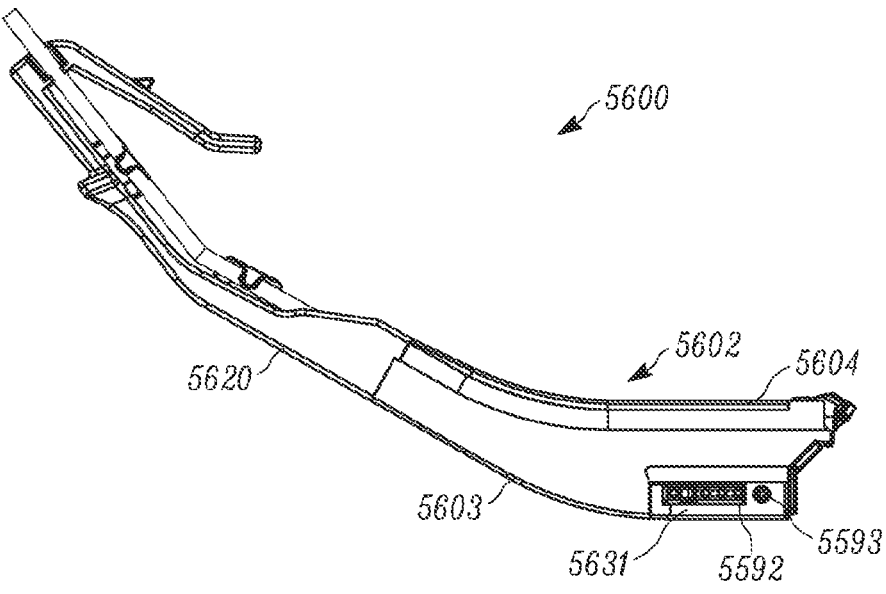
FIG. 73 illustrates a soil apparatus (e.g., firmer) having a low stick portion.
Figure 74A:
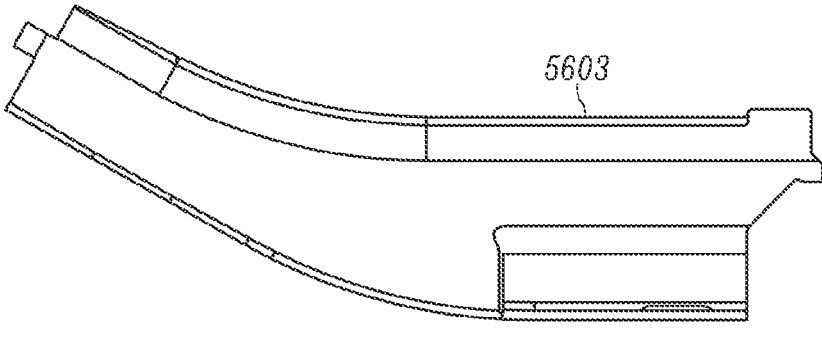
FIG. 74A illustrates a side elevation view of the low stick portion of the soil apparatus of FIG. 73.
Figures 74B, 74C:
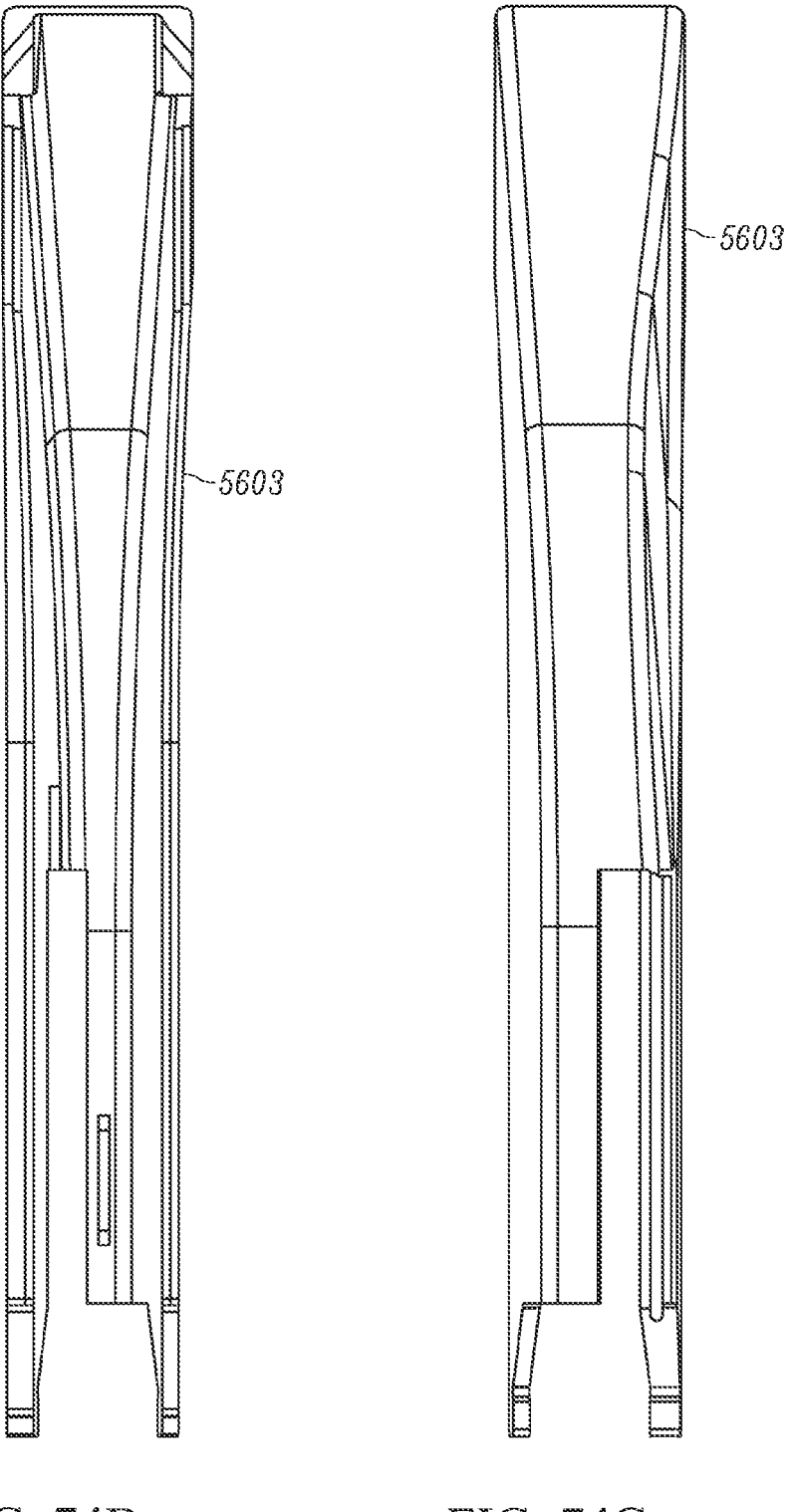
FIG. 74B is a top perspective view of the low stick portion of FIG. 74A.
FIG. 74C is a bottom perspective view of the low stick portion of FIG. 74A.
Figure 74D:
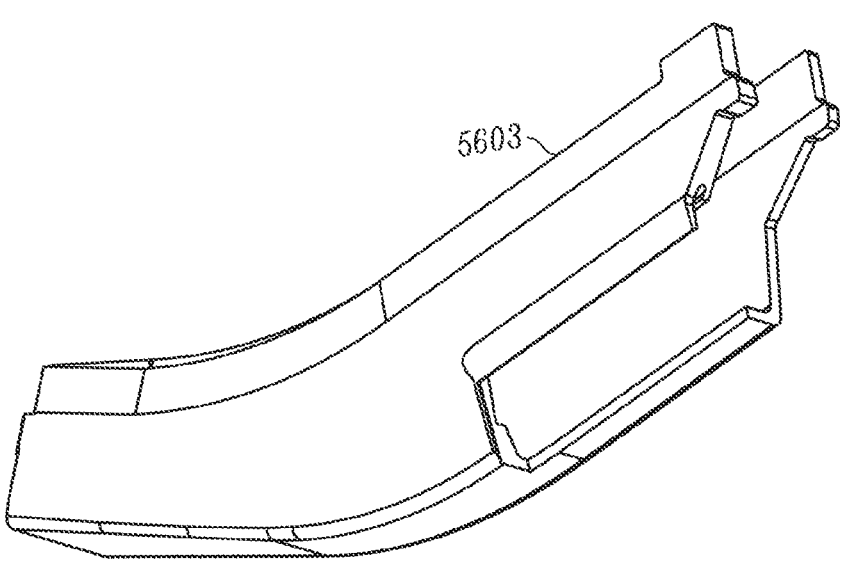
FIG. 74D is a perspective view of the low stick portion of FIG. 74A.

Lower engaging portion 5631 is similar to lower engaging portion 5530 but is reduced in size as lower outer portion 5603 covers more of base 5602. Lower engaging portion 5631 has window 5592 and temperature sensor 5593 as illustrated in FIG. 73. Lower engaging portion 5631 can be made from the same material as lower engaging portion 5530 to provide wear resistance and protect circuit board 6520 and emitters 350.

Any data that is measured during a pass through the field can be stored in a geo-referenced map and used again during a later pass in the same field during the same season or in a subsequent year. For example, organic matter can be measured during a planting pass through the field during planting. Having the geo-referenced organic matter content can be used during a fertilization pass to variable rate fertilizer based on location specific organic matter content. The data collected can be stored in a separate data file or as part of the field file.

Figure 79:
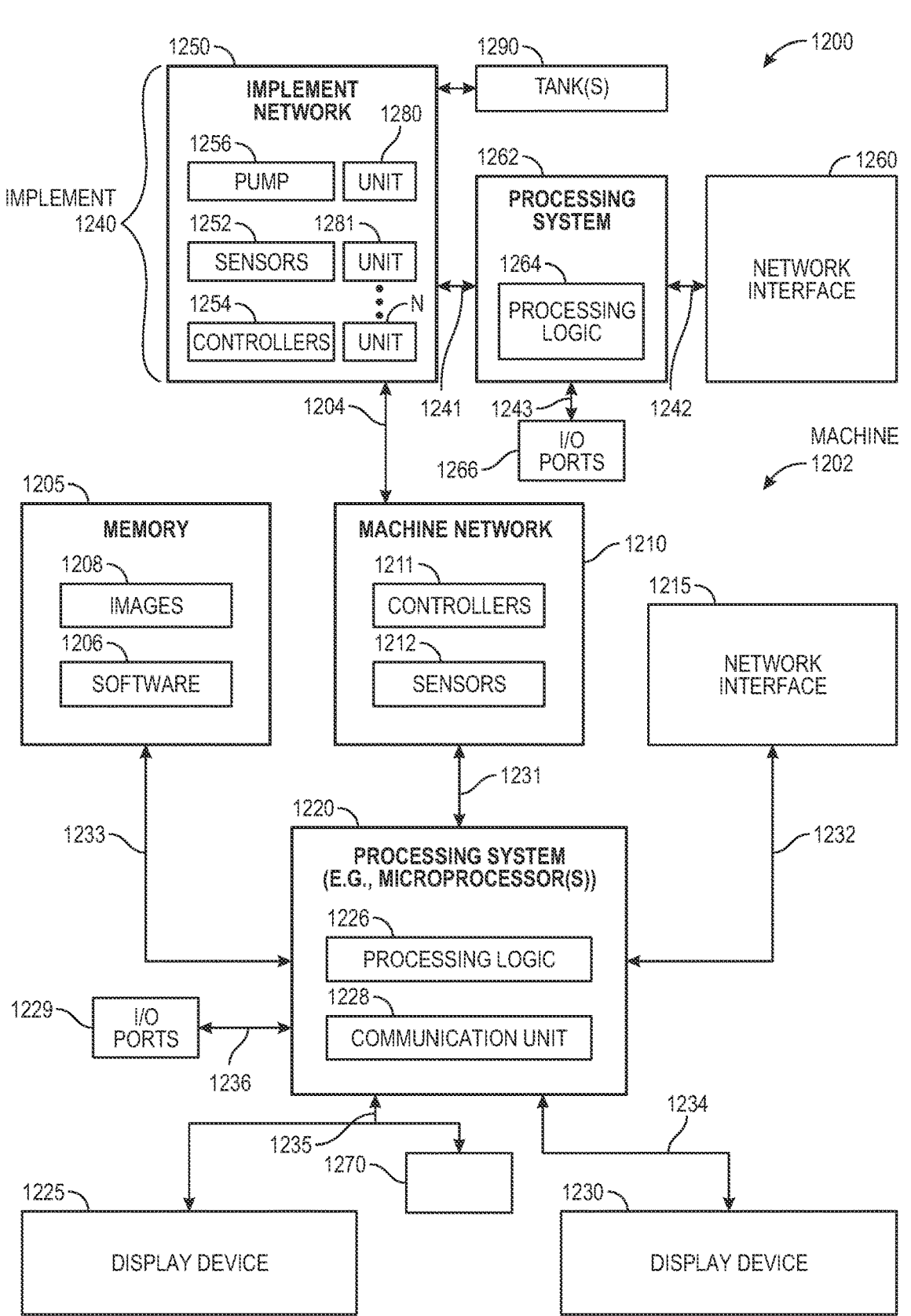
FIG. 79 shows an example of a system 1200 that includes a machine 1202 (e.g., tractor, combine harvester, etc.) and an implement 1240 (e.g., planter, sidedress bar, cultivator, plough, sprayer, spreader, irrigation implement, etc.) in accordance with one embodiment.

FIG. 79 shows an example of a system 1200 that includes a machine 1202 (e.g., tractor, combine harvester, etc.) and an implement 1240 (e.g., planter, sidedress bar, cultivator, plough, sprayer, spreader, irrigation implement, etc.) in accordance with one embodiment. The machine 1202 includes a processing system 1220, memory 1205, machine network 1210 (e.g., a controller area network (CAN) serial bus protocol network, an ISOBUS network, etc.), and a network interface 1215 for communicating with other systems or devices including the implement 1240. The machine network 1210 includes sensors 1212 (e.g., speed sensors), controllers 1211 (e.g., GPS receiver, radar unit) for controlling and monitoring operations of the machine or implement. The network interface 1215 can include at least one of a GPS transceiver, a WLAN transceiver (e.g., WiFi), an infrared transceiver, a Bluetooth transceiver, Ethernet, or other interfaces from communications with other devices and systems including the implement 1240. The network interface 1215 may be integrated with the machine network 1210 or separate from the machine network 1210 as illustrated in FIG. 12. The I/O ports 1229 (e.g., diagnostic/on board diagnostic (OBD) port) enable communication with another data processing system or device (e.g., display devices, sensors, etc.).

In one example, the machine performs operations of a tractor that is coupled to an implement for planting applications of a field. The planting data for each row unit of the implement can be associated with locational data at time of application to have a better understanding of the planting for each row and region of a field. Data associated with the planting applications can be displayed on at least one of the display devices 1225 and 1230. The display devices can be integrated with other components (e.g., processing system 1220, memory 1205, etc.) to form the monitor 50.

The processing system 1220 may include one or more microprocessors, processors, a system on a chip (integrated circuit), or one or more microcontrollers. The processing system includes processing logic 1226 for executing software instructions of one or more programs and a communication unit 1228 (e.g., transmitter, transceiver) for transmitting and receiving communications from the machine via machine network 1210 or network interface 1215 or implement via implement network 1250 or network interface 1260. The communication unit 1228 may be integrated with the processing system or separate from the processing system. In one embodiment, the communication unit 1228 is in data communication with the machine network 1210 and implement network 1250 via a diagnostic/OBD port of the I/O ports 1229.

Processing logic 1226 including one or more processors or processing units may process the communications received from the communication unit 1228 including agricultural data (e.g., GPS data, planting application data, soil characteristics, any data sensed from sensors of the implement 1240 and machine 1202, etc.). The system 1200 includes memory 1205 for storing data and programs for execution (software 1206) by the processing system. The memory 1205 can store, for example, software components such as planting application software for analysis of soil and planting applications for performing operations of the present disclosure, or any other software application or module, images 1208 (e.g., captured images of crops, soil, furrow, soil clods, row units, etc.), alerts, maps, etc. The memory 1205 can be any known form of a machine readable non-transitory storage medium, such as semiconductor memory (e.g., flash; SRAM; DRAM; etc.) or non-volatile memory, such as hard disks or solid-state drive. The system can also include an audio input/output subsystem (not shown) which may include a microphone and a speaker for, for example, receiving and sending voice commands or for user authentication or authorization (e.g., biometrics).

The processing system 1220 communicates bi-directionally with memory 1205, machine network 1210, network interface 1215, display device 1230, display device 1225, and I/O ports 1229 via communication links 1231-1236, respectively. The processing system 1220 can be integrated with the memory 1205 or separate from the memory 1205.

Display devices 1225 and 1230 can provide visual user interfaces for a user or operator. The display devices may include display controllers. In one embodiment, the display device 1225 is a portable tablet device or computing device with a touchscreen that displays data (e.g., planting application data, captured images, localized view map layer, high definition field maps of seed germination data, seed environment data, as-planted or as-harvested data or other agricultural variables or parameters, yield maps, alerts, etc.) and data generated by an agricultural data analysis software application and receives input from the user or operator for an exploded view of a region of a field, monitoring and controlling field operations. The operations may include configuration of the machine or implement, reporting of data, control of the machine or implement including sensors and controllers, and storage of the data generated. The display device 1230 may be a display (e.g., display provided by an original equipment manufacturer (OEM)) that displays images and data for a localized view map layer, as-applied fluid application data, as-planted or as-harvested data, yield data, seed germination data, seed environment data, controlling a machine (e.g., planter, tractor, combine, sprayer, etc.), steering the machine, and monitoring the machine or an implement (e.g., planter, combine, sprayer, etc.) that is connected to the machine with sensors and controllers located on the machine or implement.

A cab control module 1270 may include an additional control module for enabling or disabling certain components or devices of the machine or implement. For example, if the user or operator is not able to control the machine or implement using one or more of the display devices, then the cab control module may include switches to shut down or turn off components or devices of the machine or implement.

The implement 1240 (e.g., planter, cultivator, plough, sprayer, spreader, irrigation implement, etc.) includes an implement network 1250, a processing system 1262, a network interface 1260, and optional input/output ports 1266 for communicating with other systems or devices including the machine 1202. The implement network 1250 (e.g, a controller area network (CAN) serial bus protocol network, an ISOBUS network, etc.) includes a pump 1256 for pumping fluid from a storage tank(s) 1290 to application units 1280, 1281, . . . N of the implement, sensors 1252 (e.g., speed sensors, seed sensors for detecting passage of seed, sensors for detecting characteristics of soil or a trench including soil moisture, soil organic matter, soil temperature, seed presence, seed spacing, percentage of seeds firmed, and soil residue presence, downforce sensors, actuator valves, moisture sensors or flow sensors for a combine, speed sensors for the machine, seed force sensors for a planter, fluid application sensors for a sprayer, or vacuum, lift, lower sensors for an implement, flow sensors, etc.), controllers 1254 (e.g., GPS receiver), and the processing system 1262 for controlling and monitoring operations of the implement. The pump controls and monitors the application of the fluid to crops or soil as applied by the implement. The fluid application can be applied at any stage of crop development including within a planting trench upon planting of seeds, adjacent to a planting trench in a separate trench, or in a region that is nearby to the planting region (e.g., between rows of corn or soybeans) having seeds or crop growth.

For example, the controllers may include processors in communication with a plurality of seed sensors. The processors are configured to process data (e.g., fluid application data, seed sensor data, soil data, furrow or trench data) and transmit processed data to the processing system 1262 or 1220. The controllers and sensors may be used for monitoring motors and drives on a planter including a variable rate drive system for changing plant populations. The controllers and sensors may also provide swath control to shut off individual rows or sections of the planter. The sensors and controllers may sense changes in an electric motor that controls each row of a planter individually. These sensors and controllers may sense seed delivery speeds in a seed tube for each row of a planter.

The network interface 1260 can be a GPS transceiver, a WLAN transceiver (e.g., WiFi), an infrared transceiver, a Bluetooth transceiver, Ethernet, or other interfaces from communications with other devices and systems including the machine 1202. The network interface 1260 may be integrated with the implement network 1250 or separate from the implement network 1250 as illustrated in FIG. 12.

The processing system 1262 having processing logic 1264 communicates bi-directionally with the implement network 1250, network interface 1260, and I/O ports 1266 via communication links 1241-1243, respectively.

The implement communicates with the machine via wired and possibly also wireless bi-directional communications 1204. The implement network 1250 may communicate directly with the machine network 1210 or via the networks interfaces 1215 and 1260. The implement may also by physically coupled to the machine for agricultural operations (e.g., planting, harvesting, spraying, etc.).

The memory 1205 may be a machine-accessible non-transitory medium on which is stored one or more sets of instructions (e.g., software 1206) embodying any one or more of the methodologies or functions described herein. The software 1206 may also reside, completely or at least partially, within the memory 1205 and/or within the processing system 1220 during execution thereof by the system 1200, the memory and the processing system also constituting machine-accessible storage media. The software 1206 may further be transmitted or received over a network via the network interface 1215.

In one embodiment, a machine-accessible non-transitory medium (e.g., memory 1205) contains executable computer program instructions which when executed by a data processing system cause the system to performs operations or methods of the present disclosure. While the machine-accessible non-transitory medium (e.g., memory 1205) is shown in an exemplary embodiment to be a single medium, the term "machine-accessible non-transitory medium" should be taken to include a single medium or multiple media (e.g., a centralized or distributed database, and/or associated caches and servers) that store the one or more sets of instructions. The term "machine-accessible non-transitory medium" shall also be taken to include any medium that is capable of storing, encoding or carrying a set of instructions for execution by the machine and that cause the machine to perform any one or more of the methodologies of the present disclosure. The term "machine-accessible non-transitory medium" shall accordingly be taken to include, but not be limited to, solid-state memories, optical and magnetic media, and carrier wave signals.

Any of the following examples can be combined into a single embodiment or these examples can be separate embodiments. In one example of a first embodiment, a soil apparatus comprises a lower base portion for engaging in soil of an agricultural field; an upper base portion; and a neck portion having protrusions to insert into the lower base portion of a base and then lock when a region of the upper base portion is inserted into the lower base portion and this region of the upper base portion presses the protrusions to lock the neck portion to the upper base portion.

In another example of the first embodiment, the soil apparatus further comprises a window disposed in the lower base portion; and a sensor disposed in the lower base portion adjacent to the window, the sensor is configured to sense soil through the window when the lower base portion engages in soil of the agricultural field.

In another example of the first embodiment, the sensor for detecting characteristics of soil or a trench includes at least one of soil moisture, soil organic matter, soil temperature, seed presence, seed spacing, percentage of seeds firmed, and soil residue presence.

In another example of the first embodiment, the window is mounted flush with a lower surface of the ground-engaging lower portion such that soil flows underneath the window without building up over the window or along an edge of the window.

In another example of the first embodiment, a wear resistant insert is positioned in close proximity to the window to provide wear resistance for the window.

In another example of the first embodiment, the soil apparatus comprises a seed firmer.

In another example of the first embodiment, the upper base portion includes an internal cavity that is designed to receive a fluid application conduit and the internal cavity includes a rearward aperture through which the fluid application conduit extends for dispensing fluid behind the firmer.

In another example of the first embodiment, the lower base portion includes a resilient layer to position a circuit board in proximity to the window.

In another example of the first embodiment, the lower base portion includes a separate window portion to allow the window to be separately serviceable.

In another example of the first embodiment, the lower base portion includes a water drain slit that defines a feature for the window portion of the lower base portion to mate with the lower base portion.

In another example of the first embodiment, the neck portion includes a force relief to prevent damage to the lower base portion if the soil apparatus is engaged in soil while an agricultural implement is driven in a reverse direction.

In another example of the first embodiment, the neck portion includes a partial opening to prevent damage to the soil apparatus if the soil apparatus is engaged in soil while an agricultural implement is driven in a reverse direction.

In another example of the first embodiment, the lower base portion includes a lower outer portion to protect the lower base portion.

In another example of the first embodiment, the lower outer portion is made from a low coefficient of friction material.

In another example of the first embodiment, the lower outer portion covers at least 50% of a height of the lower base portion.

In another example of the first embodiment, the lower base portion additionally includes a second portion having an upper base portion and lower internal portion.

In another example of the first embodiment, the upper base portion of the second portion includes a channel.

In another example of the first embodiment, the lower internal portion is disposed below upper base portion and lower internal portion has an end for connection to the neck portion.

In another example of the first embodiment, the lower base portion is at least 50% of a combined height of the lower base portion and the upper base portion, and the lower base portion is made from a material having a coefficient of static friction less than or equal to 0.3.

In another example of the first embodiment, the coefficient of static friction is less than or equal to 0.2, and the lower base portion is at least 90% of the combined height.

In one example of a second embodiment, a soil apparatus comprises a lower base portion for engaging in soil of an agricultural field; an upper base portion; and a neck portion having protrusions to insert into openings of the lower base portion and then lock to the lower base portion when the openings accept the protrusions.

In another example of the second embodiment, the openings comprise holes to accept tabs of the protrusions for locking the neck portion to the lower base portion.

In another example of the second embodiment, the protrusions comprise two prongs.

In another example of the second embodiment, the neck portion includes a dividing ridge on the neck portion to divide a fluid tube and an electrical line.

In another example of the second embodiment, a window is disposed in the lower base portion; and a sensor is disposed in the lower base portion adjacent to the window. The sensor is configured to sense soil through the window when the lower base portion engages in soil of the agricultural field.

In another example of the second embodiment, the soil apparatus comprises a seed firmer.

In another example of the second embodiment, the lower base portion includes a resilient layer to position a circuit board in proximity to the window.

In another example of the second embodiment, the neck portion includes a force relief to prevent damage to the lower base portion if the soil apparatus is engaged in soil while an agricultural implement is driven in a reverse direction.

In another example of the second embodiment, the neck portion includes a spring to prevent damage to the soil apparatus if the soil apparatus is engaged in soil while an agricultural implement is driven in a reverse direction.

In another example of the second embodiment, the lower base portion includes a lower outer portion to protect the lower base portion.

In another example of the second embodiment, the lower outer portion is made from a low coefficient of friction material.

In another example of the second embodiment, the lower outer portion covers at least 50% of a height of the lower base portion.

In one example of a third embodiment, a soil apparatus comprises a base portion for engaging in soil of an agricultural field; a neck portion connected to the base portion, the neck portion configured to attach to an agricultural implement. The neck portion includes a force relief to prevent damage to the base portion if the soil apparatus is engaged in soil while the agricultural implement is driven in a reverse direction.

In another example of the third embodiment, the neck portion and the base portion are separate components.

In another example of the third embodiment, the neck portion is releasably connected to the agricultural implement.

In another example of the third embodiment, the force relief is a hole in the neck to allow the neck to break to prevent damage to the base portion.

In another example of the third embodiment, the force relief is a spring to allow the neck to flex.

In another example of the third embodiment, the base portion comprises a lower base portion and an upper base portion.

In one example of a fourth embodiment, a soil apparatus comprises a base portion for engaging in soil of an agricultural field, and the base portion is adapted for connection to an agricultural implement; a soil sensor disposed in or on the base portion for measuring a soil property; a force relief disposed on the base portion or between the base portion and the agricultural implement to prevent damage to the base portion if the soil apparatus is engaged in soil while the agricultural implement is driven in a reverse direction.

In another example of the fourth embodiment, the soil apparatus further comprises a neck portion connected to the base portion, the neck portion configured to attach to the agricultural implement, and the force relief is disposed in the neck portion.

In another example of the fourth embodiment, the soil apparatus comprises a base portion for engaging in soil of an agricultural field, and the base portion is adapted for connection to an agricultural implement.

In another example of the fourth embodiment, the soil apparatus comprises a window in the base portion; a wear resistant insert disposed in or on the base portion in one or more locations selected from the group consisting of i) ahead of the window in a direction of travel of the soil apparatus through soil, ii) above the window, and iii) below the window.

In another example of the fourth embodiment, the soil apparatus further comprises a neck portion connected to the base portion, the neck portion configured to attach to the agricultural implement.

In one example of a fifth embodiment, a soil apparatus comprises a base portion for engaging in soil of an agricultural field, and the base portion is adapted for connection to an agricultural implement. The base portion comprises an outer portion disposed over an internal portion; and wherein the outer portion is made from a material having a coefficient of static friction less than or equal to 0.3.

In another example of the fifth embodiment, the soil apparatus further comprises a neck portion connected to the base portion, the neck portion configured to attach to the agricultural implement.

In another example of the fifth embodiment, the internal portion comprises a lower base portion and an upper base portion.

In another example of the fifth embodiment, the lower base portion comprises a window, and the outer portion is not disposed over the window.

In another example of the fifth embodiment, the outer portion is at least 50% of a height of the base portion.

In another example of the fifth embodiment, the outer portion is at least 90% of a height of the base portion.

In another example of the fifth embodiment, the coefficient of static friction is less than or equal to 0.2.

In one example of a sixth embodiment, a method of calculating a uniform furrow measurement as a soil apparatus is drawn through a furrow includes the soil apparatus to measure one or more soil properties. The method comprises measuring during a measurement period with the soil apparatus a percent time out of furrow, optionally a percent voids, and optionally a percent moisture variation, or a percent of voids and a percent moisture variation, to obtain a measurement; and calculating uniform furrow by subtracting the measurement from 100 percent.

In another example of the sixth embodiment, the percent voids and the percent moisture variation are measured.

In another example of the sixth embodiment, the coefficient of static friction is less than or equal to 0.2.

In another example of the sixth embodiment, measuring the percent time out of the furrow comprising measuring a percentage of time that ambient light is detected.

In another example of the sixth embodiment, measuring the percent voids comprises measuring a percentage of time that a height off target is greater than a threshold value.

In another example of the sixth embodiment, measuring the percent moisture variation comprises calculating an absolute value of a difference between (an instantaneous reflection value of a first wavelength divided by an instantaneous reflection value of a second wavelength) subtract (running average of reflection value of the first wavelength divided by running average of reflection value of the second wavelength).

In another example of the sixth embodiment, the first wavelength is 1200 nm, and the second wavelength is 1450 nm.

In another example of the sixth embodiment, measuring the percent moisture variation comprises calculating an absolute value of (moisture indicator from instantaneous reflectance values subtract moisture indicator from running average reflectance values), wherein moisture indicator is calculated as ((1450 nm reflectance value actual subtract E1450) divided by (1450 nm reflectance value actual plus E1450), wherein E1450 is calculated as reflectance value at 1200 nm times 2 subtract 850.

In one example of a seventh embodiment, a method for determining a percentage of voids in a furrow as a soil apparatus is drawn through the furrow, the method comprises using the soil apparatus to obtain a reflectance from the furrow; measuring a height off target between the soil apparatus and the furrow; calculating a percentage of time that the measured height off target is greater than a threshold value different from an expected height off target between the soil apparatus and the furrow.

In one example of an eighth embodiment, a method for correcting a soil reflectance reading from a soil apparatus drawn through a furrow includes using the soil apparatus to obtain a reflectance from the furrow; measuring a height off target between the soil apparatus and the furrow; adjusting the height off target measurement to obtain a zero percent error for the height off target measurement.

In one example of a ninth embodiment, the processing system comprises a central processing unit ("CPU") to execute instructions for processing agricultural data; and a communication unit to transmit and receive agricultural data. The CPU is configured to execute instructions to obtain soil temperature from a soil apparatus having at least one sensor to sense soil temperature, to obtain air temperature, to determine a temperature offset based on the soil temperature and the air temperature, to obtain a predicted air temperature, and to determine predicted soil temperature for a future time period based on the temperature offset and the predicted air temperature.

In another example of the ninth embodiment, the CPU is further configured to execute instructions to set an alarm if the predicted soil temperature is below a minimum soil temperature for seed germination, greater than a maximum soil temperature for seed germination, or deviates by a defined amount from an average temperature at a point in time in the future.

In another example of the ninth embodiment, the CPU is further configured to execute instructions to correct an error in measuring reflectance from a reflectance sensor when a height off target of the soil apparatus occurs by determining a correction factor to convert a raw measured reflectance into a corrected measurement.

In another example of the ninth embodiment the correction factor is determined based on receiving measured reflectance data that is measured at different heights off target of the soil apparatus.

In one example of a tenth embodiment, a processing system comprises a processing unit to execute instructions for processing agricultural data; and a memory to store agricultural data, the processing unit is configured to execute instructions to obtain soil data from at least one sensor of an implement, and to determine, based on the soil data, seed germination data including at least one of time to germination, time to emergence, and seed germination risk for display on a display device.

In another example of the tenth embodiment, the display device to display seed germination data including a seed germination map with time to germination and time to emergence presented in hours or days, and time is blocked together into ranges and represented by different colors, shapes, or patterns.

In another example of the tenth embodiment, the time to germination is presented in hours on the display device with a first range of hours being assigned a first color, a second range of hours being assigned a second color, and a third range of hours being assigned a third color.

In another example of the tenth embodiment, the seed germination risk includes no germination/emergence, on time germination/emergence, or late germination/emergence.

In another example of the tenth embodiment, the seed germination risk includes factors other than time including deformities, damaged seed, reduced vigor, or disease.

In another example of the tenth embodiment, the seed germination data is calculated with at least one of the following measurements: soil moisture including quantity of water in the soil, matric potential of water in the soil, and seed germ moisture, soil temperature, soil organic matter, uniform furrow, furrow residue, soil type including sand, silt, clay, and residue cover including amount, location, distribution, and pattern of old and current crop matter on the soil surface.

In one example of an eleventh embodiment, a processing system comprises a processing unit to execute instructions for processing agricultural data; and a memory to store agricultural data, the processing unit is configured to execute instructions to obtain properties for seed environment data including at least two of soil color, residue, topography, soil texture and type, organic matter, soil temperature, soil moisture, seed shape and size, seed cold germ, furrow depth, predicted temperature, predicted precipitation, predicted wind speed, and predicted cloud cover, and to determine seed environment data based on the properties.

In another example of the eleventh embodiment, the processing unit is further configured to generate a seed environment indicator to indicate whether soil conditions are ready for planting during a specified time period.

In another example of the eleventh embodiment, the processing unit is further configured to generate an indicator to indicate whether soil conditions will remain acceptable through at least germination and emergence.

In another example of the eleventh embodiment, the processing unit is further configured to generate a seed environment score based on the seed environment data with a display device to display the seed environment score.

In another example of the eleventh embodiment, the display device to display the seed environment score including a first indicator to indicate acceptable planting conditions or a second indicator to indicate unacceptable planting conditions.

In another example of the eleventh embodiment, the display device to display seed environment score properties includes a current temperature, a current moisture, a predicted temperature, a predicted moisture, and whether each of these properties are within an acceptable range.

What is claimed is:

1. A method for determining a percentage of voids in a furrow as a soil apparatus is drawn through the furrow, the method comprising:

a. using the soil apparatus to obtain a reflectance from the furrow;

b. measuring a height off target between the soil apparatus and the furrow;

c. calculating a percentage of time that the measured height off target is greater than a threshold value that is different from an expected height off target between the soil apparatus and the furrow.

2. A method for correcting a soil reflectance reading from a soil apparatus drawn through a furrow, the method comprising:

a. using the soil apparatus to obtain a reflectance from the furrow;

b. measuring a height off target between the soil apparatus and the furrow;

c. adjusting the height off target measurement to obtain a zero percent error for the height off target measurement.

3. The method of claim 2 further comprising after measuring and before adjusting:

calculating a percentage of time that the measured height off target is greater than a threshold value that is different from an expected height off target between the soil apparatus and the furrow.

\* \* \* \* \*